US011545236B2

(12) United States Patent
Saladi et al.

(10) Patent No.: US 11,545,236 B2
(45) Date of Patent: Jan. 3, 2023

(54) METHODS AND SYSTEMS FOR PREDICTING MEMBRANE PROTEIN EXPRESSION BASED ON SEQUENCE-LEVEL INFORMATION

(71) Applicant: CALIFORNIA INSTITUTE OF TECHNOLOGY, Pasadena, CA (US)

(72) Inventors: Shyam M. Saladi, Pasadena, CA (US); William M. Clemons, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 448 days.

(21) Appl. No.: 15/444,247

(22) Filed: Feb. 27, 2017

(65) Prior Publication Data
US 2017/0249420 A1 Aug. 31, 2017

Related U.S. Application Data

(60) Provisional application No. 62/300,556, filed on Feb. 26, 2016.

(51) Int. Cl.
*G16B 40/20* (2019.01)
*G16B 40/00* (2019.01)
*G16B 25/00* (2019.01)

(52) U.S. Cl.
CPC ............. *G16B 40/20* (2019.02); *G16B 25/00* (2019.02); *G16B 40/00* (2019.02)

(58) Field of Classification Search
None
See application file for complete search history.

(56) References Cited

U.S. PATENT DOCUMENTS

| 2003/0149531 | A1* | 8/2003 | Hubert | ............... | A61K 51/1072 |
| | | | | | 702/1 |
| 2003/0236392 | A1* | 12/2003 | Isogai | .................... | C07K 14/47 |
| | | | | | 536/23.1 |

OTHER PUBLICATIONS

Hirokawa et al. SOSUI, a classification and secondary structure prediction system for membrane proteins. Bioinformatics, 14(4), 378-379, 1998.*
Ning et al. Drug Development Research 72, p. 138-146, 2011.*
Murphy et al. Nature Chemical Biology, 7, 327-330, 2011.*
Hecht et al. Drug Development Research 72, p. 53-65, 2011.*
Schaller et al. Chemical Engineering Science,vol. 121,2015, pp. 340-350.*
Yang et al Journal of Theoretical Biology, 2014, 61-73.*
Welsh et al. PLOS One, 4(9): e7002, 1-10, 2009.*
Aho, K., "asbio: A Collection of Statistical Tools for Biologists" (http://CRAN.Rproject.org/package=asbio), Nov. 2017, 229 pages.
Auguie, B., et al., "gridExtra: Miscellaneous Functions for "Grid" Graphics" (http://CRAN.R-project.org/package=gridExtra), Sep. 2017, 2 pages.
Berman H. M., et al., "The Protein Data Bank". Nucleic Acids Res. 28, 2000, pp. 235-242.
Bernaudat, F., et al., "Heterologous expression of membrane proteins: choosing the appropriate host". PloS One. 6, Dec. 2011, e29191, 17 pages.
Bill, R. M., et al., "Overcoming barriers to membrane protein structure determination". Nat. Biotechnol. 29, Apr. 2011, pp. 335-340.
Canty, A., et al., "boot: Bootstrap R (S-Plus) Functions", (https://CRAN.R-project.org/package=boot), Jul. 2017, 2 pgs.
Chartron, J. W., et al., "Cotranslational signal-independent SRP preloading during membrane targeting". Nature. 536, Aug. 2016, 27 pgs.
Chen, L., et al., "TargetDB: a target registration database for structural genomics projects". Bioinformatics. 20, May 2004, pp. 2860-2862.
Clarke, E., et al., "ggbeeswarm: Categorical Scatter (Violin Point) Plots" (https://github.com/eclarke/ggbeeswarm), Aug. 2017, 9 pages.
Cock, P. J. A., et al., "Biopython: freely available Python tools for computational molecular biology and bioinformatics". Bioinformatics. 25, Mar. 2009, pp. 1422-1423.
Cole, S. T., et al., "Deciphering the biology of *Mycobacterium tuberculosis* from the complete genome sequence". Nature. 393, Jun. 1998, pp. 537-544.
Coleman, J. R., et al., "Virus attenuation by genome-scale changes in codon pair Bias". Science. 320, Jun. 2008, 9 pgs.
Cunningham, F., et al., "Ensembl 2015". Nucleic Acids Res. 43, Oct. 2014, D662-669.
Daley, D. O., et al., "Global topology analysis of the *Escherichia coli* inner membrane Proteome". Science. 308, May 2005, pp. 1321-1323.
DeLong, E. R., et al., "Comparing the areas under two or more correlated receiver operating characteristic curves: a nonparametric approach". Biometrics. 44, Sep. 1988, pp. 837-845.
De Schutter, K., et al., "Genome sequence of the recombinant protein production host Pichia pastoris". Nat. Biotechnol. 27, Jun. 2009, pp. 561-566.
Dobrovetsky, E., et al., "High-throughput production of prokaryotic membrane Proteins". J. Struct. Funct. Genomics. 6, 2005, pp. 33-50.
Dos Reis, et al., "Unexpected correlations between gene expression and codon usage bias from microarray data for the whole *Escherichia coli* K-12 genome." Nucleic Acids Res. 31, 2003, pp. 6976-6985.
Engel, S. R., et al., "The reference genome sequence of *Saccharomyces cerevisiae*: then and now". G3 Bethesda Md. 4, Mar. 2014, pp. 389-398.

(Continued)

*Primary Examiner* — Michael L Borin
(74) *Attorney, Agent, or Firm* — Steinfl + Bruno, LLP

(57) ABSTRACT

Membrane protein expression can be predicted using statistical frameworks to provide an enhanced subset of sequences, out of an initial larger set of potentially expressing sequences, by using features derived from sequences and a model parameterized through a dataset of known expression levels. Also, membrane protein experimentation protocols can be designed using the statistical frameworks in concert known outcomes to identify which laboratory conditions are most likely to produce successful results.

16 Claims, 15 Drawing Sheets

Specification includes a Sequence Listing.

(56) References Cited

OTHER PUBLICATIONS

Engelman, D. M., "Identifying nonpolar transbilayer helices in amino acid sequences of membrane proteins". Annu. Rev. Biophys. Biophys. Chem. 15, 1986, pp. 321-353.
Eshaghi, S., et al., "An efficient strategy for high-throughput expression screening of recombinant integral membrane proteins". Protein Sci. 14, 2005, pp. 676-683.
Finn, R. D., et al., "Pfam: the protein families database". Nucleic Acids Res. 42, Nov. 2013, D222-230.
Fluman, N., et al., "mRNA-programmed translation pauses in the targeting of E. coli membrane proteins". eLife. 3, Aug. 2014, doi:10.7554/eLife.03440, 19 pgs.
Gamble, C. E., et al., "Adjacent Codons Act in Concert to Modulate Translation Efficiency in Yeast". Cell. 166, Jul. 2016, pp. 679-690.
Garnier, S., "viridis: Default Color Maps from "matplotlib"" (https://CRAN.Rproject.org/package=viridis), Mar. 2018, 6 pgs.
Geertsma, E. R., et al., "Quality control of overexpressed membrane proteins". Proc. Natl. Acad. Sci. U. S. A. 105, Apr. 2008, pp. 5722-5727.
Goodman, D. B., et al., "Causes and effects of N-terminal codon bias in bacterial genes". Science. 342, Sep. 2013, 8 pgs.
Gordon, E., et al., "Effective high-throughput overproduction of membrane proteins in Escherichia coli". Protein Expr. Purif. 62, Jul. 2008, pp. 1-8.
Harris. T. W., et al., "WormBase 2014: new views of curated biology". Nucleic Acids Res. 42, Nov. 2014, D789-793.
Harrower, M., et al., "ColorBrewer.org: an online tool for selecting colour schemes for maps". Cartogr. J. 40, Jun. 2003, pp. 27-37.
Heijne, G., "The distribution of positively charged residues in bacterial inner membrane proteins correlates with the transmembrane topology." EMBO J. 5, 1986, pp. 3021-3027.
Hessa, T., et al., "Molecular code for transmembrane-helix recognition by the Sec61 Translocon". Nature. 450, Dec. 2007, pp. 1026-1030.
Joachims, T., (ACM Press, http://portal.acm.org/citation.cfm?doid=775047.775067), 2002, p. 133-142.
Kall, L., et al., "A combined transmembrane topology and signal peptide prediction method". J. Mol. Biol. 338, Mar. 2004, pp. 1027-1036.
Kendall, M. G., "A New Measure of Rank Correlation". Biometrika. 30, Jun. 1938, pp. 81-93.
Korepanova, A., et al., "Cloning and expression of multiple integral membrane proteins from Mycobacterium tuberculosis in Escherichia coli". Protein Sci. 14, Sep. 2005, pp. 148-158.
Kuhn, M., "Building predictive models in R using the caret package". J Stat Soft Nov. 2008, 26 pgs.
Lechat, P., et al., "GenoList: an integrated environment for comparative analysis of microbial genomes". Nucleic Acids Res. 36, Nov. 2007, D469-474.
Lewinson, O., et al., "The funnel approach to the precrystallization production of membrane proteins". J. Mol. Biol. 377, Mar. 2008, 21 pgs.
Li, G. W., et al., "The anti-Shine-Dalgarno sequence drives translational pausing and codon choice in bacteria". Nature. 484, Oct. 2012, 15 pgs.
Linding, R., et al., "Protein disorder prediction: implications for structural proteomics". Structure. 11, Nov. 2003, pp. 1453-1459.
Loader, C., "locfit: Local Regression, Likelihood and Density Estimation". (http://CRAN.R-project.org/package=locfit) Apr. 2013, 1 pg.
Lorenz, R., et al., "ViennaRNA Package 2.0". Algorithms Mol. Biol. AMB. 6:26, 2011, 14 pgs.
Love, J. et al., "The New York Consortium on Membrane Protein Structure (NYCOMPS): a high-throughput platform for structural genomics of integral membrane proteins". J. Struct. Funct. Genomics. 11, Aug. 2010, pp. 191-199.
Lundstrom, K., et al., "Structural genomics on membrane proteins: comparison of more than 100 GPCRs in 3 expression systems". J. Struct. Funct. Genomics. 7, Nov. 2006, pp. 77-91.

Ma, P., et al., "An efficient strategy for small-scale screening and production of archaeal membrane transport proteins in Escherichia coli". PloS One. 8, e76913, Oct. 2013, 14 pgs.
Markowitz. V. M., et al., "IMG 4 version of the integrated microbial genomes comparative analysis system". Nucleic Acids Res. 42, Oct. 2013, D560-567.
Marshall, S. S., et al., "A Link between Integral Membrane Protein Expression and Simulated Integration Efficiency". Cell Rep. 16, Aug. 2016, pp. 2169-2177.
Mirzadeh, K., et al., "Enhanced Protein Production in Escherichia coli by Optimization of Cloning Scars at the Vector-Coding Sequence Junction". ACS Synth. Biol. May 2015, doi:10.1021/acssynbio.5b00033., pp. 959-965.
Nelson, K. E., et al., "Evidence for lateral gene transfer between Archaea and bacteria from genome sequence of Thermotoga maritima". Nature. 399, May 1999, pp. 323-329 (16 total pages).
Neuwirth, E., et al., RColorBrewer: ColorBrewer Palettes (http://CRAN.Rproject.org/package=RColorBrewer), Dec. 2014, 5 pgs.
Nordberg, H., et al., "The genome portal of the Department of Energy Joint Genome Institute: 2014 updates". Nucleic Acids Res. 42, Nov. 2013, D26-31.
Norholm, M. H. H., et al., "Manipulating the genetic code for membrane protein production: what have we learnt so far?" Biochim. Biophys. Acta. 1818, Aug. 2011, pp. 1091-1096.
Petrovskaya, L. E., et al., "Expression of G-protein coupled receptors in Escherichia coli for structural studies". Biochem. Mosc. 75, 2010, pp. 881-891.
Psakis, G., et al., "Expression screening of integral membrane proteins from Helicobacter pylori 26695". Protein Sci. 16, 2007, pp. 2667-2676.
Punta, M. et al., "Structural genomics target selection for the New York consortium on membrane protein structure". J. Struct. Funct. Genomics. 10, Oct. 2009, pp. 255-268.
R Core Team, "R: A Language and Environment for Statistical Computing" (R Foundation for Statistical Computing, Vienna, Austria; https://www.Rproject.org/); Mar. 2018, 60 pgs.
Robin, X., et al., "pROC: an open-source package for R and S+ to analyze and compare ROC curves". BMC Bioinformatics. 12, 77, 2011, 8 pgs.
Sarkar, C. A., et al., "Directed evolution of a G protein-coupled receptor for expression, stability, and binding selectivity". Proc. Natl. Acad. Sci. U. S. A. 105, Sep. 2008, pp. 14808-14813.
Schindelin, J., et al., "Fiji: an open-source platform for biological-image analysis". Nat. Methods. 9, Dec. 2013, 15 pgs.
Schlinkmann, K. M., et al., "Critical features for biosynthesis, stability, and functionality of a G protein-coupled receptor uncovered by all-versus-all mutations". Proc. Natl. Acad. Sci. U. S. A. 109, Jun. 2012, pp. 9810-9815.
Schloerke, B., et al., "GGally: Extension to "ggplot2"" (https://CRAN.Rproject.org/package=GGally), Aug. 2017, 91 pgs.
Schneider, C. A., et al., "NIH Image to ImageJ: 25 years of image analysis". Nat. Methods. 9, Jul. 2012, 12 pgs.
Schuler, G. D., et al., "Entrez: molecular biology database and retrieval system". Methods Enzymol. 266, 1996, pp. 141-162.
Seppala, S., et al., "Control of membrane protein topology by a single C-terminal residue". Science. 328, May 2010, pp. 1698-1700.
Smedley, D., et al., "The BioMart community portal: an innovative alternative to large, centralized data repositories". Nucleic Acids Res. 43, Apr. 2015, W589-598.
Surade, S., et al., "Comparative analysis and "expression space" coverage of the production of prokaryotic membrane proteins for structural genomics". Protein Sci. 15, 2006, pp. 2178-2189.
Swets, J. A., et al., "Better decisions through science". Sci. Am. 283, Oct. 2000, pp. 82-87.
Szakonyi, G., et al., "A genomic strategy for cloning, expressing and purifying efflux proteins of the major facilitator superfamily". J. Antimicrob. Chemother. 59, Apr. 2007, pp. 1265-1270.
Tange, O., "GNU Parallel—The Command-Line Power Tool". Login USENIX Mag. 36, Feb. 2011, pp. 42-47.
Tomb, J. F., et al., "The complete genome sequence of the gastric pathogen Helicobacter pylori". Nature. 388, Aug. 1997, pp. 539-547.

(56) References Cited

OTHER PUBLICATIONS

Towns, J., et al., "XSEDE: Accelerating Scientific Discovery". Comput. Sci. Eng. 16, Sep. 2014, pp. 62-74.

Tsochantaridis, I., et al., "Large Margin Methods for Structured and Interdependent Output Variables". J. Mach. Learn. Res. 6, 2005, pp. 1453-1484.

Uchiyama, I., et al., "MBGD update 2015: microbial genome database for flexible ortholog analysis utilizing a diverse set of genomic data". Nucleic Acids Res. 43, Nov. 2014, D270-276.

UniProt Consortium, "Reorganizing the protein space at the Universal Protein Resource (UniProt)". Nucleic Acids Res. 40, Nov. 2011, D71-75.

Van der Walt, S., et al., "The NumPy Array: A Structure for Efficient Numerical Computation". Comput. Sci. Eng. 13, 2011, 9 total pgs.

Van Lehn, R. C., et al., "Regulation of multispanning membrane protein topology via post-translational annealing". eLife. 4, Sep. 2015, doi:10.7554/eLife.08697., 23 pgs.

Wagner, S., et al., "Tuning *Escherichia coli* for membrane protein overexpression". Proc. Natl. Acad. Sci. U. S. A. 105, Sep. 2008, pp. 14371-14376.

Weihs, C., et al., "Data Analysis and Decision Support", (Springer-Verlag, Berlin/Heidelberg, 2005; http://link.springer.com/10.1007/3-540-28397-8_36), pp. 335-343 (361 total pgs).

Weinert, K., "datamart: Unified access to your data sources" (http://CRAN.Rproject.org/package=datamart), Feb. 2015, 48 pgs.

Weston, S., "foreach: Provides Foreach Looping Construct for R", Revolution Analytics (http://CRAN.R-project.org/package=foreach), Dec. 2017, 2 pgs.

Weston, S., "iterators: Provides Iterator Construct for R, Revolution Analytics" (https://CRAN.R-project.org/package=iterators), Dec. 2017, 11 pgs.

Weston, S., "doMC: Foreach Parallel Adaptor for "parallel"", Revolution Analytics (http://CRAN-project/package=doMC), Dec. 2017, 4 pgs.

Weston, S., "doParallel: Foreach Parallel Adaptor for the "parallel" Package", Revolution Analytics (https://CRAN.R-project.org/package=doParallel), Sep. 2017, 2 pgs.

White, S. H., "Biophysical dissection of membrane proteins". Nature. 459, May 2009, pp. 344-346.

Wickham, H., "The Split-Apply-Combine Strategy for Data Analysis". J. Stat. Softw. 40, Apr. 2011, pp. 1-29.

Wickham, H., "ggplot2: elegant graphics for data analysis" (Springer New York, Jul. 2010; http://had.co.nz.ggplot2/book). 3 pgs.

Wickham, H., "scales: Scale Functions for Visualization" (http://CRAN.Rproject.org/package=scales), Aug. 2017, 2 pgs.

Wickham, H., et al., "roxygen2: In-Source Documentation for R" (https://CRAN.R-project.org/package=roxygen2), Feb. 2017, 2 pgs.

Wilke, C. O., "cowplot: Streamlined Plot Theme and Plot Annotations for "ggplot2"" (http://CRAN.R-project.org/package=cowplot), Dec. 2017, 29 pgs.

Wimley, W. C., et al., "Solvation energies of amino acid side chains and backbone in a family of host-guest pentapeptides". Biochemistry (Mosc.). 35, 1996, pp. 5109-5124.

Xie, Y., et al., "Implementing Reproducible Computational Research", Eds. (Chapman and Hall/CRC, Oct. 2014; http://www.crcpress.com/product/isbn/9781466561595), 3 pgs.

Yang, Z. R., "RONN: the bio-basis function neural network technique applied to the detection of natively disordered regions in proteins". Bioinformatics. 21, Jun. 2005, pp. 3369-3376.

Zadeh, J. N., et al., "NUPACK: Analysis and design of nucleic acid systems". J. Comput. Chem. 32, Jul. 2010, pp. 170-173.

Zhou, J., et al., "EcoGene 3.0. Nucleic Acids Res". 41, Nov. 2013, D613-624.

Dragulescu, Adrian A, 2014. "Xlsx: Read, Write, Format Excel 2007 and Excel 97/2000/XP/2003 Files" (version 0.5.7). http://CRAN.R-project.org/packagexlsx.

E. R. Tufte, "The visual display of quantitative information" (*Graphics Press*, Cheshire, Conn, 2nd ed.,2001).

G. Van Rossum et al., "Python reference manual" (*Centrum voor Wiskunde en Informatica Amsterdam*,1995).

H. Wickham et al., "dplyr: A Grammar of Data Manipulation" (2015; http://CRAN.R-project.org/package=dplyr).

H. Wickham, "multidplyr: Partitioned data frames for "dplyr"" (https://github.com/hadley/multidplyr). Accessed on Sep. 20, 2019.

J. F. Peden, "Analysis of Codon Usage", *University of Nottingham*(2000).

P. Cock, "[BioPython] Downloading CDS sequences" (2009), (available at https://lists.open-bio.org/pipermail/biopython/2009-January/004886.html).

Perez, F, et al., 2007. "IPython: A System for Interactive Scientific Computing."*Computing in Science and Engineering*9 (3): 21-29. doi: 10.1109/MCSE.2007.53.

S. M. Bache et al., "magrittr: A Forward-Pipe Operator for R" (2014; https://CRAN.R-project.org/package=magrittr).

White S. "Membrane Proteins of Known 3D Structure." Dec. 3, 2015. http://blanco.biomol.uci.edu/mpstruc/.

Abou Elela, S. et al., "Role of the 5.8S rRNA in Ribosome Translocation.",*Nucleic Acids Research*, vol. 25, No. 9, pp. 1788-1794, (1997).

Anderson, H. et al., "Different Positively Charged Amino Acids Have Similar Effects on the Topology of a Polytopic Transmembrane Protein in *Escherichia coli*.", *Journal of Biological Chemistry*, vol. 267, No. 3, pp. 1491-1495, (1992), 6 pages.

Backmark A.E. et al., "Fluorescent probe for high-throughput screening of membrane protein expression" *Protein Science*, vol. 22, Jun. 2013, pp. 1124-1132.

Becker, T. et al., "Structure of Monomeric Yeast and Mammalian Sec61 Complexes Interacting with the Translating Ribosome.", *Science*, vol. 326, pp. 1369-1373, (2009).

Beckmann, R. et al., "Architecture of the Protein-Conducting Channel Associated with the Translating 80S Ribosome.", *Cell*, vol. 107, pp. 361-372, (2001).

Beltzer, J.P., et al., "Charged Residues Are Major Determinants of the Transmembrane Orientation of a Signal-Anchor Sequence.", *Journal of Biological Chemistry*, vol. 266, No. 2, pp. 973-978, (1991).

Berendsen, H.J.C. et al., "Molecular Dynamics with Coupling to an External Bath.", *Journal of Chemical Physics*, vol. 81, pp. 3684-3690, (1984), 8 pages.

Bieker, K.L. et al., "PrlA (SecY) and PrlG (SecE) Interact Directly and Function Sequentially during Protein Translocation in *E. coli*.", *Cell*, vol. 61, pp. 833-842, (1990).

Bilgin, N. et al., "Kinetic Properties of *Escherichia coli* Ribosomes with Altered Forms of S12.", *J. Mol. Biol.*, vol. 224, pp. 1011-1027, (1992).

Boehlke, K.W. et al., "Cellular Content of Ribonucleic Acid and Protein in *Saccharomyces cerevisiae* as a Function of Exponential Growth Rate: Calculation of the Apparent Peptide Chain Elongation Rate.", *Journal of Bacteriology*, vol. 121, No. 2, pp. 429-433, (1975).

Bogdanov, M. et al., "To Flip or Not to Flip: Lipid-Protein Charge Interactions are a Determinant of Final Membrane Protein Topology.", *J. Cell Biol.*, vol. 182, No. 5, pp. 925-935, (2008).

Bogsch, E.G. et al., "An Essential Component of a Novel Bacteria Protein Export System with Homologues in Plastids and Mitochondria.", *Journal of Biological Chemistry*, vol. 273, No. 29, pp. 18003-18006, (1998), 5 pages.

Bonardi, F. et al., "Probing the SecYEG Translocation Pore Size with Preproteins Conjugated with Sizable Rigid Spherical Molecules.", *PNAS*, vol. 108, No. 19, pp. 7775-7780, (2011), 7 pages.

Bondar, A.N. et al., "Dynamics of SecY Translocons with Translocation-Defective Mutations.", *Structure*, 18, pp. 847-857, (2010).

Brodsky, J.L. et al., "BiP and Sec63p are Required for Both Co- and Posttranslational Protein Translocation into the Yeast Endoplasmic Reticulum.", *Proc. Natl. Acad. Sci.*, vol. 92, pp. 9643-9646, (1995).

Buchete, N-V. et al., "Coarse Master Equations for Peptide Folding Dynamics.", *J. Phys. Chem. B*, vol. 112, No. 19, pp. 6057-6068, (2008), 13 pages.

Chandler, D., "Interfaces and the Driving Force of Hydrophobic Assembly.", *Nature Publishing Group*, vol. 437, pp. 640-647, (2005), 9 pages.

(56) References Cited

OTHER PUBLICATIONS

Chandler, D., "Roles of Classical Dynamics and Quantum Dynamics on Activated Processes Occurring in Liquids.", *Journal of Statistical Physics*, vol. 42, Nos. 1/2, pp. 49-67,(1986).

Chauwin, J-F. et al., "Strong Precursor-Pore Interactions Constrain Models for Mitochondrial Protein Import.", Biophysical Journal, vol. 74, pp. 1732-1743, (1998).

Cheng, Z. et al., "Slow Translocon Gating Causes Cytosolic Exposure of Transmembrane and Lumenal Domains During Membrane Protein Integration.", *Nat. Structural & Molecular Biology*, vol. 13, No. 10, pp. 930-936, (2006).

Chuang J. et al., "Anomalous Dynamics of Translocation.", *Physical Review E*, vol. 65, pp. 011802-1-011802-8, (2001), 8 pages.

Cobbold C. et al., "Aberrant trafficking of transmembrane proteins in human disease" *Trends in Cell Biology*, vol. 13 No. 12, Dec. 2003, pp. 639-647 (Abstract Only).

Crowley, K.S. et al., "Secretory Proteins Move Through the Endoplasmic Reticulum Membrane via an Aqueous, Gated Pore.", *Cell*, vol. 78, pp. 461-471, (1994).

Crowley, K.S. et al., "The Signal Sequence Moves Through a Ribosomal Tunnel into a Noncytoplasmic Aqueous Environment at the ER Membrane Early in Translocation.", *Cell*, vol. 73, pp. 1101-1115, (1993).

Dalbey R. E. et al., "Sec-translocase mediated membrane protein biogenesis" Biochimica et Biophysica Acta, vol. 1694, May 2004, pp. 37-53.

Denzer, A. et al., "Transmembrane Orientation of Signal-Anchor Proteins is Affected by the Folding State but not the Size of the N-Terminal Domain.", *The EMBO Journal*, vol. 14, No. 24, pp. 6311-6317, (1995).

Devaraneni, P.K. et al., "Stepwise Insertion and Inversion of a Type II Signal Anchor Sequence in the Ribosome-Sec61 Translocon Complex.", *Cell*, 146, pp. 134-147, (2011).

Dill, K.A. et al., "Principles of Protein Folding-A Perspective from Simple Exact Models.", *Protein Science*, 4, pp. 561-602, (1995).

Do, H. et al., "The Cotranslational Integration of Membrane Proteins into the Phospholipid Bilayer Is a Multistep Process.", *Cell*, vol. 85, pp. 369-378, (1996).

Dowhan, W. et al., "Lipid-Dependent Membrane Protein Topogenesis.", *Annu. Rev. Biochem.*, vol. 78, pp. 515-540, (2009), 30 pages.

Drew, D. et al., "Green Fluorescent Protein as an Indicator to Monitor Protein Overexpression in *Escherichia coli*.", *FEBS Letters* 507, pp. 220-224, (2001).

Duong, F. et al., "Sec-Dependent Membrane Protein Biogenesis: SecYEG, Preprotein Hydrophobicity and Translocation Kinetics Control the Stop-Transfer Function.", *The EMBO Journal*, vol. 17, No. 3, pp. 696-705, (1998).

Egea, P.F. et al., "Lateral Opening of a Translocon Upon Entry of Protein Suggests the Mechanism of Insertion into Membranes.", *PNAS*, vol. 107, No. 40, pp. 17182-17187, (2010).

Elston, T.C., "Models of Post-Translational Protein Translocation.", *Biophysical Journal*, vol. 79, pp. 2235-2251, (2000).

Erlandson, K.J. et al., "A Role for the Two-Helix Finger of the SecA ATPase in Protein Translocation.", *Nature*, vol. 455, pp. 984-988, (2008).

Final Office Action for U.S. Appl. No. 14/301,070, filed Jun. 10, 2014 on behalf of Thomas F. Miller III. dated Aug. 19, 2016. 9 pages.

Final Office Action for U.S. Appl. No. 14/301,070, filed Jun. 10, 2014 on behalf of Thomas F. Miller III. dated Aug. 3, 2017. 9 pages.

Frauenfeld, M. et al., "Cryo-EM Structure ofthe Ribosome-SecYE Complex in the Membrane Environment.", *Nature Structural & Molecular Biology*, vol. 18, No. 5, pp. 614-621, (2011), 9 pages.

Fujita, H. et al., "Positive Charges of Translocating Polypeptide Chain Retrieve an Upstream Marginal Hydrophobic Segment from the Endoplasmic Reticulum Lumen to the Translocon.", *Mol. Biol. Cell*, vol. 21, pp. 2045-2056, (2010).

Garrison, J.L. et al., "A Substrate-Specific Inhibitor of Protein Translocation into the Endoplasmic Reticulum.", *Nature*, vol. 436, pp. 285-289, (2005).

Go, N. et al., "Respective Roles of Short- and Long-Range Interactions in Protein Folding.", *Proc. Natl. Acad. Sci.*, vol. 75, No. 2, pp. 559-563, (1978).

Gobas, F.A. et al., "A Novel Method for Measuring Membrane-Water Partition Coefficients of Hydrophobic Organic Chemicals: Comparison with 1-Octanol-Water Partitioning.", *J. Pharm. Sci.*, vol. 77, No. 3, pp. 265-272, (1988).

Goder, V. et al., "Molecular Mechanism of Signal Sequence Orientation in the Endoplasmic Reticulum.", *The EMBO Journal*, vol. 22, No. 14, pp. 3645-3653, (2003).

Goder, V. et al., "Sec61p Contributes to Signal Sequence Orientation According to the Positive-Inside Rule.", *Mol. Biol. Cell*, vol. 15, pp. 1470-1478, (2004).

Goder, V. et al., "Topogenesis of Membrane Proteins: Determinants and Dynamics.", *FEBS Lett.* 504, pp. 87-93, (2001).

Goldschmidt, L. et al., "Toward Rational Protein Crystallization: A Web Server for the Design of Crystallizable Protein Variants.", *Protein Science*, vol. 16, pp. 1569-1576, (2007).

Gumbart, J. et al. "Free-Energy Cost for Translocon-Assisted Insertion of Membrane Proteins.", *PNAS*, vol. 108, No. 9, pp. 3596-3601, (2011).

Gumbart, J. et al., "Molecular Dynamics Studies of the Archaeal Translocon.", *Biophysical Journal*, vol. 90, pp. 2356-2367, (2006).

Gumbart, J. et al., Structural Determinants of Lateral Gate Opening in the Protein Translocon. *Biochemistry*, vol. 46, No. 39, pp. 11147-11157, (2007).

Guna A. et al., "Transmembrane Domain Recognition during Membrane Protein Biogenesis and Quality Control" *Current Biology*, vol. 28, Apr. 2018, pp. R498-R511.

Habdenteufel S. et al., "Chaperone-Mediated Sec61 Channel Gating during ER Import of Small Precursor Proteins Overcomes Sec61 Inhibitor-Reinforced Energy Barrier" *Cell Reports*, vol. 23, May 2018, pp. 1373-1386.

Haider, S. et al., "Simulations of a Protein Translocation Pore: SecY", *Biochemistry*, vol. 45, No. 43, pp. 13018-13024, (2006).

Hanke, A. et al., "Stretching Sing Ie Poly peptides: The Effect of Rotational Constraints in the Backbone". *EPL*, 92, 53001-p1-53001-p6, (2010), 6 pages.

Harley, C.A. et al., "Transmembrane Protein Insertion Orientation in Yeast Depends on the Charge Difference Across Transmembrane Segments, Their Total Hydrophobicity, and its Distribution.", *J. Biol. Chem.*, vol. 273, No. 38, pp. 24963-24971, (1998), 10 pages.

Hedin, L.E. et al., "Membrane Insertion of Marginally Hydrophobic Transmembrane Helices Depends on Sequence Context.", *J. Mol. Biol.*, 396, pp. 221-229, (2010).

Heinrich, S.U. et al., "The Sec61p Complex Mediates the Integration of a Membrane Protein by Allowing Lipid Partitioning of the Transmembrane Domain.", *Cell*, vol. 102, pp. 233-244, (2000).

Heritage, D. et al., "Translocon Pores in the Endoplasmic Reticulum are Permeable to a Neutral, Polar Molecule.", *J. Biol. Chem.*, vol. 276, No. 25, pp. 22655-22662, (2001), 9 pages.

Hessa, T. et al., "Membrane Insertion of a Potassium-Channel Voltage Sensor.", *Science*, vol. 307, p. 1427, (2005), 2 pages.

Hessa, T. et al., "Molecular Code for Transmembrane-Helix Recognition by the Sec61 Translocon.", *Nature*, vol. 450, pp. 1026-1030, (2007), 7 pages.

Hessa, T. et al., "Recognition of Transmembrane Helices by the Endoplasmic Reticulum Translocon.", *Nature*, vol. 433, pp. 377-381, (2005).

Hessa, T., et al., "Stop-Transfer Efficiency of Marginally Hydrophobic Segments Depends on the Length of the Carboxyterminal Tail.", *The EMBO Journal*, vol. 4, No. 2, pp. 178-183, (2003).

Higy, M. et al., "Probing the Environment of Signal-Anchor Sequences During Topogenesis in the Endoplasmic Reticulum.", *Biochemistry*, vol. 44, No. 6, pp. 2039-2047, (2005), 10 pages.

Hikita, C. et al., "Effects of Total Hydrophobicity and Length of the Hydrophobic Domain of a Signal Peptide on in vitro Translocation Efficiency.", *J. Biol. Chem.*, vol. 267, No. 7, pp. 4882-4888, (1992).

Hizlan, D. et al., "Structure of the SecY Complex Unlocked by a Preprotein Mimic.", *Cell Reports* 1, pp. 21-28, (2012).

Hoover, J. et al., "DNAWorks: an Automated Method for Designing Oligonucleotides for PCR-Based Gene Synthesis.", *Nucleic Acids Research*, vol. 30, No. 10, e43, (2002), 7 pages.

(56) References Cited

OTHER PUBLICATIONS

Hummer, G., "From Transition Paths to Transition States and Rate Coefficients.", *J. Chem. Physics*, vol. 120, No. 2, pp. 516-523, (2004).

Huopaniemi, I. et al., "Langevin Dynamics Simulations of Polymer Translocation Through Nanopores.", *J. Chem. Phys.* 125, 124901, (2006), 8 pages.

Jungnickel, B. et al., "A Posttargeting Signal Sequence Recognition Event in the Endoplasmic Reticulum Membrane.", *Cell*, vol. 82, pp. 261-270, (1995).

Junne, T. et al., "Mutations in the Sec61p Channel Affecting Signal Sequence Recognition and Membrane Protein Topology.", *J. Biol. Chem.*, vol. 282, No. 45, pp. 33201-33209, (2007), 10 pages.

Junne, T. et al., "The Hydrophobic Core of the Sec61 Translocon Defines the Hydrophobicity Threshold for Membrane Integration.", *Mol. Biol. Cell*, vol. 21, pp. 1662-1670, (2010).

Kamerlin, S.CL. et al., "Coarse-Grained (Multiscale) Simulations in Studies of Biophysical and Chemical Systems.", *Annu. Rev. Phys. Chem.*, 62, pp. 41-64, (2011), 27 pages.

Kida, Y. et al., "Function of Positive Charges Following Signal-Anchor Sequences During Translocation of the N-Terminal Domain.", *J. Biol. Chem.*, vol. 281, No. 2, pp. 1152-1158, (2006), 8 pages.

Kim S. J. et al., "Combinatorial Control of Prion Protein Biogenesis by the Signal Sequence and Transmembrane Domain" *The Journal of Biological Chemistry*, vol. 276 No. 28, Jul. 2001, pp. 26132-26140.

Kim, S.J. et al., "Signal Sequences Control Gating of the Protein Translocation Channel in a Substrate-Specific Manner.", *Developmental Cell*, vol. 2, pp. 207-217, (2002).

Klauda, J.B. et al., "Update of the CHARMM All-Atom Additive Force Field for Lipids: Validation on Six Lipid Types.", *J. Phys. Chem. B*, vol. 114, No. 23, pp. 7830-7843, (2010).

Klock, H.E. et al., "The Polymerase Incomplete Primer Extension (PIPE) Method Applied to High-Throughput Cloning and Site-Directed Mutagenesis." *Methods Mol. Biol.*, vol. 498, pp. 91-103, (2009).

Krautler, V. et al., "A Fast SHAKE Algorithm to Solve Distance Constraint Equations for Small Molecules in Molecular Dynamics Simulations.", *J. Comput. Chem.*, vol. 22, No. 5, pp. 501-508, (2001).

Kremer, K. et al., "Dynamics of Entangled Linear Polymer Melts: A Molecular-Dynamics Simulation.", *J Chem Phys.*, vol. 92, No. 8, pp. 5057-5086, (1990).

Krogh, B. et al., "Predicting Transmembrane Protein Topology with a Hidden Markov Model: Application to Complete Genomes.", J. Mol. Biol., 305, pp. 567-580, (2001).

Kyte, J. et al., "A Simple Method for Displaying the Hydropathic Character of a Protein.", *J. Mol. Biol.*, 157, pp. 105-132, (1982).

Lerch-Bader, M. et al., "Contribution of Positively Charged Flanking Residues to the Insertion of Transmembrane Helices into the Endoplasmic Reticulum.", *PNAS*, vol. 105, No. 11, pp. 4127-4132, (2008).

Lewinson, O. et al., "The Funnel Approach to the Precrystallization Production of Membrane Proteins.", *J. Mol. Biol.*, 377, pp. 62-73, (2008).

Li, M.S. et al., "Folding in Two-Dimensional Off-Lattice Models of Proteins.", *Phys. Rev. E*, vol. 59, No. 1, pp. 970-976, (1999).

Liebermeister, W. et al., "Ratcheting in Post-Translational Protein Translocation: A Mathematical Model.", *J. Mol. Biol.*, 305, pp. 643-656, (2001).

Lindahl, E. et al., "Membrane Proteins: Molecular Dynamics Simulations.", *Current Opinion in Structural Biology*, 18, pp. 425-431, (2008).

Lundstrom K. "Structural genomics on membrane proteins: mini review" Comb Chem High Throughput Screen, vol. 7(5), Aug. 2004, pp. 431-439.

Luo, K. et al., "Influence of Polymer-Pore Interactions on Translocation.", *Phys. Rev. Lett.*, 99, 148102, (2007), 4 pages.

Luo, K. et al., "Sequence Dependence of DNA Translocation Through a Nanopore.", *Phys. Rev. Lett.*, 100, 058101, (2008), 4 pages.

Mackerell, A.D. et al., "All-Atom Empirical Potential for Molecular Modeling and Dynamics Studies of Proteins.", *J. Phys. Chem. B*, vol. 102, No. 18, pp. 3586-3616, (1998).

Maifeld, S.V. et al., "Secretory Protein Profiling Reveals TNF-α Inactivation by Selective and Promiscuous Sec61 Modulators.", *Chemistry & Biology* 18, pp. 1082-1088, (2011).

Matlack, K.E.et al., "BiP Acts as a Molecular Ratchet During Posttranslational Transport of Prepro-αFactor across the ER Membrane.", *Cell*, vol. 97, pp. 553-564, (1999).

McKenna M. et al., "Mycolatone reveals the substrate-driven complexity of Sec61-dependent transmembrane protein biogenesis" Journal of Cell Science, Apr. 2017, vol. 130(7), pp. 1307-1320.

Meindl-Beinker, N.M. et al., "Asn- and Asp-mediated Interactions Between Transmembrane Helices During Translocon-Mediated Membrane Protein Assembly.", *The EMBO Reports*, vol. 7, No. 11, pp. 1111-1116, (2006).

Membrane protein —Wikipedia, the free encyclopedia. Archive Date: Jan. 20, 2016 https://web.archive.org/web/20160120184356/https://en.wikipedia.org/wiki/Membrane_protein 5 pages.

Miller-Vedam L. E. "Structural and mechanistic basis of the EMC-dependent biogenesis of distinct transmembrane clients" *eLife*, vol. 9, Nov. 2020, 47 pages.

Moon, C.P. et al., "Side-Chain Hydrophobicity Scale Derived from Transmembrane Protein Folding into Lipid Bilayers.", *PNAS*, vol. 108, No. 25, pp. 10174-10177, (2011).

Muthukumar, M., "Polymer Translocation Through a Hole.", *J. Chem. Physiol.*, vol. 111, No. 22, pp. 10371-10374, (1999), 5 pages.

Nilsson, I. et al., "Fine-Tuning the Topology of a Polytopic Membrane Protein: Role of Positively and Negatively Charged Amino Acids.", *Cell*, vol. 62, pp. 1135-1141, (1990).

Non-Final Office Action for U.S. Appl. No. 14/301,070, filed Jun. 10, 2014 on behalf of Thomas F. Miller III. dated Mar. 29, 2016. 12 pages.

Ojemalm, K. et al., "Apolar Surface Area Determines the Efficiency of Translocon-Mediated Membrane-Protein Integration into the Endoplasmic Reticulum.", *PNAS*, vol. 108, No. 31, E359-E364, (2011), 7 pages.

O'Keefe S. et al., "Membrane protein biogenesis at the ER: the highways and byways" *The FEBS Journal*, Apr. 2021, 29 pages.

Panja, D. et al., "Anomalous Dynamics of Unbiased Polymer Translocation through a Narrow Pore.", *J. Phys. Condens. Matter* 19, 432202-432202, (2007), 8 pages.

Park, E. et al., "Preserving the Membrane Barrier for Small Molecules During Bacterial Protein Translocation.", *Nature*, vol. 473, pp. 239-242, (2011), 6 pages.

Parks, G.D. et al., "Topology of Eukaryotic Type II Membrane Proteins: Importance of N-Terminal Positively Charged Residues Flanking the Hydrophobic Domain.", *Cell*, vol. 64, pp. 777-787, (1991).

Plath, K. et al., "Signal Sequence Recognition in Posttranslational Protein Transport Across the Yeast ER Membrane.", *Cell*, vol. 94, pp. 795-807, (1998).

Ramadurai, S. et al., "Lateral Diffusion of Membrane Proteins.", *J. Am. Chem. Soc.*, vol. 131, No. 35, pp. 12650-12656, (2009).

Ramasamy S. et al., "The Glove-like Structure of the Conserved Membrane Protein TatC Provides Insight into Signal Sequence Recognition in Twin-Arginine Translocation.", *Structure* 21, pp. 777-788, (2013).

Rapoport, T.A. et al., "Membrane-Protein Integration and the Role of the Translocation Channel.", *Trends Cell Biol.*, vol. 14, No. 10, pp. 568-575, (2004).

Rapoport, T.A., "Protein Translocation Across the Eukaryotic Endoplasmic Reticulum and Bacterial Plasma Membranes.", *Nature*, vol. 450, pp. 663-669, (2007).

Restriction Requirement for U.S. Appl. No. 14/301,070, filed Jun. 10, 2014 on behalf of Thomas F. Miller III. dated Jan. 13, 2016. 9 pages.

Rollauer, S.E. et al., "Structure of the TatC Core of the Twin-Arginine Protein Transport System.", *Nature*, vol. 492, pp. 210-214, (2012), 6 pages.

(56) References Cited

OTHER PUBLICATIONS

Rutkowski, D.T. et al., "Substrate-Specific Regulation of the Ribosome-Translocon Junction by N-Terminal Signal Sequences.", *PNAS*, vol. 98, No. 14, pp. 7823-7828, (2001).

Rychkova, A. et al., "On the Energetics of Translocon-Assisted Insertion of Charged Transmembrane Helices into Membranes.", *PNAS*, vol. 107, No. 41, pp. 17598-17603, (2010).

Saaf, A. et al., "Stop-Transfer Function of Pseudo-Random Amimo Acid Segments During Translocation Across Prokaryotic and Eukaryotic Membranes.", *Eur. J. Biochem.* 251, pp. 821-829, (1998).

Sanders, S.L. et al., "Sec61p and BiP Directly Facilitate Polypeptide Translocation into the ER.", *Cell*, vol. 69, pp. 353-365, (1992).

Schlegel, S. et al., "Revolutionizing Membrane Protein Overexpression in Bacteria.", *Microbial Biotechnology*, 3(4), pp. 403-411, (2010).

Scott, D.J. et al., "Stabilizing Membrane Proteins Through Protein Engineering.", *Current Opinion in Chemical Biology*, 17, 427-435, (2013).

Seiser, R.M. et al., "The Fate of Membrane-Bound Ribosomes Following the Termination of Protein Synthesis.", *J. Bio. Chem.*, vol. 275, No. 43, pp. 33820-33827, (2000).

Seppala, S. et al., "Control of Membrane Protein Topology by a Single C-Terminal Residue.", *Science*, vol. 328, pp. 1698-1700, (2010), 4 pages.

Shan, Y. et al., "Gaussian Split Ewald: A Fast Ewald Mesh Method for Molecular Simulation.", *J. Chem. Phys.*, 122, pp. 054101-1-05401-13, (2005), 14 pages.

Shaw, A.S. et al., "Evidence for the Loop Model of Signal-Sequence Insertion into the Endoplasmic Reticulum.", *Proc. Natl. Acad. Sci. USA*, vol. 85, pp. 7592-7596, (1988).

Shaw, D.E. et al., "Atomic-Level Characterization of the Structural Dynamics of Proteins.", *Science*, vol. 330, pp. 341-346, (2010), 7 pages.

Simon, S.M. et al., What drives the translocation of proteins? Proc. Natl. Acad. Sci. USA, vol. 89, pp. 3770-3774, (1992).

Smith, M.A. et al., "Modeling the Effects of prl Mutations on the *Escherichia coli* SecY Complex.", *J.Bacteriol.*, vol. 187, pp. 6454-6465, (2005), 13 pages.

Sonoda, Y. et Al., "Tricks of the Trade used to Accelerate High-Resolution Structure Determination of Membrane Proteins.", *FEBS letters* 584, pp. 2539-2547, (2010).

Sriraman, S. et al., "Coarse Master Equation from Bayesian Analysis of Replica Molecular Dynamics Simulations.", *J. Phys. Chem. B*, vol. 109, No. 14, pp. 6479-6484, (2005).

Staple, S. H. et al., "Model for Stretching and Unfolding the Giant Multidomain Muscle Protein Using Single-Molecule Force Spectroscopy." *Phys. Rev. Lett.* 101, pp. 248301-1-248301-4, (2008), 4 pages.

Sung, W. et al., "Polymer Translocation through a Pore in a Membrane.", *Phys. Rev. Letters*, vol. 77, No. 4, pp. 783-786, (1996).

Terragni B. et al., "Post-translational dysfunctions in channelopathies of the nervous system" *Neuropharmacology*, vol. 132, Apr. 2018, pp. 31-42.

Tian, P., "Size, Motion, and Function of the SecY Translocon Revealed by Molecular Dynamics Simulations with Virtual Probes.", *Biophys. J.*, vol. 90(8), pp. 2718-2730, (2006).

Tsukazaki, T. et al., "Conformational Transition of Sec Machinery Inferred from Bacterial SecYE Structures.", *Nature*, vol. 455, pp. 988-991, (2008), 5 pages.

Tuckerman, M. et al., "Reversible Multiple Time Scale Molecular Dynamics.", *J. Chem. Phys.*, vol. 97, No. 3, pp. 1990-2001, (1992), 13 pages.

Tyedmers, J. et al., "Polypeptide-Binding Proteins Mediate Completion of Co-Translational Protein Translocation into the Mammalian Endoplasmic Reticulum.", *The EMBO Reports*, vol. 4, No. 5, pp. 505-510, (2003).

Vaes, W.H.J. et al., "Understanding and Estimating Membrane/Water Partition Coefficients: Approaches to Derive Quantitative Structure Property Relationships.", *Chem. Res. Toxicol.*, vol. 11, No. 8, pp. 847-854, (1998).

Van Den Berg, B. et al., "X-ray Structure of a Protein-Conducting Channel.", *Nature*, vol. 427, pp. 36-44, (2004).

Von Heijne, G., "The Distribution of Positively Charged Residues in Bacterial Inner Membrane Proteins Correlates with the Trans-Membrane Topology.", *The EMBO Journal*, vol. 5, No. 11, pp. 3021-3027, (1986).

WERTEN P.J.L. et al., "Progress in the analysis of membrane protein structure and function" *FEBS Letters*, Aug. 2002, vol. 529, pp. 65-72.

Zhang, B. et al., "Direct Simulation of Early-Stage Sec-Facilitated Protein Translocation.", *J. Am. Chem Soc.*, 134, pp. 13700-13707, (2012).

Zhang B. et al., "Hydrophobically Stabilized Open State for the Lateral Gate of the Sec Translocon.", *PNAS*, vol. 107, No. 12, pp. 5399-5404, (2010).

Zhang B. et al., "Long-Timescale Dynamics and Regulation of Sec-Facilitated Protein Translocation.", *Cell Reports* 2, pp. 927-937, (2012).

Zimmer, J. et al., "Conformational Flexibility and Peptide Interaction of the Translocation ATPase SecA.", *J. Mol. Biol.*, 394, pp. 606-612, (2009).

Zimmer, J. et al., "Structure of a Complex of the ATPase SecA and the Protein-Translocation Channel.", *Nature*, vol. 455, 936-943, (2008), 10 pages.

\* cited by examiner

METHODS AND SYSTEMS FOR PREDICTING MEMBRANE PROTEIN EXPRESSION BASED ON SEQUENCE-LEVEL INFORMATION

CROSS-REFERENCE TO RELATED APPLICATIONS

The present application claims priority to U.S. Patent Application No. 62/300,556 filed on Feb. 26, 2016, the disclosures of which is incorporated herein by reference in its entirety.

STATEMENT OF GOVERNMENT GRANT

This invention was made with government support under Grant No. GM105385 awarded by the National Institutes of Health. The government has certain rights in the invention.

FIELD

The present disclosure relates to protein biogenesis and in particular to methods and systems for predicting membrane protein expression based on sequence level information.

BACKGROUND

Prediction of protein expression from sequence information has been the focus of research as the ability to know whether a certain sequence can express impacts many applications in various fields such as biological and medical research, where such expression is often performed in a controlled environment.

However, the biological processes presiding expression of sequences in a biological environment are complex and not completely understood (and might never be), which affect the ability to efficiently and accurately predict whether and to what extent and/or yield a certain sequence will express in a certain environment.

Accordingly, protein expression can, of course, be tested experimentally within a protein, protein family, or a set of targets. However, achievement of efficient and/or high yield prediction methods remains challenging.

SUMMARY

Provided herein are methods and systems that, in several embodiments, allow decoding of qualitative and/or quantitative, predictive information of a protein biogenesis from biological sequences (nucleotide and/or protein) and in particular to predict, at least statistically, the heterologous expression of membrane proteins in a set environment.

According to a first aspect of the disclosure, a method for membrane protein expression is disclosed, comprising: selecting an initial set of sequences with known protein expression for a membrane protein; transforming the initial set of sequences to features including nucleotide features, protein features, or both; dividing the initial set of sequences into a training set and a test set; creating a model based on the training set, the model providing statistical analysis of expressing a membrane protein; validating the model with the test set; using the model on a distinct set of sequences; creating an experimentation set of sequences by selecting a subset of the input set of sequences, wherein the selection is based on the results of the using the model; performing experimental testing on the subset such that expression levels are determined for each member of the subset, creating a positive result set of sequences that have positive expression of the membrane protein as determined by the experimental testing; and using the positive result set to express the membrane protein.

According to a second aspect of the disclosure, a method for designing membrane protein expression experimental protocol, comprising: selecting a membrane protein of interest; identifying expressed similar proteins in a plurality of conditions; for each of the plurality of conditions: selecting an initial set of sequences with known protein expression for a membrane protein, transforming the initial set of sequences to features including nucleotide features, protein features, or both, dividing the initial set of sequences into a training set and a test set, creating a model based on the training set, the model providing statistical analysis of expressing the membrane protein, and validating the model with the test set; determining which of the plurality of conditions has a best predictive performance based on the testing for each of the plurality of conditions; performing membrane protein expression experiments on the membrane protein of interest under those of the plurality of conditions that have the best predictive performance.

In particular, methods and systems herein described allow in several embodiments to predict expression of an IMP without the need of a detailed characterization (e.g. atomistic structure) of biological macromolecules involving a large mass of the molecule—typically only achievable through heterologous expression in a recombinant host.

In particular, methods and systems herein described allow, in several embodiments, an appropriate weighting of parameters calculated from sequences (nucleotide and/or protein) to produce a score that relates to the likelihood that a given IMP will be successfully expressed, providing an increase in efficiency in prediction of the sequences that are expressed.

Methods and systems herein described allow, in several embodiments, to predict expression of an IMP with a statistical approach in the mapping between sequence features (parameters) and levels of expression, providing a higher true-positive percentage

DETAILED DESCRIPTION

Figure 1:
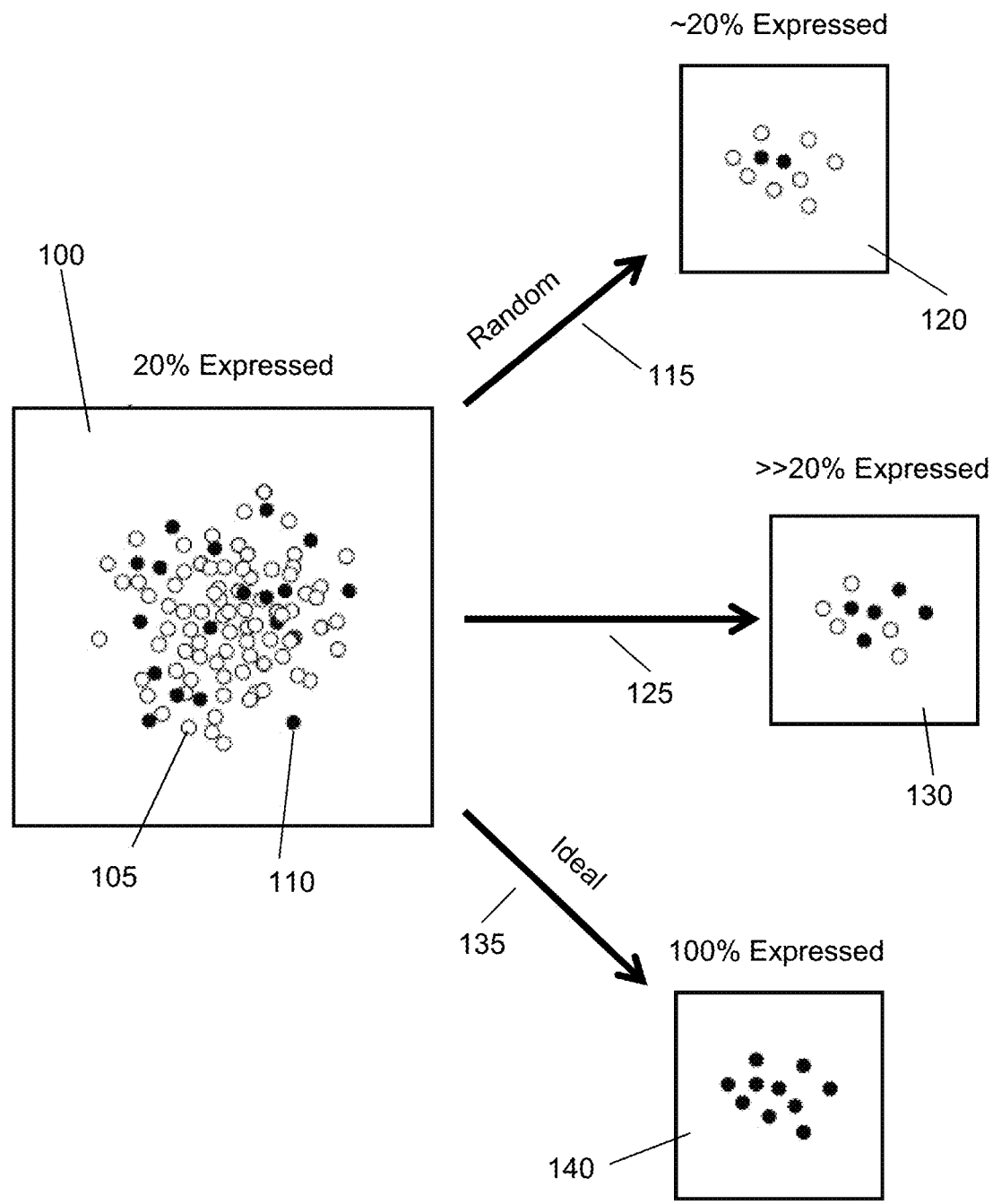
FIG. 1 shows an example of different approaches to selecting a subset of genomes to test experimentally for protein expression.

Provided herein are methods and systems that in several embodiments allow decoding of qualitative and/or quantitative, predictive information from biological sequences (polynucleotide and/or protein)

The term "polynucleotide" as used herein indicates an organic polymer composed of two or more monomers including nucleotides. The term "nucleotide" refers to any of several compounds that consist of a ribose or deoxyribose sugar joined to a purine or pyrimidine base and to a phosphate group and that is the basic structural unit of nucleic acids.

Exemplary monomers of a polynucleotide comprise deoxyribonucleotide and ribonucleotides. The term "deoxyribonucleotide" refers to the monomer, or single unit, of DNA, or deoxyribonucleic acid. Each deoxyribonucleotide comprises three parts: a nitrogenous base, a deoxyribose sugar, and one or more phosphate groups. The nitrogenous base is typically bonded to the 1' carbon of the deoxyribose, which is distinguished from ribose by the presence of a proton on the 2' carbon rather than an —OH group. The phosphate group is typically bound to the 5' carbon of the sugar. The term "ribonucleotide" refers to the monomer, or single unit, of RNA, or ribonucleic acid. Ribonucleotides have one, two, or three phosphate groups attached to the ribose sugar.

Polynucleotides can be identified by using standard molecular biology approaches or through direct sequencing as understood by a person skilled in the art. In particular, a sequence of a polynucleotide can be determined from nucleic acid sequencing. The term "nucleic acid sequencing" is a method for determining the order of nucleotides present in a given DNA or RNA molecule or other polynucleotide molecule, i.e. the order of the four bases adenine, guanine, cytosine and thymine in a strand of DNA or the four bases adenine, guanine, cytosine and uracil in RNA. Approaches to DNA or RNA sequencing include dideoxy sequencing, also known as Sanger sequencing, cyclic array sequencing, sequencing by hybridization, microelectrophoresis, mass spectrometry and nanopore sequencing. Detailed information about these sequencing techniques can be found in related literatures and will be understood by a person of ordinary skill in the art.

The term "protein" as used herein indicates a polypeptide with secondary, tertiary, and possibly quaternary structure. The protein's secondary, tertiary, and quaternary structure can occur on a variety of length scales (tenths of Å to nm) and time scales (ns to s), so that in various instances the secondary, tertiary and possibly quaternary structures are dynamic and not perfectly rigid.

The term "polypeptide" as used herein indicates a polymer composed of two or more amino acid monomers and/or analogs thereof wherein the portion formed by the alpha carbon, the amine group and the carboxyl group of the amino acids in the polymer forms the backbone of the polymer. As used herein the term "amino acid", "amino acid monomer", or "amino acid residue" refers to any of the naturally occurring amino acids, any non-naturally occurring amino acids, and any artificial amino acids, including both D and L optical isomers of all amino acid subsets. In particular, amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid.

The term "polypeptide" includes amino acid polymers of any length including full length proteins, as well as analogs and fragments thereof. The polypeptide provides the primary structure of a protein wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds. Polypeptides in the sense of the present disclosure are usually composed of a linear chain of amino acid residues covalently linked by peptide bond. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated counting of residues in a polypeptide is performed from the N-terminal end (NH2-group), which is the end where the amino group is not involved in a peptide bond to the C-terminal end (—COOH group) which is the end where a COOH group is not involved in a peptide bond.

Proteins can be identified by x-ray crystallography, purification and direct sequencing, immuno precipitation, from their corresponding nucleotide sequences, and a variety of other methods as understood by a person skilled in the art. Proteins can be provided in vitro or in vivo by several methods identifiable by a skilled person.

In embodiments herein described, methods and systems of the disclosure allow to predict, at least statistically, the heterologous expression of membrane proteins in outcome of a protein biogenesis in the biological environment.

"Protein biogenesis" indicates a multistep biological pathway leading to the protein synthesis in a biological system, wherein the biological system indicates any system wherein protein expression is performed in connection with a biological membrane or a biomimetic environment. The biological membrane indicates enclosing or separating membrane that acts as a selectively permeable barrier within a biological cell. Exemplary biological membrane comprises the Endoplasmic Reticulum or mitochondrial membranes of eukaryotes and inner membrane of bacteria. The biomimetic environment indicates an amphipathic lipid bilayer or any other amphipathic lipid environment suitable to accommodate segments of a protein. Exemplary biomimetic membranes comprise detergent micelles, lipidic cubic phase, a proteoliposome, and additional environments identifiable by a skilled person. Exemplary biological systems comprise a eukaryotic cell, a bacterial cell, an archaeal cell, or a cell-free system.

A "cell-free" system indicates an in vitro system that contains the basic components required for the multistep biological pathway to take place outside a cellular environment. In some embodiments of biological systems of the disclosure, protein synthesis can occur via a process called translation. During translation, mRNA is read by ribosomes to generate a protein polypeptide chain. This process is performed by an array of components within the cell including ribosomes and transfer RNA (tRNA), which serves as an adaptor by binding amino acids on one end and interacting with mRNA at the other end; the latter pairing between the tRNA and mRNA ensures that an amino acid corresponding to a codon in the mRNA is added to the chain. The term "ribosome" as used herein refers to a minute particle consisting of RNA and associated proteins found in large numbers in the cytoplasm of living cells. Ribosomes bind messenger RNA and transfer RNA to synthesize polypeptides and proteins. Examples include the 80S ribosome in Eukaryotes. Translation usually proceeds in an N- to C-terminal direction with additional amino acids added by the ribosome to the C-terminus as determined by the mRNA sequence which encodes the primary structure of the protein.

Once translated, a protein's primary structure can be modified by modifications of the polypeptide chain and/or amino acid monomers identified as post-translation modifications. Post translational modifications can affect topogenesis and folding of a protein. Exemplary posttranslational modifications comprise protease digestion (e.g. secreted proteins containing signal sequences which can be cleaved), attachment of functional groups (such as acetate, phosphate, various lipids and carbohydrates), changes in the chemical nature of an amino acid (e.g. citrullination), formation of intrapolypeptide bonds (e.g. formation of disulfide bridges), and additional modification of the covalent bonds in the polypeptide chain and/or amino acid residues not performed by the ribosome The term "protein folding" as used herein indicates the creation of secondary, tertiary, and quaternary structure during and after translation. Protein folding is driven a wide array of forces such as the non-specific hydrophobic interactions and the burial of hydrophobic residues from water and specific tertiary interactions, such as salt bridges, hydrogen bonds, the tight packing of side chains, and disulfide bonds. Protein folding occurs by creating non-covalent interactions that increase the stability of the protein. Protein folding and topology of a protein can be determined by x-ray crystallography, NMR, FRET, crosslinking studies, and additional techniques identifiable by a skilled person.

The term "express" as used herein in reference to "protein expression" indicates the production of a protein in a biological system associated with a stabilized tertiary and/or quaternary structure of the protein. "Heterologous expression" refers to the expression of a sequence in a host cell or environment, which does not naturally have the sequence. Insertion of the sequence (e.g. a gene or part thereof) in a heterologous host can be performed by recombinant DNA technology or other techniques identifiable by a skilled person.

The "expression level" used herein also refers to the quantity of recombinant protein production in a volume of a culture, on the single-cell level, or via other methods known to a person of ordinary skill in the art. Most recombinant protein production is achieved in heterologous hosts, namely the proteins are expressed in the cell lines or cell strains other than where they are produced in their native environments. For example, the origin of a recombinant protein may be mammals, such as human or mouse, and the heterologous hosts are organisms like $E.$ $coli$, yeast, or insects. The quantity of protein production can be measured in grams, milligrams, micrograms, moles, or other units understood by a person skilled in the art. A sufficient amount of protein will need to be produced and obtained in order to perform experimental studies.

The term "membrane protein" refers to a type of proteins that interact with or are embedded within biological membranes. The membrane proteins can be classified into two broad categories, integral membrane proteins (herein also IMPs) and peripheral membrane proteins.

The term "integral membrane protein" "IMP" or "transmembrane proteins" as used in the present disclosure indicate a protein including at least one transmembrane domain (TMD) which indicates any protein segment which is thermodynamically stable in a membrane, as will be understood by a skilled person. Accordingly, the integral membrane proteins have one or more segments that are embedded in the phospholipid bilayer. In particular, in integral membrane proteins a TMD is typically formed by a single transmembrane alpha helix. "Alpha helical membrane protein" indicates a membrane protein with at least one alpha helical TM.

Most integral membrane proteins contain residues with hydrophobic side chains that interact with fatty acyl groups of the membrane phospholipids, thus anchoring the protein to the membrane. Many integral membrane proteins span the phospholipid bilayer and contain one or more membrane-spanning domains extending into the aqueous medium on each side of the bilayer. The membrane-spanning domains are generally α helices or multiple β strands. The peripheral membrane proteins do not interact with the hydrophobic core of the phospholipid bilayer. Instead, they are usually bound to the membrane indirectly by interactions with integral membrane proteins or directly by interactions with lipid polar head groups.

In embodiments herein described, various features, both protein and nucleotide, can be calculated for those sequences in order to create statistical models of protein expression.

The term "feature" refers to a numerical value computed from nucleotide or protein sequence to capture a biological principle, process, or phenomenon. Features can be calculated over the entire sequence, some specific portion, or across windows in the sequences. Features can use summary statistics, e.g. mean, median, mode, standard deviation. Any embodiment of this invention will use window sizes and length as well as summary statistics interchangeably.

The term "model" as used herein refers to an algorithm that can be used to predict if an input set of characteristics is likely to possess a further characteristic and is generally referred to as supervised learning. In these examples, nucleotide and protein features are comprise the set of input characteristics, and expression level is the further characteristic to be predicted. The model for an expression level can be numeric (e.g. GFP fluorescence, level of Coomassie Blue stating) or binary (e.g. positive expression vs. negative expression via an arbitrary experimental measure).

The term "supervised learning" as used herein refers to an algorithm that infers a function or value of an item by comparing it to previously labeled training data formed in a model. The training data consists of an input object or vector, and an output value or function.

The term "support vector machine" (or "SVM") as used herein describes a specific type of a model that is generally described as partitioning of an N-dimensional space into regions separated by one or more hyperplanes. Given this model, new data (not yet categorized) can be determined, statistically, to be more or less likely to be in a given category based on that data's position in the space relative to the hyperplane. Various modifications include a soft-margin hyperplane, preference ranking, and others as known to a person of ordinary skill in the art.

The term "neural network" as used herein describes a specific type of a model that generally refers to a network of functions, each defined as compositions of other functions. In a probabilistic view, it is a network of interdependent random variables. Given a particular task to solve and a particular class of functions, neural network learning consists of using a set of observations to solve the task in an optimal way (although, not necessarily in the most optimal way).

The term "decision tree" as used herein describes a specific type of model that generally maps observations about something (branches of the tree) to conclusions about that thing's value (leaves of the tree). If the values are non-discrete (e.g. real numbers), the tree is referred to as a "regression tree".

Generally, the statistical approach to membrane protein expression prediction is through calculating features from the nucleotide and protein sequence and then performing statistical modelling on those features in relation to expression levels. This can be done to enrich a set of targets for expression and to design protocols to enrich for protein expression.

Enriching Targets

The process for enriching the set of targets for expression can be further broken down, for example, in:
1) selecting an initial set of sequences having known protein expression levels;
2) transforming the initial set of sequences into features (nucleotide and/or protein features);
3) dividing the initial set of sequences into two or more subsets, with at least one training set and at least one test set;
4) creating a model (supervised learning algorithm) based on the training set—the data points for the model being the pairing of features and expression level of each member of the set;
5) testing the model with the one or more test sets, to see if the prediction of expression levels matches the model (and is better than random selection); and
6) when an acceptable model is produced (based on the testing), using the model on a further set of sequences (a "distinct set"—being separate from the initial set) where the expression level is, at that time, untested/unknown to the user—the model providing predictions of the expression levels of the further sequences based on their calculated features.

With the predicted expression levels of the further set of sequences, the user can then select from the further set, a subset ("positive result set") of best-performing (i.e. positive expression—a subset with the highest expression levels) sequences for experiments to determine actual expression levels and, thereby, determine which sequences to use for membrane protein expression.

Design Protocols

The process to design protocols to enrich for protein expression can be further broken down to:
1) selecting a membrane protein of interest (just as the "enriching the set of targets for expression" case above);
2) identifying expressed similar proteins in a plurality of different conditions (protocols);
3) then, for each of those conditions:
    a) selecting an initial set of sequences with known protein expression for a membrane protein,
    b) transforming the initial set of sequences to features (nucleotide and/or protein features, as in the "enriching the set of targets for expression" case above),
    c) dividing the initial set of sequences into training set(s) and test set(s) (as in the "enriching the set of targets for expression" case above),
    d) creating a model based on the training set, the model providing statistical analysis of expressing the membrane protein and validating the model with the test set (as in the "enriching the set of targets for expression" case above—but now there are different models for each condition); and
4) determining which of the conditions has a best predictive performance (predicting expression levels based on features) based on the validation results for each of the conditions.

Once the best performing conditions have been determined, membrane protein expression experiments can be performed on the membrane protein of interest under those best conditions, thereby providing better overall results for protein expression prediction.

Both processes can be performed where the sequences (initial set and/or distinct set) are alpha-helical membrane proteins, with either single or multiple transmembrane domains.

In some embodiments, polynucleotides encoding a membrane protein of interest identified from the methods and systems herein described can be cloned using commercially available reagents from vendors such as QIAGEN™, Invitrogen™, Applied Biosystems™, Promega™, and others, following standard molecular biology methods known to a person of ordinary skill in the art. For example, polynucleotides encoding the membrane protein of interest can be cloned into an expression vector. Expression vectors can comprise plasmid DNA, viral vectors, or non-viral vectors, among other known to those skilled in the art, comprising appropriate regulatory elements such as promoters, enhancers, and post-transcriptional and post-translational regulatory sequences, as would be understood by a skilled person.

Cloned recombinant proteins can be expressed using cell-based methods, or cell-free methods, following standard techniques and using commercially available kits. Cell-based methods for expression of recombinant proteins can include expression in prokaryotic or eukaryotic cell cultures, such as *E. coli* or other bacterial cells, yeast strains, insect cells or mammalian cells, among others known to those skilled in the art.

Both processes can transform features using methods such as scaling, centering, PCA, autoencoding, and/or discretization.

Both processes can utilize features that can be described by, for example, overall codon usage, codon pair score, tRNA adaptation index, 5' codon usage, GC content, 5' RNA structure, overall RNA structure, Shine-Dalgarno-like sites, overall disorder, loop disorder, TM size/count, hydrophobicity, loop charge, loop length, length/pI, and/or others.

The method of identifying similar proteins can be performed by sequence-based or structure based methods.

The conditions can include, for example, expression host, host strain, plasmid, growth temperature, growth medium composition, expression tags, linker regions, purification affinity methods, solubilization methods, and detection methods.

The models can use a supervised-learning statistical framework, such as SVM, neural networks, decision trees, or others.

Comparison of Techniques

An example of the benefit of a statistical approach to membrane protein expression prediction is shown in FIG. 1. Given a set of homologs (100) with 20% of the homologs expressing a protein of interest (110) and 80% having negative expression (105), a problem exists in selecting which to test for expression. The ideal situation (135) would be to only select those sequences that provide expression (140). However, if the sequences have not yet been tested, then the only way to do that would be to have a complete understanding of the relationship between sequence and expression, which has not yet been and may never be achieved. What is done in practice is to select a random assortment of the sequences (115), as many as time and budget will allow, and test that subset (120). Since the selection is random, the percentage of positive results for expression will, on average, be the same as the percentage of expressing sequences in the original set (100), in this case 20%. However, using an embodiment of this invention (125) in determining what sequences to include in the subset (130) will, on average, give a percentage of positive results greater than what is expected from random selection. This provides a cost-benefit to the process of executing membrane protein expression, as the ratio of success to experimental tests is increased.

Detailed characterization (e.g. atomistic structure) of biological macromolecules requires a large mass of the molecule—typically only achievable through heterologous expression in a recombinant host. The process of finding or engineering a target for large-scale expression is tedious often requiring a long trial and error process and, in the process, consumes significant financial and human resources. Integral membrane proteins (IMPs), proteins that span cellular membranes, broadly compose around one-third of genomes and substantial number of drug targets, yet their structural characterization lags that of other (i.e. soluble) proteins. By and large, this is due to the difficulty IMP targets pose in heterologous expression (the first step towards characterization).

In particular, an appropriate weighting of parameters calculated from sequences (nucleotide and/or protein) produces a score that relates to the likelihood that a given IMP will be successfully expressed. For example, some embodiments of this invention show that selecting proteins with high scores results in 4-6 successful outcomes per 10 tested where, previously, only 1 or 2 would be successful on average, representing a tremendous increase in efficiency (see FIG. 1). In alternative embodiments, changing or retraining the model that maps between sequence features and expression score shows further improvement.

Ideally, of course, it would be preferable to find a 100% mapping between sequence feature and level of expression. However, attempts in this direction have, so far, been unsuccessful as the biological processes that connect the features to level of expression are not yet fully understood, and might never be. The statistical approach provides a compromise position such that, while still typically providing less than 100% true-positive selection, it typically provides a significantly higher true-positive percentage than what would have been selected at random (see FIG. 1).

Example use-case: Given a specific G-Protein Coupled Receptor (GPCR) of biomedical interest, one important task is finding pharmaceutical drugs to modulate its activity. To do so, the first step is producing the protein to high yield, e.g. purified protein for structure based drug discovery or drug screening. Previously, a research team would select N homologous targets (as permitted by their budget) out of typically 100-1000s in the genome databases, but they would find that only some small fraction (in the range of what would be expected with random chance) is able to be expressed, with the rest representing wasted time and money. By using an embodiment of this invention, the research team would instead the select a fewer number of the highest scoring targets (again of the 100-1000s) and would find that a greater proportion are expressed, i.e. better than random. In the process, man-hours and monetary expenditure are significantly reduced since fewer targets require testing and the targets tested are more frequently successful.

Sequencing

In some embodiments, polynucleotide sequences are obtained through next-generation sequencing (NGS), also known as high-throughput sequencing. NGS is a term used to describe a number of different modern nucleic acid sequencing technologies including Illumia™ sequencing, Roche 454™ sequencing, Ion torrent: Protein/PGM™ sequencing and SOLiD™ sequencing. Next-generation sequencing (NGS) generally refers to non-Sanger-based high-throughput DNA sequencing technologies. The NGS technologies can be based on immobilization of the nucleotide samples onto a solid support, cyclic sequencing reactions using automated fluidics devices and detection of molecular events by imaging. Cyclic array platforms achieve low costs by simultaneously decoding a two-dimensional array bearing millions or billions of distinct sequencing features, each containing one species of DNA physically immobilized on an array. In each cycle, an enzymatic process is applied to interrogate the identity of a single base position for all features in parallel. The enzymatic process is coupled to either the production of light or the incorporation of a fluorescent group. At the end of each cycle, data are acquired by imaging of the array. Subsequent cycles are typically performed interrogating different base position within the sequence. Detailed information about various next-generation sequencing approaches can be found in related literature and documents and will be understood by a person skilled in the art.

The sequencing approaches herein described can produce a sequence file typically in text-based format such as a plain sequence format, a FASTQ format, a FASTA format, an EMBL format, and other formats identifiable to a skilled person in the art. These sequence files can contain one or more nucleotide sequences, its identification number, and corresponding quality scores as well as some annotation information in some data formats, which can be used later for sequence analysis. These sequence files can be used as input files for calculating relevant features illustrated in FIG. 2.

In some embodiments, the methods and systems herein described comprise collecting raw data of a plurality of membrane proteins and/or polynucleotides and calculating sequence features from the collected sequence data. In particular, for each membrane protein and/or polynucleotide being collected, the raw data contains a sequence data, i.e. the order of the amino acids in a protein or the order of the four bases in a polynucleotide, and an expression level associated with the sequence.

Expression Levels

The membrane protein and/or polynucleotide sequences with known expression levels can be collected from various sources. For example, the sequence data with known expression levels can be identified and collected from publications (see Examples section) with the sequences mapped and retrieved from public databases such as the National Center for Biotechnology Information (NCBI) using the sequences' identification number, such as the G.I. or accession number, or other characteristics as known to a person of ordinary skill in the art. The sequence data can also be collected from established databases such as New York Consortium on Membrane Protein Structure (NYCOMPS) Data which also includes expression outcomes in various experimental conditions. Other consortium facilities and databases for collecting the sequence data include, for example, the Center for Structures of Membrane Proteins (CSMP), Membrane Protein Structural Biology Consortium (MPSBC), and GPCR Network (GPCR); a current list be found at http://sbkb.org/tt/centers.html., as will be understood by a skilled person in the art.

Features

The sequences data collected from the various sources can then be curated with particular sequence features calculated to capture an ensemble of biological principles, processes, or phenomena. In one exemplary embodiment shown in Table 1, the calculated sequence features, are categorized into several categories as shown in column "Category" of Table 1. The features of polynucleotide sequences can be categorized into categories including overall codon usage, codon pair score, tRNA adaption index, 5' codon usage, GC content, 5' RNA structure, overall RNA structure, Shine-Dalgarno-like sites, or others identifiable by a skilled person in the art. The features of protein sequences can be categorized into categories including overall disorder, loop disorder, TM size/count, hydrophobicity, loop charge, loop length, length/pI, or others identifiable by a skilled person in the art. In one exemplary embodiment shown in Table 1, categories are shown in column "Category" of Table 1. Any embodiment of this invention will include features from one or more categories.

The category "overall codon usage" refers to codon usage analysis in general, in which a codon is a series of three nucleotides (a triplet) that encodes a specific amino acid residue in a polypeptide chain or for the termination of translation (stop codons). Exemplary features calculated in this category include, for example, codon adaption index ("CAI"), effective number of codons ("Nc"), GC content at the synonymous position ("GC3s"), and frequency of CG di-nucleotides ("CpG"), as shown in column "Calculation Method/Tools" of Table 1.

Additional codon usage metrics can include: Relative synonymous codon usage (RSCU), overall codon usage, amino-acid usage, base composition in each reading frame, base composition of synonymous third codon positions, dinucleotide frequencies, frequency of optimal codons, codon bias index, and effective number of codons. As used herein, the codon adaption index is a measurement of the relative adaptiveness of the codon usage of a gene towards the codon usage of highly expressed genes. The effective number of codons is a measure of overall codon bias. The GC content refers to the frequency of nucleotides that are guanine or cytosine. The GC content at the synonymous positions refers to the fraction of codons that are synonymous at the third codon position which have either a guanine of cytosine at that third codon position. The above features can be calculated using software such as codonW or other similar codon usage analysis software identifiable to a person of ordinary skill in the art.

The category "codon pair score" refers to particular features calculated to quantify occurrences of a given codon-pair as well as codon-pair bias. A codon pair refers to two neighboring codons encoding a pair of amino acid residues. "tRNA adaptation index" refers to a tRNA-centric measure of translation efficiency. "5' codon usage" features the codon usage analysis of the codons near the 5' end of the polynucleotides, such as the first 10-40 codons of the 5' end. The "GC content" category calculates the percentage of nitrogenous bases on a DNA or RNA molecule that are either guanine or cytosine. The GC content of a polynucleotide can be calculated over the entire sequence of the polynucleotide as the overall GC content or over a portion of the polynucleotide such as a number of codon windows.

The "overall RNA structure" features are derived from the analysis of nucleic acid structures and calculations of relevant structures, e.g. minimum free energy. The "5' RNA structure" features the RNA structure analysis of the sequence near the 5' end of the RNA. The 5' end can include 5' non-coding elements of variable length, e.g. 5, 10, 15, bases into the sequence. Exemplary features in this category include the ΔG of the lowest free energy structure ("deltaG"), frequency of the lowest free energy structure within the ensemble ("freqens"), average hybridization probability over 10 base windows ("avgRNAss"), and others as shown in Table 1. The above RNA structure features can be calculated using software RNAfold, NUPACK, or other similar RNA structure analysis software identifiable by a person of ordinary skill in the art.

"Shine-Dalgarno sequence" is a ribosomal binding site in bacterial and archaeal mRNA, generally located around 8 bases upstream of the start codon AUG (i.e. in the 5' untranslated region of mRNAs). Translation initiation typically depends on complementary binding between the Shine-Dalgarno ("SD") sequence and the complementary anti-Shine-Dalgarno ("anti-SD") sequence on the 3' tail of the 16S ribosomal RNA. The strength of the SD site can be used as a feature.

The "Shine-Dalgarno-like sites" category used herein refers to sequence sites in the coding region having a sequence similar to the Shine-Dalgarno sequence. In some cases, the Shine-Dalgarno-like sites can generate programmed ribosomal pauses that on one hand are beneficial for protein folding or accurate targeting and on the other hand reduce protein production. Exemplary features calculated in this category include total number of SD-like sites of the entire sequence or a portion thereof, such as between codons 16 and 36, codons 40 and 60, or in the region starting 5 residues before and ending 2 residues after the start of the $2^{nd}$ transmembrane domain, as well as average anti-SD-SD hybridization energy for the whole protein or a portion thereof, such as between codons 16 and 36, between codons 40 and 60, or between 5 codons prior to and 2 codons after the start of the $2^{nd}$ TM segment. Other methods of capturing SD/ribosomal binding sequence hybridization are known in the art.

The "overall disorder" represents a category of features related to disordered/unstructured regions within a protein sequence. An exemplary feature calculated in this category includes the number of "hot" loops, which are classified as highly dynamic based on $C_\alpha$ temperature. Avoiding disordered segments in protein expression constructs can enhance foldability and stability of the expressed protein. Tools such as RONN, DisEMBL, GlobPlot, and DISOPRED2 can be used for such calculations.

The "loop disorder" category represents features related to natively disordered regions in proteins, such as loop regions, and the likelihood of disorder based on the calculated scores. For example, disorder prediction tools such as RONN, DisEMBL, and MetaDisorder can be used to calculate a disorder score for the entire protein, TM segments, or various loop regions.

The "TM size/count" category represents features related to the TM region. Exemplary features include the average length of TM segments, number of residues predicted to be part of a TM segment and the proportion of the TM segment versus the entire protein.

The "hydrophobicity" refers to a physical property of a protein to be unattractive to water. Exemplary hydrophobicity features include an averaged value calculated for the entire protein or a relevant portion thereof such as the TM segment or the loops.

The "loop charge" refers to charge calculations on loops or terminal regions of a protein. Exemplary features include the total positive and negative charges on cytoplasmic or extracellular loops. The "loop length" refers to length calculations on loops or terminal regions of a protein. Exemplary features include lengths of extracellular and cytoplasmic loops as well as loops between particular TM segments. The "length/pI" refers to features that correspond to the protein length, i.e. number of residues of a protein, molecular weight as well as isoelectric point for the entire protein, or a relevant portion thereof.

Transforming Sequence Information into Input Space

Natively, membrane proteins are variable length strings (with a specific nucleotide/protein alphabet) (601, 602) (SEQ ID NO: 1 and SEQ ID NO: 2). This structure of information (unstructured, in fact) is not amenable to being characterized statistically. Instead, the sequences can be transformed into a structured input space where any membrane protein can be expressed in along the dimensions of that space.

To do so, a set of biological parameters that likely describe membrane protein and their biogenesis can be determined, and software code (603, 604) can be used to calculate relevant information. Any unstructured output (605, 606, 607, 608) can be reduced (609) into numerical features (610). An example list of categories and features can be found in Table 1. The individual features themselves are not as important as the ensemble coming together, in terms of what enables prediction. Any implementation for membrane protein expression prediction can use features from one or more of the categories described. Code can be generated, or obtained by a third party source, to provide the data in an acceptable way and then parse the output into features, or to condense the output data into features.

TABLE 1

Sequence parameter weights and descriptions

| Type | Category | Abbreviation | Description |
|---|---|---|---|
| Nucleotide | Overall | CAI | Codon Adaptation Index |
| | Codon usage | Nc | Effective number of codons |
| | | GC3s | GC content at the synonymous position |
| | | CpG | Frequency of CG di-nucleotides |
| | | avgCU | Average Codon Usage |
| | Codon Pair Score | CPS | Sum of Codon Pair Score values |
| | | CPSpL | Codon Pair Bias |
| | tRNA adaptation index | tAI | tRNA Adaptation Index |
| | | tAI10Min | Minimum tAI score over 10 codon windows |
| | | tAI10Max | Maximum tAI score over 10 codon windows |
| | | tAI10q25 | $25^{th}$ percentile of tAI scores over 10 codon windows |
| | | tAI10q75 | $75^{th}$ percentile of tAI scores over 10 codon windows |
| | 5' Codon Usage | avgCU_first40 | Codon Usage over the first 40 codons |
| | | avgCU_first20 | Codon Usage over the first 20 codons |
| | | avgCU_first5 | Codon Usage over the first 5 codons |
| | | avgCU_first10 | Codon Usage over the first 10 codons |
| | GC content | GC | Overall GC content |
| | | GC10min | Minimum % GC over 10 codon windows |
| | | GC10q25 | $25^{th}$ percentile of % GC over 10 codon windows |
| | | GC10q75 | $75^{th}$ percentile of % GC over 10 codon windows |
| | | GC10max | Maximum % GC over 10 codon windows |
| | 5' RNA Structure | X40deltaG | ΔG of the lowest free energy structure for the first 40 codons |
| | | X40freqens | Frequency of the lowest free energy structure within the ensemble for the first 40 codons |
| | | plus10valRNAss | Average hybridization probability centered around +10 base, i.e. average of +5 to +15 (Goodman, et al., 2013) |
| | | zeroto38avgRNAss | Average hybridization probability over 10 base windows from 0 to +38 |
| | | zeroto38minRNAss | Minimum hybridization probability over 10 base windows from 0 to +38 |
| | | zeroto38q25RNAss | $25^{th}$ percentile of hybridization probability over 10 base windows from 0 to +38 |
| | | zeroto38q75RNAss | $75^{th}$ percentile of hybridization probability over 10 base windows from 0 to +38 |
| | | zeroto38maxRNAss | Maximum hybridization probability over 10 base windows from 0 to +38 |
| | Overall RNA structure | deltaG | ΔG of the lowest free energy structure |
| | | freqens | Frequency of the lowest free energy structure within the ensemble |
| | | avgRNAss | Average hybridization probability over 10 base windows |
| | | minRNAss | Minimum hybridization probability over 10 base windows |
| | | q25RNAss | $25^{th}$ percentile of hybridization probability over 10 base windows |
| | | q75RNAss | $75^{th}$ percentile of hybridization probability over 10 base windows |
| | | maxRNAss | Maximum hybridization probability over 10 base windows |

TABLE 1-continued

Sequence parameter weights and descriptions

| Type | Category | Abbreviation | Description |
|---|---|---|---|
| | Shine-Dalgarno-like sites | totalSDsites | Total number of Shine-Dalgarno (SD)-like sites |
| | | relareaSD | Average anti-SD - SD hybridization energy for the whole protein |
| | | codon16_36SD | Total number of SD-like sites between codons 16 and 36 |
| | | codon16_36relareaSD | Average anti-SD - SD hybridization energy between codons 16 and 36 |
| | | codon40_60SD | Total number of SD-like sites between codons 40 and 60 |
| | | codon40_60relareaSD | Average anti-SD - SD hybridization energy between codons 40 and 60 |
| | | −5_+2TM2SD | Total number of SD-like sites lying in the region starting 5 residues before and ending 2 residues after the start of the $2^{nd}$ transmembrane domain |
| | | −5_+2TM2relareaSD | Average anti-SD - SD hybridization energy between 5 codons prior to and 2 codons after the start of the $2^{nd}$ TM segment |
| Protein | Overall Disorder | hotloops | Number of "hot" loops, which are classified as "highly" dynamic based on $C_\alpha$ temperature, minus 1 |
| | Loop Disorder | avgRONNTM | Average RONN score for TMs |
| | | avgRONN | Average RONN score for the entire protein |
| | | q25RONN | $25^{th}$ percentile of RONN scores |
| | | q75RONN | $75^{th}$ percentile of RONN scores |
| | | avgRONNloop | Average RONN score of loops |
| | | avgRONNextloop | Average RONN score of extracellular loops |
| | | avgRONNcytloop | Average RONN score of cytoplasmic loops |
| | | avgRONNNterm | Average RONN score of the N-terminus, i.e. loop that precedes the first TM segment |
| | | avgRONNCterm | Average RONN score of the C-terminus, i.e. loop that follows the final TM segment |
| | | avgRONNTM1_2 | Average RONN score for the loop between the first 2 TM segments |
| | | RONNlongestloop | Average RONN score for the longest loop |
| | TM Size/Count | avgTMlen | Average length of TM segments |
| | | membrCont | Number of residues predicted to be part of a TM segment |
| | | membrContNorm | MembrCont/length of protein |
| | Hydrophobicity | avgHydroGES | Average hydrophobicity (GES scale as in Daley, et al., 2005) |
| | | minhyd_19GES | Minimum hydrophobicity over 19 residue windows |
| | | minhyd_41GES | Minimum hydrophobicity over 41 residue windows |
| | | maxhyd_41GES | Minimum hydrophobicity over 41 residue windows |
| | | nterm_hydOCT | Average hydrophobicity of the N-terminus |
| | | loop1_avghydOCT | Average hydrophobicity of the first loop (Octanol-water partitioning scale) |
| | | loop1_minhyd_OCT19 | Minimum hydrophobicity of 19 residue windows |
| | | loop1_maxhyd_OCT19 | Maximum hydrophobicity of 19 residue windows |
| | | HYD1stTM | Hydrophobicity of the first TM segment |
| | | HYDallTMs | Average hydrophobicity of all TM segments |
| | | delG1stTM | ΔG of insertion of the $1^{st}$ TM segment |
| | | delGallTMs | Average ΔG of insertion of all TM segments |
| | | aromatacityNorm | Average aromaticity |
| | | GPcount | Total number of glycines and prolines in TMs/number of TMs |
| | Loop charge | numPosCyt | Total (−) charges (R, K, H) on cytoplasmic loops |
| | | numPosNormCyt | numPosCyt/the total cytoplasmic loop length |
| | | numNegCyt | Total (+) charges (E, D) on cytoplasmic loops |

TABLE 1-continued

Sequence parameter weights and descriptions

| Type | Category | Abbreviation | Description |
|---|---|---|---|
| | | numNegNormCyt | numNegCyt/the total cytoplasmic loop length |
| | | numPosExt | Total (+) charges (R, K, H) on extracellular loops |
| | | numPosNormExt | numPosExt/divided by the total extracellular loop length |
| | | numNegExt | Total (−) charges (E, D) on extracellular loops |
| | | numNegNormExt | numNegExt/the total extracellular loop length |
| | | numPos_LongestCytLoop | Total (+) charges (R, K, H) on the longest cytoplasmic loop |
| | | nterm_neg | Total (−) charges (E, D) on the N-terminus |
| | Loop length | len1_2loop | Length of the loop between the first two TM segments (Fluman, et al., 2014) |
| | | longestCytLoopNorm | Length of the longest cytoplasmic loop divided by the length of the protein |
| | | longestExtLoop | Length of the longest extracellular loop |
| | | longestExtLoopNorm | Length of the longest extracellular loop divided by the length of the protein |
| | | lenNterm | Length of N-terminus |
| | | lenNtermNorm | LenNterm/length of protein |
| | Length/pI | seqLen | Protein length, i.e. number of residues |
| | | weight | Molecular weight |
| | | pI | Isoelectric point |

Finding Likely Sequences from a Set

Figure 2:
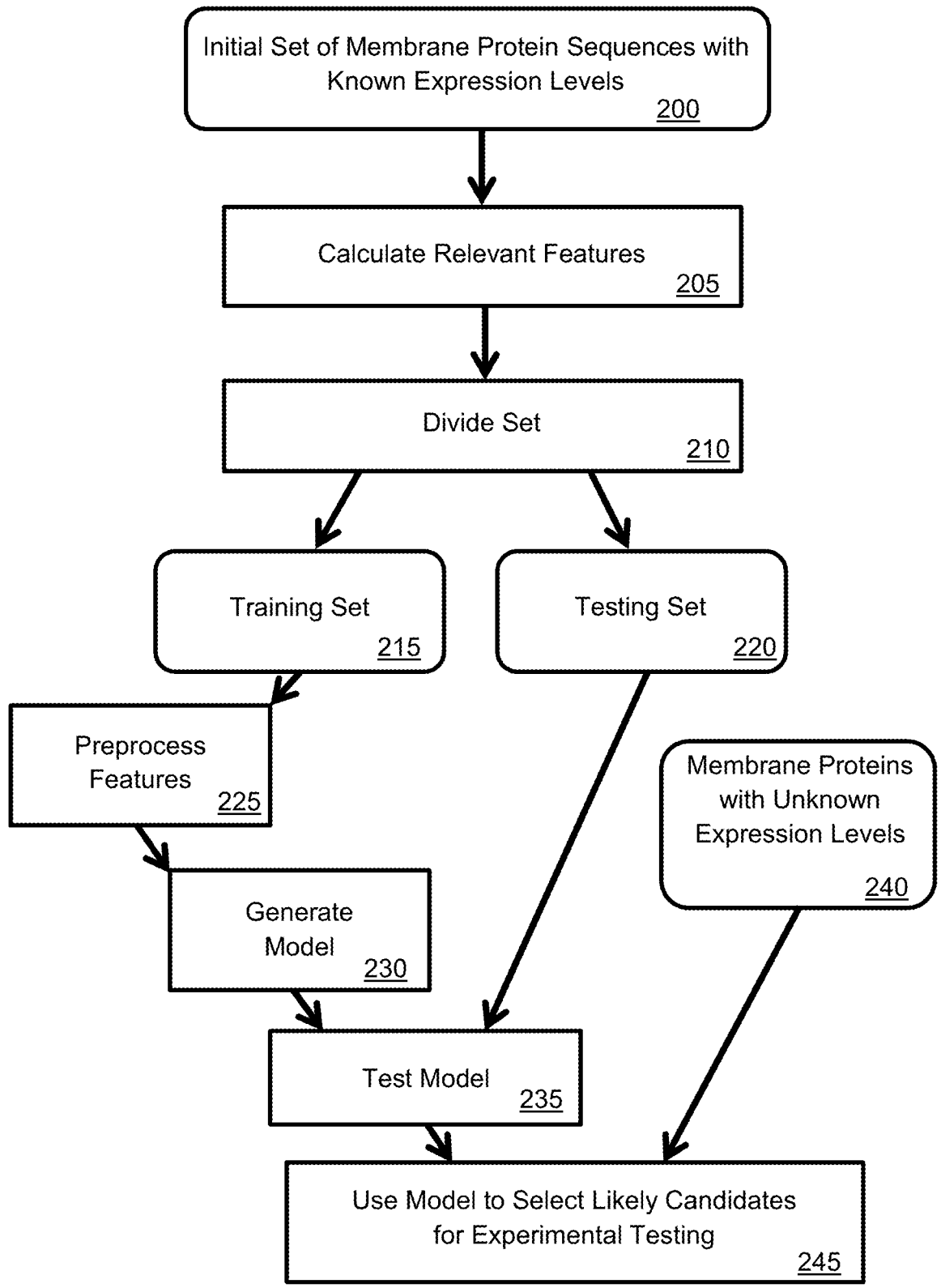
FIG. 2 shows a flowchart for an exemplary method, for selecting candidates for experimental testing for protein expression.

FIG. 2 generally shows an example flowchart to improve selections from a set of membrane proteins with unknown expression levels. First, an initial set of membrane protein sequences with already known (e.g. from experimentation or from a database) expression levels (200) is gathered.

Using detailed biophysical analysis and/or anecdotal evidence, select a range of different protein and nucleotide sequence features that are considered relevant to expression level. Calculate, in software, (205) these features for the given initial set of membrane protein sequences.

The calculated set is then divided (210) into a training set (215) and a test set (220). The division can be done by any algorithm, including random selection, and in any ratio (e.g. 75% training/25% test). However, it is usual to have a larger training set than testing set. Alternatively, the set can be split into multiple groups of the same size (e.g. 10) and then training on all but one and testing on one.

The training set can be preprocessed (225) for machine learning using methods known to a person of ordinary skill in the art. This can include "centering" and "scaling" the data. "Centering" can be done by subtracting from each data point the mean value of the corresponding feature, and "scaling" can be done by dividing each data point by a standard deviation of the corresponding feature. This can also reduce the number of features to a combination that hold most of the information. Techniques to do this include principal component analysis ("PCA") by retaining dimensions with the highest N % variance, typically 95%, removing linear combinations of features, and removing highly correlated features. Another exemplary technique is feature discretization, i.e. turning numerical features into quantiles each becoming a new dimension.

A model is then created (230). In one embodiment, creating a model means to a) select a statistical framework, where the statistical framework is defined by a mathematical equation having free parameters and a cost function, and b) set the free parameters to minimize the differences between known outcomes in the training set and predicted outcomes from the statistical framework. There are an almost innumerable number of statistical frameworks that can be used at this stage; some examples include standard neural networks, decision trees, random forests, weak learning methods (e.g. stochastic gradient boosting), and support vector machines. For some statistical frameworks, the framework can be "tuned", i.e. regularized to avoid problems such as overfitting the data, by the use of "hyperparameters". For example, a statistical framework can be trained against raw data over a grid of candidate hyperparameter values, and then each candidate framework is evaluated against a subset of the training data. The model can be selected as the statistical framework with hyperparameters yielding the lowest error.

More generally, any supervised-learning statistical framework can be used. Overall, an embodiment of this invention requires the steps of 1) determining the type of training examples, 2) gathering a training set of data, preferably one that is representative of the real-world use of the function to be modeled, 3) determining the input feature representation of the learned function, 4) determining the structure of the learned function and corresponding learning algorithm, 5) creating a model by running the learning algorithm on the training set, and 6) evaluating the accuracy of the model by running a test set on the model that is separate from the training set. There are a number of supervised learning algorithms available to use for creating the model, and there is no single learning algorithm that works best for all supervised learning problems. Supervised learning methods include support vector machines, neural networks, and decision trees, and others as known to a person of ordinary skill in the art.

The model can then be tested (235) with the previously set-aside test set (220). If the performance of the model is acceptable (e.g. providing a true-positive result sufficiently above random to provide an economic advantage), then the model can be retained. If not, then it can be discarded, and the method can be returned to any previous point and re-attempted with different features, known expression data, train-test splitting, preprocessing methods, or statistical frameworks.

As used herein, "economic advantage" refers to any advantage that would make the activity more worthwhile, such as lower financial costs, reduced work-hours, reduced input requirements, or higher output throughput.

A retained model can then be used to select likely candidates (245) for experimental testing/verification out of sets of membrane protein sequences (240) with unknown expression levels.

Figure 4:
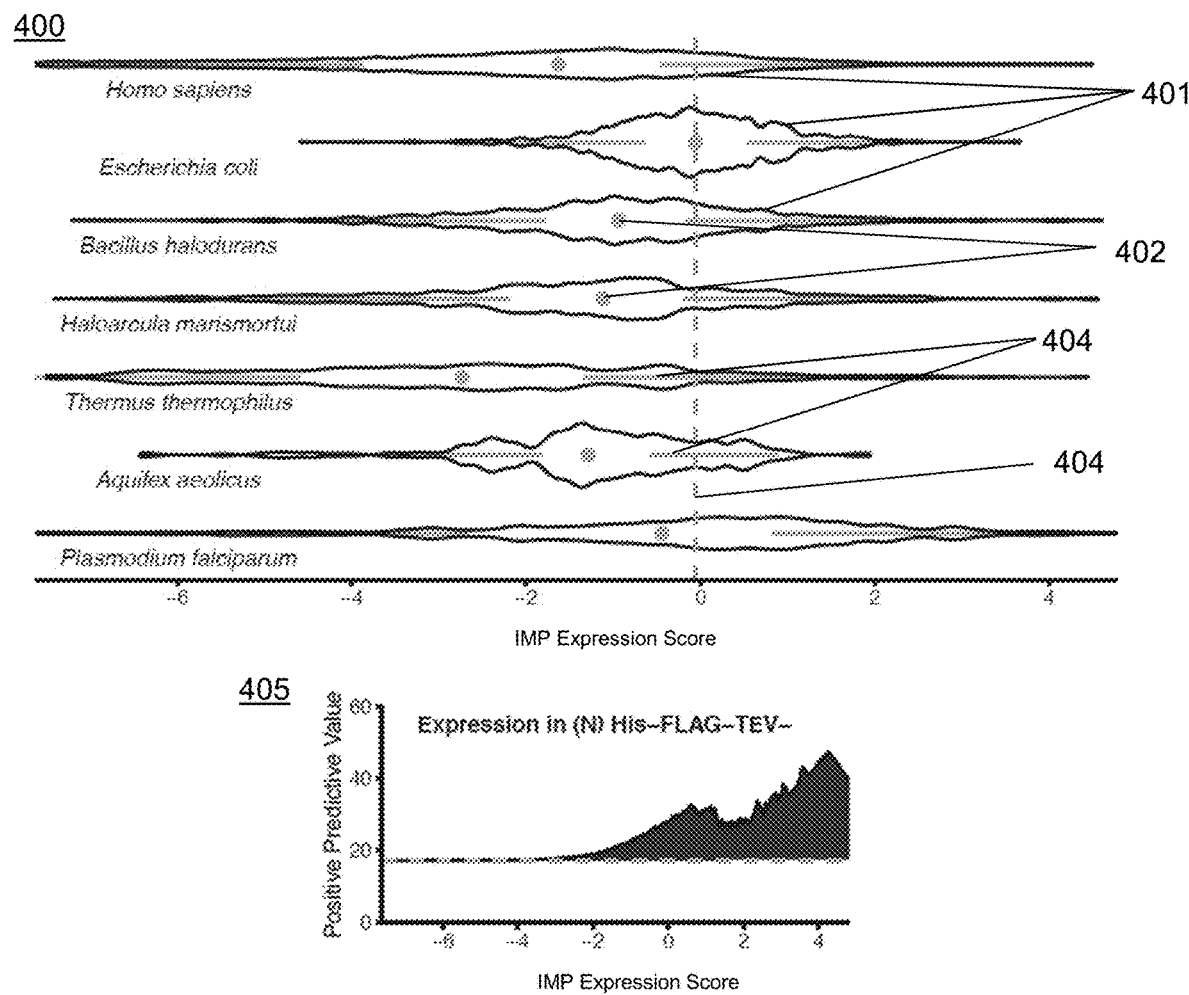
FIG. 4 shows example charts depicting example forward predictions of membrane protein expression from various genomes.

FIG. 4 shows usage of one embodiment of this invention. IMP expression scores are calculated for membrane proteins from a variety of genomes (400). Contours (401) are calculated by a kernel density estimate of the number of proteins at a given score. Width is only relative within a genome. The central point (402) represents the median of the distribution and the horizontal lines (403) represent the quantities of an analogous Tukey boxplot. The vertical dashed line (404) is plotted at the 50th percentile score in E. coli to provide context for other distributions. Proteins at high score (to the right) are candidates with likely high expression levels that used for experimentation. The positive predictive value $$\frac{TP+FP}{TP}$$

of the algorithm within the most tested NYCOMPS vector vs IMP expression score shows that the model is successful at capturing known outcomes (405).

Finding the Best Environments/Conditions

In some embodiments, the methods and systems herein described can be used to design for optimal membrane protein expression conditions. The yield of membrane proteins expressed in heterologous expression systems is limited by the capability of the heterologous host to import additional proteins or replace its own proteins within the cell membrane or subcellular compartments. Factors that can be manipulated to enhance membrane protein production include, for example, the selection of host strains, vectors, strength of transcriptional promoters, growth conditions such as temperatures, concentration and choice of inducers and buffers, choice of media and other factors known to a person of ordinary skill in the art of molecular biology.

Figure 3:
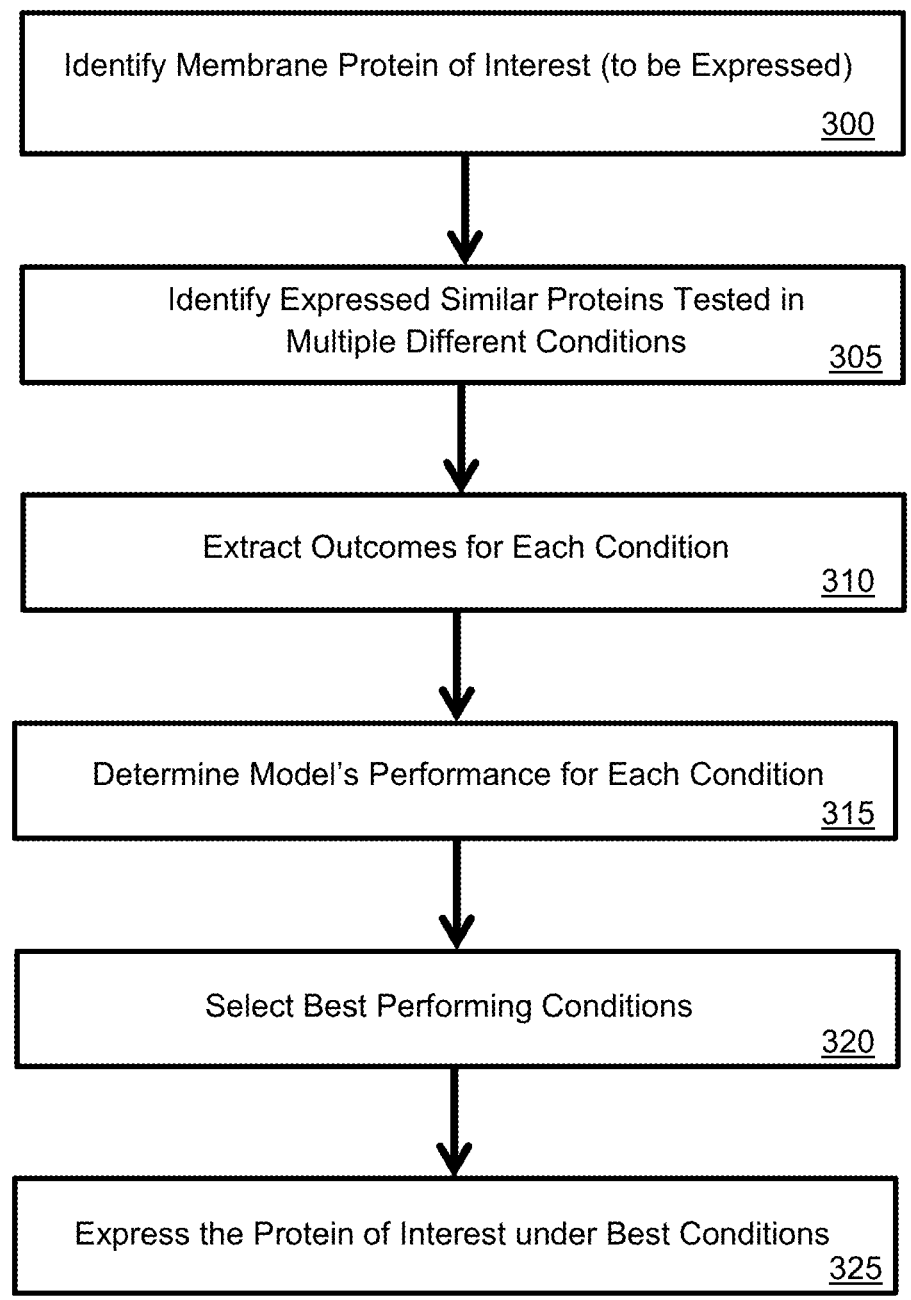
FIG. 3 shows a flowchart for an exemplary method, for selecting testing protocols for experimental testing for protein expression.
Figure 5:
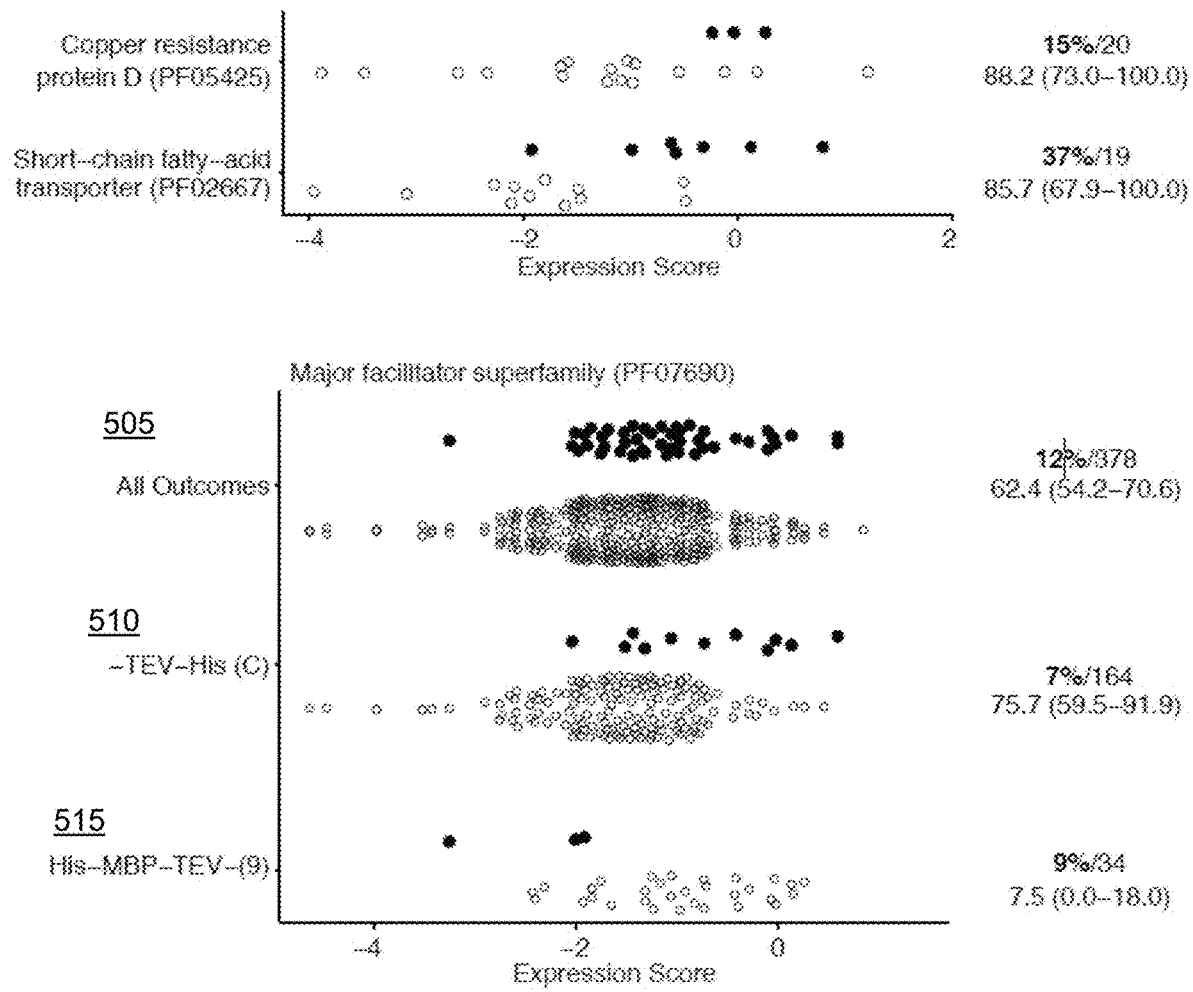
FIG. 5 shows example expression scoring for testing protocols.
Figure 6:
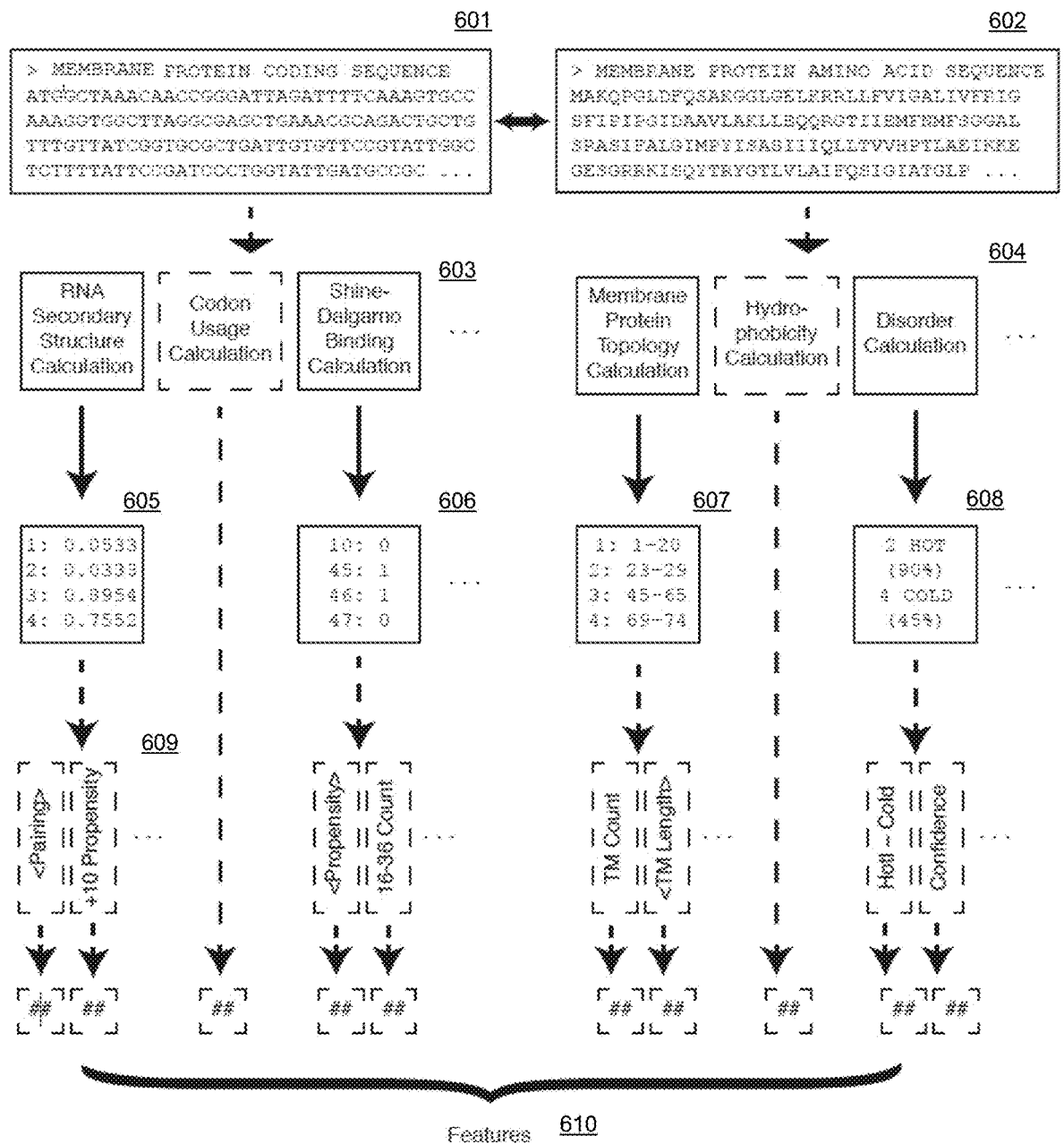
FIG. 6 shows an example of converting genome sequences 601 (SEQ ID NO: 1) and 602 (SEQ ID NO: 2) to quantitative features.

FIG. 3 generally shows an example flowchart of using an embodiment of this invention to improve experimental protocol. First, identify a membrane protein of interest to be expressed (300). For known expression trials for the particular membrane protein of interest (305), take the outcomes for each of the conditions from a database of expression trials (310). Then, use a previously generated statistical model, such as determined in the method shown in FIG. 2, and determine that model's performance independently for each condition (315). Then select the best performing condition or conditions (320) to use in expressing the membrane protein of interest (325), i.e. the protein should be expressed in the condition in which its score is among high scoring proteins, according to the model. In a specific embodiment of this invention, examples of some results for protocol expression are shown in FIG. 5. As shown for PF07690, subsets (510, 515) of the over-all outcome results (505) shows outcomes based on two different conditions, -TEV-His(C) (510) and His-MBP-TEV-(9) (515). The positive rate in each condition is about the same, but, as shown by the graph, -TEV-His(C) (510) is much more predictable by the model because it produces higher expression scores for the positives. Therefore, for any new protein of interest, it would be advantageous to express it in that condition if its score were −1 or higher (among the positives).

Hardware

Figure 7:
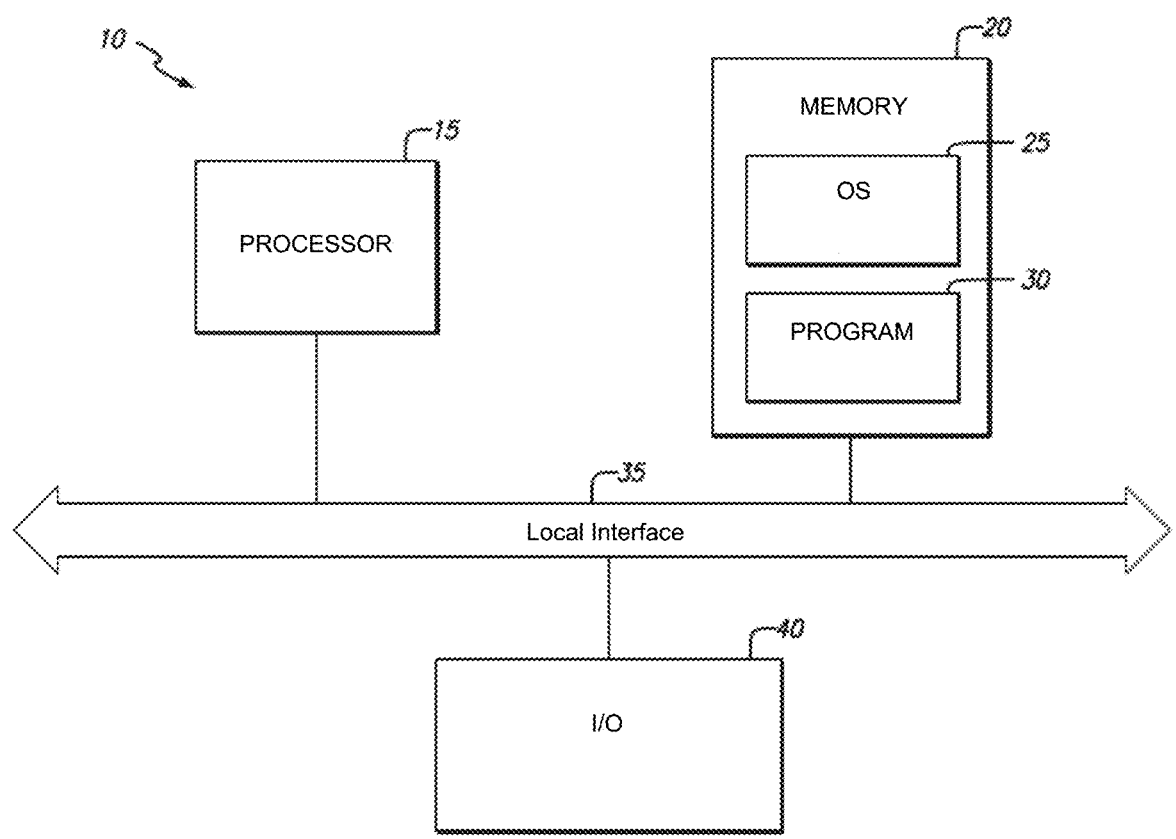
FIG. 7 shows an example hardware for carrying out the various methods.

FIG. 7 is an exemplary embodiment of a target hardware (10) (e.g., a computer system) for implementing the embodiment of FIGS. 1 to 6. This target hardware comprises a processor (15), a memory bank (20), a local interface bus (35) and one or more Input/Output devices (40). The processor may execute one or more instructions related to the implementation of FIGS. 1 to 6 and as provided by the Operating System (25) based on some executable program (30) stored in the memory (20). These instructions are carried to the processor (15) via the local interface (35) and as dictated by some data interface protocol specific to the local interface and the processor (15). It should be noted that the local interface (35) is a symbolic representation of several elements such as controllers, buffers (caches), drivers, repeaters and receivers that are generally directed at providing address, control, and/or data connections between multiple elements of a processor based system. In some embodiments the processor (15) may be fitted with some local memory (cache) where it can store some of the instructions to be performed for some added execution speed. Execution of the instructions by the processor may require usage of some input/output device (40), such as inputting data from a file stored on a hard disk, inputting commands from a keyboard, inputting data and/or commands from a touchscreen, outputting data to a display, or outputting data to a USB flash drive. In some embodiments, the operating system (25) facilitates these tasks by being the central element to gathering the various data and instructions required for the execution of the program and provide these to the microprocessor. In some embodiments the operating system may not exist, and all the tasks are under direct control of the processor (15), although the basic architecture of the target hardware device (10) will remain the same as depicted in FIG. 7. In some embodiments a plurality of processors may be used in a parallel configuration for added execution speed. In such a case, the executable program may be specifically tailored to a parallel execution. Also, in some embodiments the processor (15) may execute part of the implementation of FIGS. 1 to 6 and some other part may be implemented using dedicated hardware/firmware placed at an Input/Output location accessible by the target hardware (10) via local interface (35). The target hardware (10) may include a plurality of executable programs (30), wherein each may run independently or in combination with one another. A number of embodiments of the disclosure have been described. Nevertheless, it will be understood that various modifications may be made without departing from the spirit and scope of the present disclosure. Accordingly, other embodiments are within the scope of the following claims.

EXAMPLES

The related methods and systems herein disclosed are further illustrated in the following examples, which are provided by way of illustration and are not intended to be limiting. In particular, the following examples illustrate exemplary methods and protocols for collecting protein and nucleotide sequences, calculating sequence features, training and evaluating models and applying models for protein expression prediction. A person skilled in the art will appreciate the applicability and the necessary modifications to adapt the features described in detail in the present section, to additional protein and nucleotide datasets and related methods and systems according to embodiments of the present disclosure. The following materials and methods were used.

General Materials and Methods

In a specific example and case, sequence mapping & retrieval and feature calculation was performed in Python 2.7 [40] using BioPython [41] and NumPy [42]; executed and consolidated using Bash (shell) scripts; and parallelized where possible using GNU Parallel [43]. Data analysis and presentation was done in R [44] within RStudio [45] using magrittr [46], plyr [47], dplyr [48], asbio [49], and datamart [50] for data handling; ggplot2 [51], ggbeeswarm [52], GGally [53], gridExtra [54], cowplot [55], scales [56], viridis [57], and RColorBrewer [58, 59] for plotting; multidplyr [60] with parallel [44] and foreach [61] with iterators [62] and doMC [63]/doParallel [64] for parallel processing; and roxygen2 [65] for code organization and documentation as well as other packages as referenced.

Example 1: Collection of Data for Learning and Evaluation

Figure 8:
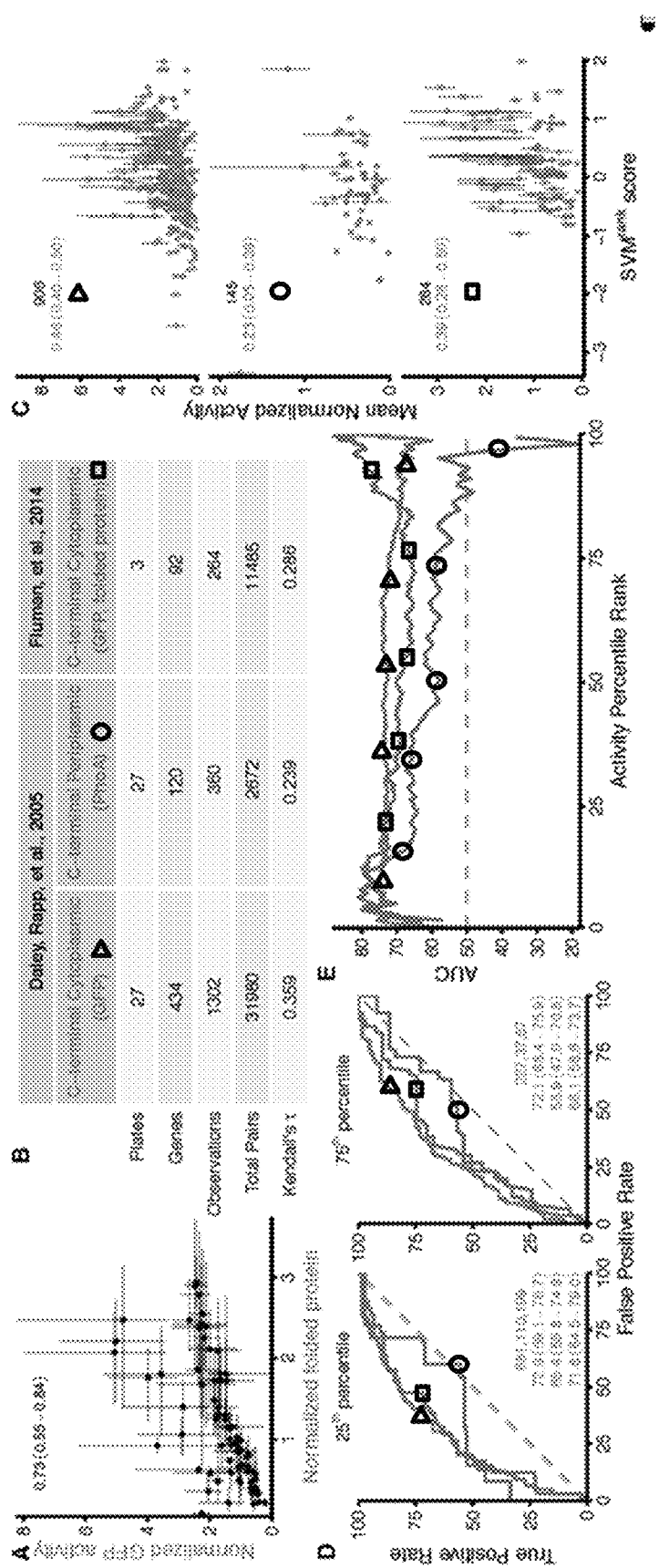
FIGS. 8-15 show data graphs and tables for Examples of the methods.

Literature search was conducted. Publications that contain quantitative datasets on the heterologous expression of *E. coli* membrane proteins in *E. coli* were identified. One of the publications, Daley, Rapp et al., contains activity measures, proxies for expression level, from C-terminal tags of either GFP or PhoA (alkaline phosphatase) [19]. Another publication, Fluman et al., contains a more detailed analysis of a subset from the Daley, Rapp et al. utilizing in-gel fluorescence to measure folded protein[20]. The expression results strongly correlated between the two datasets from Daley, Rapp et al. and Fluman et al in that normalized GFP activity was a good measure of the amount of folded membrane protein (FIG. 8, also [21]).

*E. coli* Sequence Data—The nucleotide sequences from [19] were deduced by reconstructing forward and reverse primers (i.e. ~20 nucleotide stretches) from each gene in Colibri (based on EcoGene 11), the original source cited and later verified these primers against an archival spreadsheet provided directly by Daniel Daley via personal communication. To account for sequence and annotation corrections made to the genome after Daley, Rapp, et al.'s work, these primers were directly used to reconstruct the amplified product from the most recent release of the *E. coli* K-12 substr. MG1655 genome(66) (EcoGene 3.0; U00096.3). Subsequent validation of the inferred nucleotide sequences against the protein lengths given in Table 1 from [19] confirmed that each deduced sequence was correct. The plasmid library tested in [20] was provided by Daniel Daley, and those sequences are taken to be the same.

*E. coli* Training Data—The preliminary results using the mean-normalized activities echoed the findings of [19] that these do not correlate with sequence features either in the univariate sense (many simple linear regressions) or a multivariate sense (multiple linear regression). This is presumably due to the loss of information regarding variability in expression level for given genes or due to the increase in variance of the normalized quantity due to the normalization and averaging procedure. The outcomes from the 96-well plates for the expression trial were obtained from Daniel Daley and Mikaela Rapp via personal communication. Those proteins without a reliable C-terminal localization (as given in the original work) or without raw expression outcomes were not included in further analyses. Similarly, the raw data from the set of three expression trials performed in [20] were also obtained from Nir Pluman via personal communication.

New York Consortium on Membrane Protein Structure (NYCOMPS) Data—Brian Kloss, Marco Punta, and Edda Kloppman provided a dataset of actions performed by the NYCOMPS center including expression outcomes in various conditions. [2, 3] The protein sequences were mapped to NCBI GenInfo Identifier (GI) numbers either via the Entrez system [67] or the Uniprot mapping service[68]. Each GI number was mapped to its nucleotide sequence via a combination of the NCBI Elink mapping service and the "coded_by" or "locus" tags of Coding Sequence (CDS) features within GenBank entries. Though a custom script was created, a script from Peter Cock on the BioPython listsery to do the same task via a similar mapping mechanism was found [69]. To confirm all the sequences, the TargetTrack [70] XML file was parsed for the internal NYCOMPS identifiers and compared for sequence identity to those that had been mapped using the custom script; 20 (less than 1%) of the sequences had minor inconsistencies and were manually replaced.

Archaeal Transporters Data—The locus tags were mapped directly to the sequences and retrieved from NCBI [25].

GPCR Expression Data—Nucleotide sequences were collected by mapping the protein identifiers given in Table 1 from [27] to protein GIs via the Uniprot mapping service [68] and subsequently to their nucleotide sequences via the custom mapping script described above (see NYCOMPS). The sequence length and pI were validated against those provided.

*Helicobacter pylori* Data—Nucleotide sequences were retrieved by mapping the locus tags given in Supplemental Table 1 from [28] to locus tags in the Jan. 31, 2014 release of the *H. pylori* 26695 genome (AE000511.1). To verify sequence accuracy, sequences whose molecular weight matched that given by the authors were accepted. Those that did not match, in addition to the one locus tag that could not be mapped to the Jan. 31, 2014 genome version, were retrieved from the Apr. 9, 2015 release of the genome (NC_000915.1). Both releases are derived from the original sequencing project [71]. After this curation, all mapped sequences matched the reported molecular weight.

In this data set, expression tests were performed in three expression vectors and scored as 1, 2, or 3. Two vectors were scored via two methods. For these two vectors, the two scores were averaged to give a single number for the condition making them comparable to the third vector while yielding 2 additional thresholds (1.5 and 2.5) result in the 5 total curves shown (panel B of FIG. 14).

*Mycobacterium tuberculosis* Data—TubercuList were used through GenoList[72], therefore, nucleotide sequences were retrieved from the archival website based on the original sequencing project [73]. The sequences corresponding to the identifiers and outcomes in Table 1 from [26] were validated against the provided molecular weight.

Secondary Transporter Data—GI Numbers given in Table 1 from [30] were matched to their CDS entries using the custom mapping script described above (see NYCOMPS). Only expression in *E. coli* with IPTG-inducible vectors was considered.

*Thermotoga maratima* Data—Gene names given in Table 1 of [74] were matched to CDS entries in the Jan. 31, 2014 release of the *Thermotoga maritima* MSB8 genome (AE000512.1), a revised annotation of the original release [75]. The sequence length and molecular weight were validated against those provided.

Example 2. Calculation of Sequence Features

Based on experimental analyses and anecdotal evidence, approximately 105 different protein and nucleotide sequence features thought to be relevant to expression were identified and calculated for each protein using custom code together with published software (codonW [76], tAI [77], NUPACK [78], Vienna RNA [79], Codon Pair Bias [80], Disembl [18], and RONN [81]). Relative metrics (e.g. codon adaptation index) are calculated with respect to the *E. coli* K-12 substr. MG1655 [66] quantity. The octanol-water partitioning [82], GES hydrophobicity [83], $\Delta G$ of insertion [16] scales were employed as well. Transmembrane segment topology was predicted using Phobius Constrained for the training data and Phobius for all other datasets [24]. Two RNA secondary structure metrics were prompted in part by [14]. Several features were obtained by averaging per-site metrics (e.g. per-residue RONN3.2 disorder predictions) in windows of a specified length. Windowed tAI metrics are calculated over all 30 base windows (not solely over 10 codon windows). Table 1 lists a description of each feature. Features are calculated solely from a gene of interest excluding portions of the ORFs such as linkers and tags derived from the plasmid backbone employed.

Example 3: Preparation for Model Learning

Calculated sequence features for the membrane proteins in the *E. coli* dataset as well as raw activity measurements, i.e. each 96-well plate, were loaded into R. As is best practice in using Support Vector Machines, each feature was "centered" and "scaled" where the mean value of a given feature was subtracted from each data point and then divided by the standard deviation of that feature using preprocess [84]. As is standard practice, the resulting set was then culled for those features of near zero-variance, over 95% correlation (Pearson's r), and linear dependence (nearZeroVar, findCorrelation, findLinearCombos)[84]. In particular, this procedure removed extraneous degrees of freedom during the training process which carry little to no additional information with respect to the feature space and which may over represent certain redundant features. Features and outcomes for each list ("query") were written into the SVM$^{light}$ format using a modified svmlight.write[85].

The final features were calculated for each sequence in the test datasets, prepared for scoring by "centering" and "scaling" by the training set parameters via preprocess[84], and then written into SVM$^{light}$ format again using a modified svmlight.write.

Example 4: Model Selection, Training, and Evaluation Using SVM$^{rank}$ a. At the most basic level, the predictive model herein described is a learned function that maps the parameter space (consisting of nucleotide and protein sequence features) to a response variable (expression level) through a set of governing weights ($w_1, w_2, \ldots, w_N$). Depending on how the response variable is defined, these weights can be approximated using several different methods. As such, defining a response variable that is reflective of the available training data is key to selecting an appropriate learning algorithm.

The quantitative 96-well plate results[19] that comprise the training data do not offer an absolute expression metric valid over all plates—the top expressing proteins in one plate would not necessarily be the best expressing within another. As such, this problem is suited for preference-ranking methods. As a ranking problem, the response variable is the ordinal rank for each protein derived from its overexpression relative to the other members of the same plate of expression trials. In other words, the aim is to rank highly expressed proteins (based on numerous trials) at higher scores than lower expressed proteins by fitting against the order of expression outcomes from each constituent 96-well plate.

b. One of the aspects was to employ the simplest framework necessary taking in account the considerations above. The method chosen computes all valid pairwise classifications (i.e. within a single plate) transforming the original ranking problem into a binary classification problem. The algorithm outputs a score for each input by minimizing the number of swapped pairs thereby maximizing Kendall's $\tau$[86]. For example, consider the following data generated via context A $(X_{A,1}, Y_{A,1}) (X_{A,2}, Y_{A,2})$ and B $(X_{B,1}, Y_{B,1})$, $(X_{B,2}, Y_{B,2})$ where observed response follows as index i, i.e. $Y_n < Y_{n+1}$. Binary classifier $f(X_i, X_j)$ gives a score of 1 if an input pair matches its ordering criteria and $-1$ if not, i.e. $Y_i < Y_j$:

$f(X_{A,1}, X_{A,2})=1$; $f(X_{A,2}, X_{A,1})=-1$;
$f(X_{B,1}, X_{B,2})=1$; $f(X_{B,2}, X_{B,1})=-1$;
$f(X_{A,1}, X_{B,2}), f(X_{A,2}, X_{B,1})$ are invalid Free parameters describing f are calculated such that those calculated orderings $f(X_{A,1}), f(X_{A,2}) \ldots ; f(X_{B,1}), f(X_{B,2}) \ldots$ most closely agree (overall Kendall's $\tau$) with the observed ordering $Y_n, Y_{n+1}, \ldots$. In this sense, f is a pairwise Learning to Rank method.

Within this class of models, a linear preference-ranking Support Vector Machine was employed[87]. To be clear, as an algorithm a preference-ranking SVM operates similarly to the canonical SVM binary classifier. In the traditional binary classification problem, a linear SVM seeks the maximally separating hyper-plane in the feature space between two classes, where class membership is determined by which side of the hyper-plane the points reside in. For some n linear separable training examples $D=\{(x_i)|x_i \in \mathbb{R}^d\}^n$ and two classes $y_i \in \{-1, 1\}$, a linear SVM seeks a mapping from the d-dimensional feature space $\mathbb{R}^d \to \{-1, 1\}$ by finding two maximally separated hyperplanes $w \cdot x - b = 1$ and $w \cdot x - b = -1$ with constraints that $w \cdot x_i - b \geq 1$ for all $x_i$ with $y_i \in \{1\}$ and $w \cdot x_i - b \leq -1$ for all $x_i$ with $y_i \in \{-1\}$. The feature weights correspond to the vector w, which is the vector perpendicular to the separating hyperplanes, and are computable in $O(n \log n)$ implemented as part of the SVM$^{rank}$ software package, though in $O(n^2)$(22). Weights for the learned SVM are pulled directly from the model file produced by SVM$^{light}$. Detailed information and related technical discussion can be found in reference [87].

c. In a soft-margin SVM where training data is not linearly separable, a tradeoff between misclassified inputs and separation from the hyperplane must be specified. This parameter C was found by training models against raw data from Daley, Rapp, et al. with a grid of candidate C values ($2^n \forall n \in [-5, 5]$) and then evaluated against the raw "folded protein" measurements from Fluman, et al. The final model was chosen by selecting that with the lowest error from the process above ($C=2^5$). To be clear, the final model is composed solely of a single weight for each feature; the tradeoff parameter C is only part of the training process.

Qualitatively, such a preference-ranking method constructs a model that ranks groups of proteins with higher expression level higher than other groups with lower expression value. In comparison to methods such as linear regression and binary classification, this approach is more robust and less affected by the inherent stochasticity of the training data.

As an algorithm, a preference-ranking SVM operates similarly to the canonical SVM binary classifier. In a binary classification problem, a linear SVM seeks the maximally separating hyper-plane in the feature space between two classes, where class membership is determined by which side of the hyperplane points reside. For some n linear separable training examples have $D=\{x_i | x_i \in \mathbb{R}^d\}^n$ and two classes $y_i \in \{-1,1\}$, with linear SVM seeking a mapping from the d-dimensional feature space, $\mathbb{R}^d \to \{-1,1\}$, by finding two maximally separated hyperplanes given by equations 1 and 2.

Example 5: Quantitative Assessment of Predictive Performance

In generating a predictive model, one aims to enrich for positive outcomes while ensuring they do not come at the cost of increased false positive diagnoses. This is formalized in Receiver Operating Characteristic (ROC) theory (for a primer see [23]), where the true positive rate is plotted against the false positive rate for all classification thresholds (score cutoffs in the ranked list). In this framework, the overall ability of the model to resolve positive from negative outcomes is evaluated by analyzing the area under an ROC curve (AUC) where $AUC_{perfect}=100\%$ and $AUC_{random}=50\%$ (percentage signs are omitted throughout the text and figures). All ROCs are calculated through pROC[88] using the analytic Delong method for AUC confidence intervals[89]. Bootstrapped AUC CIs ($N=10^6$) were precise to 4 decimal places suggesting that analytic CIs are valid for the NYCOMPS dataset.

In order to evaluate predictive performance, classification thresholds of positive expression for each dataset was tested as follows:

Training Data—The outcomes are quantitative (activity level), so each ROC is calculated by normalizing within each dataset to the standard well subject to the discussion in Example 4a above (LepB for PhoA, and InvLepB for GFP) (examples in FIG. 1D) for each possible threshold, i.e. each normalized expression value with each AUC plotted in FIG. 1E. 95% confidence intervals of Spearman's p are given by $10^6$ iterations of a bias-corrected and accelerated (BCa) bootstrap of the data (panels A and C of FIG. 8)[90].

Figure 9:
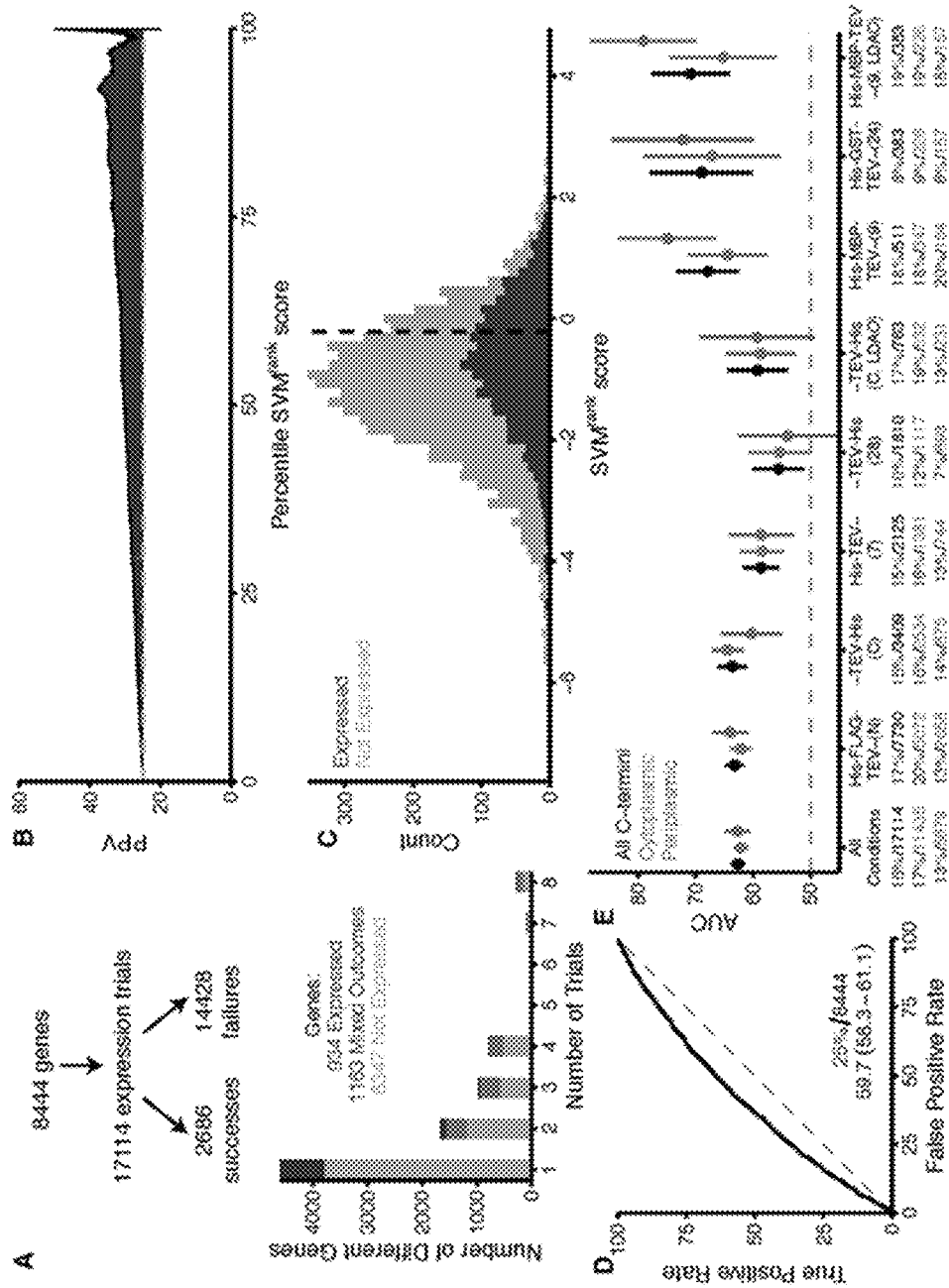

Large-Scale—ROCs were calculated for each of the expression classes (panel E of FIG. 9). Regardless of the split, predictive performance is noted. The bin-width for the histogram was determined using the Freedman-Diaconis rule, and scores outside the plotted range comprising <0.6% of the density were implicitly hidden.

Figure 10:
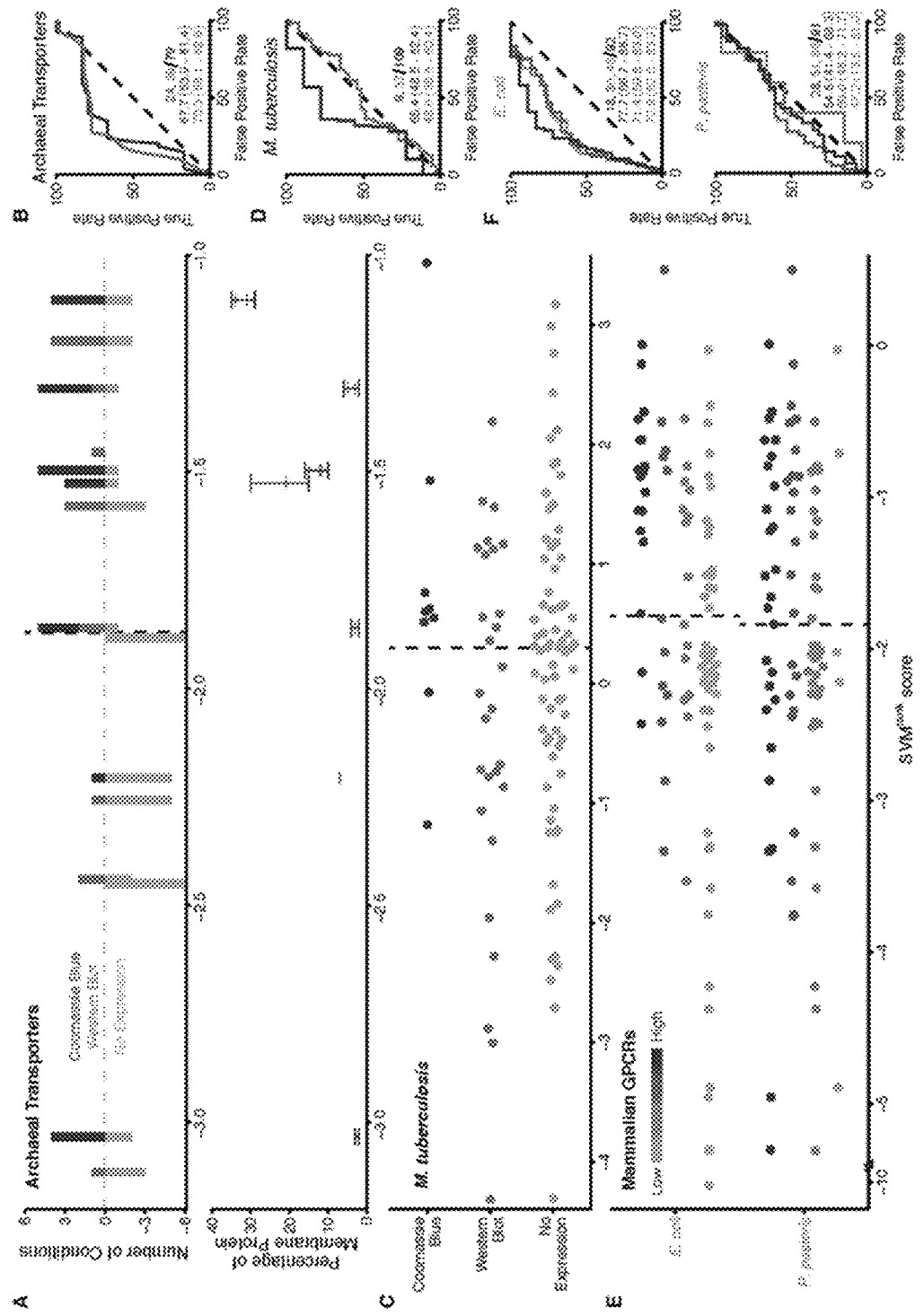

Small-Scale—Classes can be defined in many different ways. To be principled about the matter, ROCs for each possible cutoff are presented based on definitions from each publication (panels B, D, and F of FIG. 10; panels B, D, and F of FIG. 14).

Example 6: Development of a Computational Model Trained on E. coli Expression Data A key component of any machine learning model is the choice of dataset used for training. Having searched the literature, we identified two publications that contained quantitative datasets on the heterologous expression of E. coli membrane proteins in E. coli. The first set, Daley, Rapp et al., contained activity measures, proxies for expression level, from C-terminal tags of either GFP or PhoA (alkaline phosphatase) [19]. The second set, Fluman et al., contained a more detailed analysis of a subset from the first utilizing in-gel fluorescence to measure folded protein [20]. The expression results strongly correlated between the two datasets notably in that normalized GFP activity was a good measure of the amount of folded membrane protein (panel A of FIG. 8, also [21]). The experimental set-up employed multiple 96-well plates over multiple days resulting in pronounced variability in the absolute expression level of a given protein between trials. Daley, Rapp, et al. calculated average expression levels by dividing the raw expression level of each protein by that of a control construct (Inverse LepB-GFP or LepB-PhoA) on the corresponding plate. While the resulting values were useful for the relevant question of identifying topology, we were unable to successfully fit a linear regression or a standard linear-SVM on either the raw data compiled from all plates or averaged outcomes of each gene. This unexpected outcome suggested that the measurements required a more complex analysis.

We hypothesized that measurements could be more accurately compared within an individual plate then across the entire dataset. To account for this, a preference-ranking linear SVM algorithm ($SVM^{rank}$ [24]) was chosen (see above). Simply put, the $SVM^{rank}$ algorithm determines the optimal weight for each feature to best rank the order of expression outcomes within each plate over all plates, which results in a model where higher expressing proteins have higher scores. The outcome is identical in structure to a multiple linear regression, but instead of minimizing the sum of squared residuals, the SVM cost function is used accounting for the plate-wise constraint specified above. In practice, the process optimizes as a training metric the correlation coefficient Kendall's τ to converge upon a set of weights. Kendall's τ measures the agreement between ordinal quantities by calculating correctly-ordered and swapped pairs.

Various metrics related to the training data can be derived to assess the accuracy with which the model fits the input data. The $SVM^{rank}$ training metric shows varying agreement for all groups (i.e., $\tau_{kendall}>0$) (Table 2, panel B of FIG. 8). For individual genes, activity values normalized and averaged across trials were not directly used for the training procedure (see Methods 4a); yet one would anticipate that scores for each gene should broadly correlate with expression. Indeed, the observed normalized activities positively correlate with the $SVM^{rank}$ score output by the model (panel C of FIG. 1).

TABLE 2

| | Daley, Rapp, et al. (2005) | | Fluman, et al. (2014) |
|---|---|---|---|
| | C-terminal Cytoplasmic (GFP) | C-terminal Periplasmic (PhoA) | C-terminal Cytoplasimic (GFP, folded protein) |
| Plates | 28 | 27 | 3 |
| Genes | 372 | 105 | 92 |
| Observations | 1488 | 405 | 264 |
| Total Pairs | 40525 | 3098 | 11485 |
| Kendall's tau | 0.345 | −0.001 | 0.286 |

For a more quantitative approach to assessing the models success within the training data, we turn to the Receiver Operating Characteristic (ROC). ROC curves quantify the tradeoff between true positive and false positive predictions across the numerical scores output from a predictor. This is a more reliable assessment of prediction than simply calculating accuracy and precision from a single, arbitrary score threshold [25]. The figure of merit that quantifies an ROC curve is the Area Under the Curve (AUC). Given that the AUC for a perfect predictor corresponds to 100% and that of a random predictor is 50% (panel D of FIG. 8, dashed line), an AUC greater than 50% indicates predictive performance of the model (percentage signs hereafter omitted) [25]. Here, the ROC framework will be used to quantitatively assess the ability of our model to predict the outcomes within the various datasets.

The training datasets are quantitative measures of activity requiring that an activity threshold be chosen that defines positive or negative outcomes. For example, ROC curves using two distinct activity thresholds, at the $25^{th}$ or $75^{th}$ percentile of highest expression, are plotted with their calculated AUC values (panel D of FIG. 8). While both show that the model has predictive capacity, a more useful visualization would consider all possible activity thresholds. For this, the AUC value for every activity threshold is plotted showing that the model has predictive power regardless of an arbitrarily chosen expression threshold (FIG. 1E). In total, the analysis demonstrates that the model can rank expression outcomes for all proteins. Interestingly, for PhoA-tagged proteins the model is progressively less successful with increasing activity. PhoA activity is an indirect measure of expression of proteins with their C-termini in the periplasm bringing into question either the utility of this quantification method relative to GFP activity or perhaps that this class of proteins are special in the model. An argument for the former is presented later (panel E of FIG. 9).

While agreement is expected within the training datasets, the broader applicability of a model can be assessed through comparison with the outcomes of independent large- and small-scale expression trials.

Example 7: Demonstration of Prediction Against an Independent Large Expression Dataset The broader applicability of the model was assessed based on its capability at predicting the outcomes of independent large- and small-scale expression trials. In this example, the performance of the model was tested against datasets from NYCOMPS, where 8444 membrane protein genes entered expression trials, in up to eight conditions, resulting in 17114 expression outcomes [2]. The majority of genes were attempted in only one condition (panel A of FIG. 9), and outcomes were non-quantitative (binary: expressed or not expressed) as indicated by the presence of a band by Coomassie staining of an SDS-PAGE gel after small-scale expression, solubilization, and purification [3]. Therefore, for this analysis, the experimental results in various ways were considered: either outcomes per gene (if at least one trial is positive, the gene is considered positive for expression), all conditions (each expression trial considered independently), or based on defined expression conditions. For the first, several metrics demonstrate prediction (panels B-D of FIG. 9).

One of the main aspects is to enrich the likelihood of choosing positively expressing proteins. The positive predictive value (PPV, true positives÷predicted positives) becomes a useful metric for positive enrichment as it conveys the degree of improvement over the experimental baseline of the dataset. The PPV of the model is plotted as a function of the percentile of the $SVM^{rank}$ score threshold for the definition of predicted positives (panel B of FIG. 9). In the figure, the overall positive percentage (~24%), an experimental baseline, is represented by a grey dashed line; therefore, a relative increase reflects the increased predictive power of the algorithm. For example, considering the top fourth of genes by $SVM^{rank}$ score ($75^{th}$ percentile) shows that the algorithm enriches for positive outcomes by 8.4% over baseline. Seen another way, a histogram of the $SVM^{rank}$ score for each protein is plotted separated by positive versus negative outcomes (panel C of FIG. 9). Visually, the distribution of the scores for the positive group is shifted to a higher score relative to the negative group, which is substantiated quantitatively by the ROC and its corresponding AUC (panel D of FIG. 9). Interestingly, considering the predictive power against all conditions as opposed to by gene shows slightly better statistics (AUC=62.6) reflective of the fact that many genes have mixed outcomes (panel E of FIG. 9). Importantly, the model shows consistent performance throughout each of the eight possible conditions tested (panel E of FIG. 9).

The ability to predict the experimental data from NYCOMPS allows a return to the question of alkaline phosphatase as a metric for expression. To investigate the trend that the expression of proteins with periplasmic C-termini measured by alkaline phosphatase (FIG. 8) show less consistent fitting by the model, the NYCOMPS outcomes are split by putative C-terminal localization as predicted by Phobius [24]. That there is no significant difference in AUC between C-terminal localizations across all conditions (panel E of FIG. 9) indicates that the model is applicable for all topologies.

Example 8: Demonstration of Prediction Against an Independent Small-Scale Expression Dataset In this example, the performance of the model is tested against relevant subsets of sequence space (e.g. a family of proteins or the proteome from a single organism), which are reminiscent of laboratory-scale experiments that precede structural or biochemical analyses. While a number of datasets exist [8, 25-35], only six were identified for which complete sequence information could be obtained to calculate all the necessary sequence parameters [25-30].

The first dataset is derived from the expression of 14 archaeal transporters in *E. coli* chosen based on their homology to human proteins[25]. For each putative transporter, expression was performed in three plasmids and two strains (six total conditions) with the membrane fraction quantified by both a Western blot against a histidine-affinity tag and Coomassie Blue staining of an SDS-PAGE gel. Here, the majority of the expressing proteins fall into the top half of the $SVM^{rank}$ scores, 7 out of 9 of those with multiple positive outcomes (panel A of FIG. 10, top). Strikingly, quantification of the Coomassie Blue staining highlights a clear correlation with the $SVM^{rank}$ score where the higher expressing proteins have the highest score (panel A of FIG. 10, bottom). ROC curves are plotted for the two thresholds: expression detected at least by Western blot or, for the smaller subset, by Coomassie Blue (panel B of FIG. 10). In both cases, the model shows predictive power.

The next test considers the expression of 105 *Mycobacterium tuberculosis* proteins in *E. coli*[26]. Protein expression was measured both by Coomassie Blue staining of an SDS-PAGE gel and Western blot with only outcomes from the membrane fraction considered for this analysis. The highest expressing proteins (detected via Coomassie Blue) follow the trend given by the SVM$^{rank}$ score with 7 of the 9 falling within the top half of scoring proteins (panel C of FIG. 10) and is reflected in the ROC (panel D of FIG. 10). In contrast, using the positive Western blot outcomes as the minimum threshold (panel C of FIG. 10) shows an AUC no better than random (panel D of FIG. 10). Given that no internal standard was used and that each expression trial was performed only once, proteins that were positive by Western blot may represent a pool indistinguishable in expression from those not detected; alternatively, these results support that our statistical model accurately captures the most highly expressing proteins.

A broader test considers expression trials of 101 mammalian GPCRs in bacterial and eukaryotic systems [27]. Trials in *E. coli*, measured via Western blot of an insoluble fraction, again show highly expressing proteins at higher SVM$^{rank}$ scores while the expression of the same proteins in *P. pastoris*, measured via dot blot, fail to show broad agreement (panels E and F of FIG. 10). The lack of predictive performance in *P. pastoris* suggests that the parameterization of the model, calibrated for broadly characterizing *E. coli* expression, requires retraining to generate a different model that captures the distinct interplay of sequence parameters in yeast.

Figure 14:
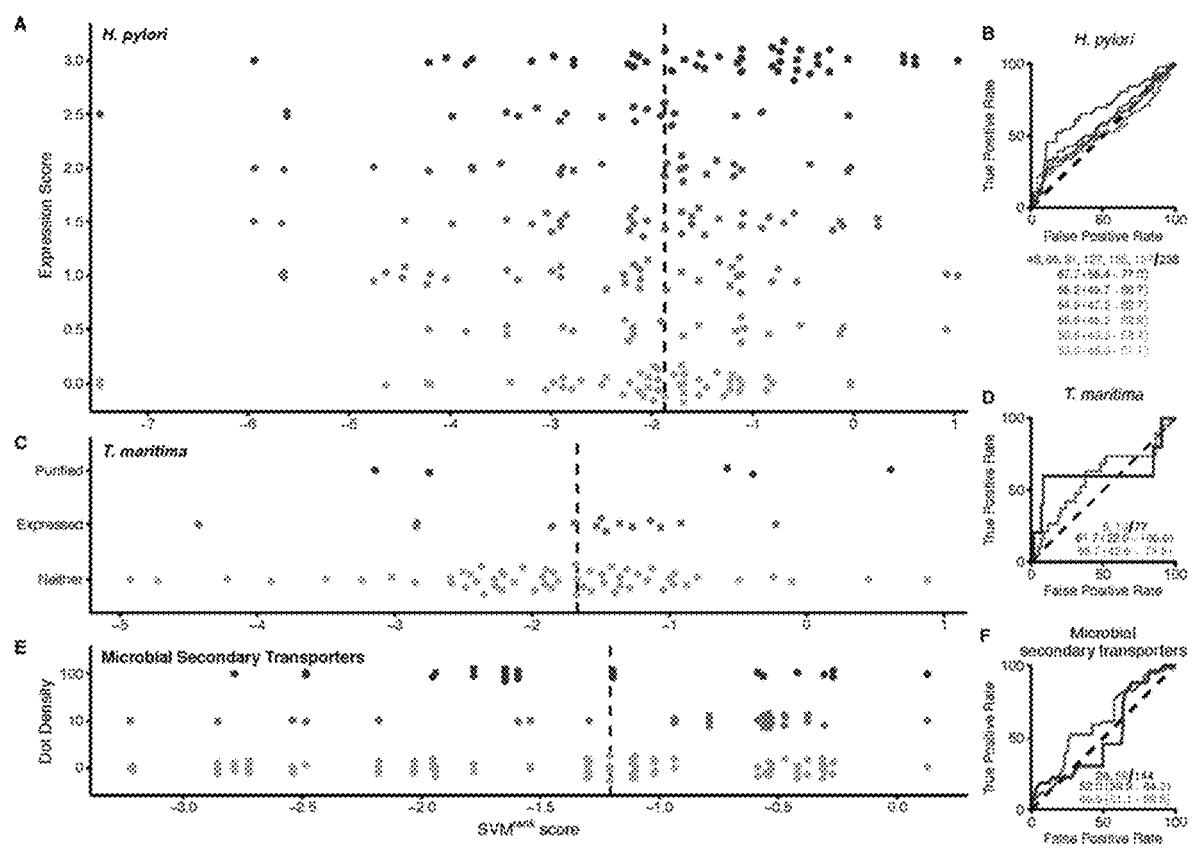

Further expression trials of membrane proteins from *H. pylori, T. maritima* as well as microbial secondary transporters continues to show the same broad agreement [28-30] (FIG. 14). *H. pylori* membrane proteins showed that as the threshold for positive expressing proteins increases, the performance of the model improves (using the highest threshold n=46 and AUC=67.7) (panels A and B of FIG. 14). For *T. maritima* expression, the model weakly captures outcomes for two defined thresholds (n=5 and 19, AUC=61.7 and 58.7), but due to the small number of successful outcomes, the confidence intervals are broad (panels C and D of FIG. 14). The expression of microbial secondary transporters shows varied agreement with the model. Taking proteins at the lower defined expression threshold shows predictive performance (n=59, AUC=60.5); however, considering the defined high-expressing proteins is less conclusive (n=26, AUC=52.0) (panels E and F of FIG. 14).

Example 9: Forward Predictions

Figure 11:
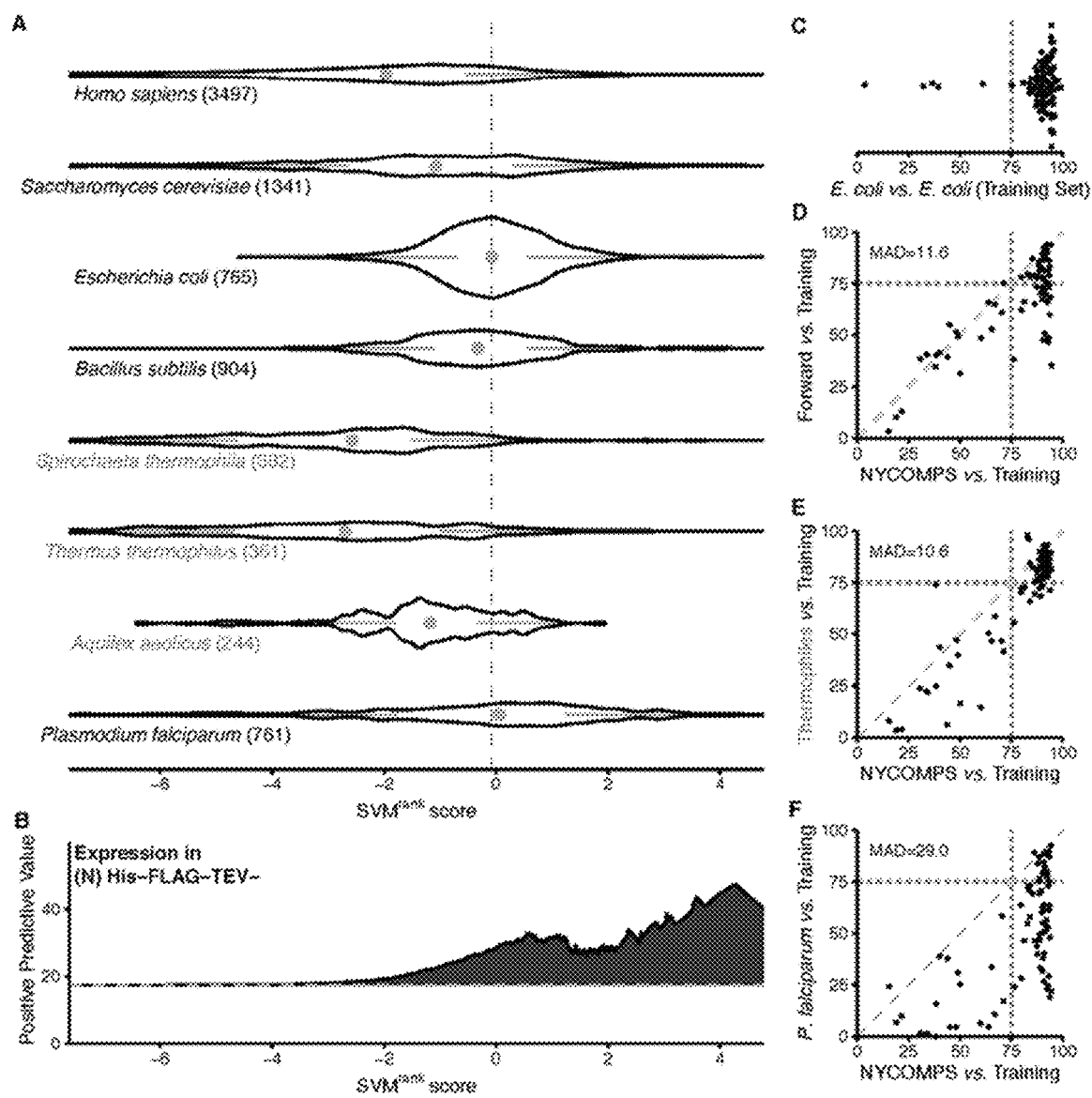
Figure 15:
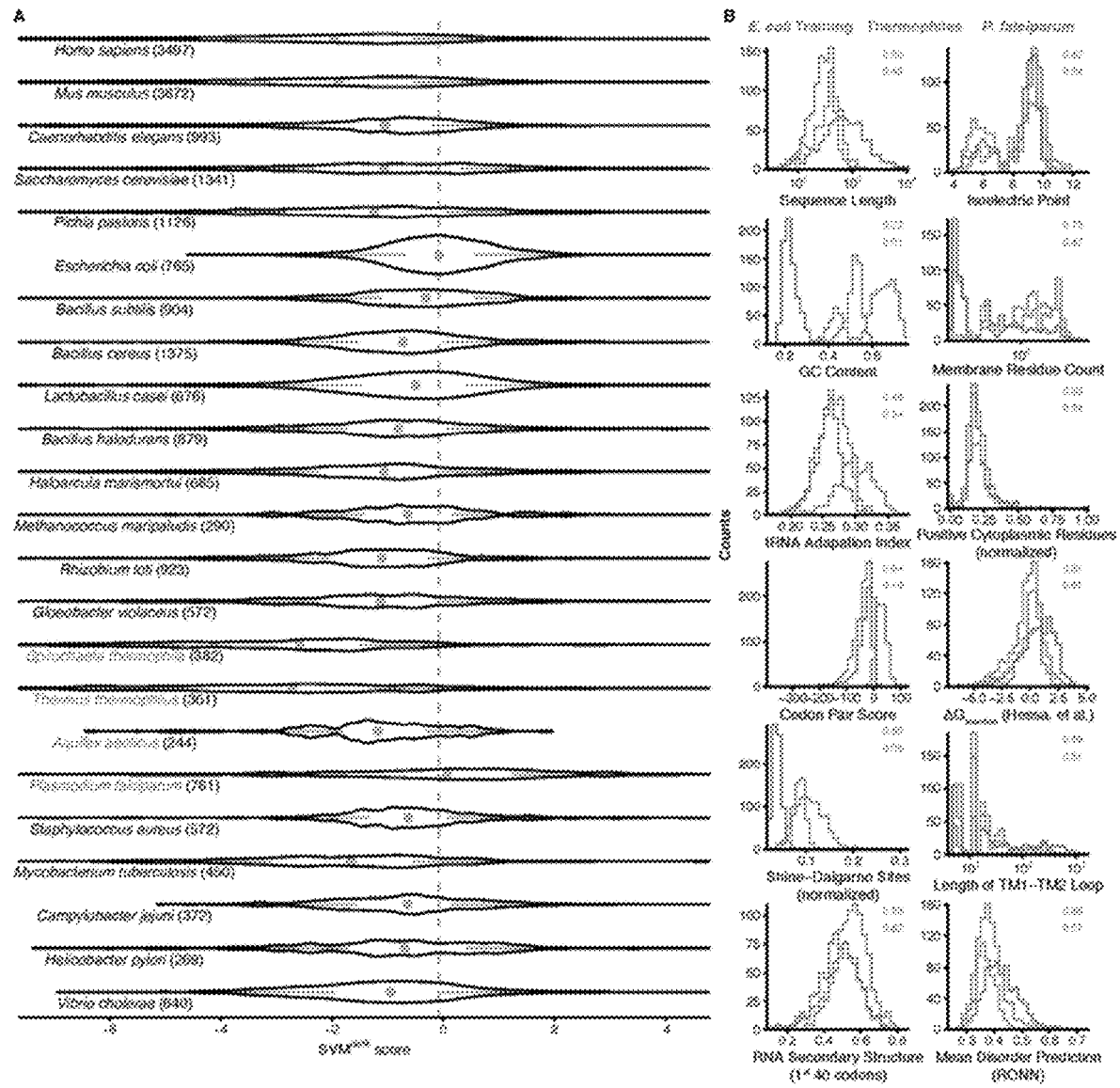

Data Collection—Several genomes for comparison as shown in FIG. 11, panel A of FIG. 15 were selected. Coding sequences of membrane proteins from human and mouse genomes were gathered by mapping Uniprot identifiers of proteins noted to have at least one transmembrane segment by Uniprot [68] to Ensembl (release 82) coding sequences [91] via Biomart. [92] *C. elegans* coding sequences were similarly mapped via Uniprot but to WormBase coding sequences [93] also via Biomart. *S. cerevisiae* strain S288C coding sequences [94] were retrieved from the *Saccharomyces* Genome Database. *P. pastoris* strain GS115 coding sequences [95] were retrieved from the DOE Joint Genome Institute (JGI) Genome Portal [96]. Those sequences without predicted [24] TMs were excluded from subsequent analyses. Microbial sequences were gathered via a custom, in-house database populated with data compiled primarily from Pfam [36], DOE JGI Integrated Microbial Genomes [97], and the Microbial Genome Database [98].

Feature Calculation—Because of the incredible number of sequences, the features derived from the most computationally expensive calculation (whole sequence mRNA pairing probability) were not calculated. Since predictive performance on the NYCOMPS dataset is slightly smaller, but not significantly different at 95% confidence, in the absence of these features, the forward predictions are still valid. For future experiments, these features can be calculated for the subset of targets of interest.

Parameter Space Similarity—As a first approximation of the similarity of the ~90 dimensional sequence parameter space between two groupings, features were compared pairwise via the following metric. Let $f_i$ and $g_i$ represent the true distributions for a given feature i between two groups of interest. The distribution overlap, i.e. shared area, $\Delta_i$ is formalized as $$\Delta_i(f_i, g_i) = \int \min\{f_i(x), g_i(x)\} dx$$

ranging from 0, for entirely distinct distributions, to 1 for entirely identical distributions.

As written $f_i$ and $g_i$ are probability densities, they need to be approximated before calculating $\Delta_i$ and are done so via kernel density estimates (KDE) of the observed samples $[x_1^f, \ldots, x_n^f]$ and $[x_1^g, \ldots, x_n^g]$ using a nonparametric, locally adaptive method allowing for variable bandwidth smoothing implemented in LocFit(99) (adpen=$2\sigma^2$) providing $\hat{f}_i$ and $\hat{g}_i$. The distribution overlap $\Delta_i$ is evaluated over a grid of $2^{13}$ equally spaced points over the range of $f_i$ and $g_i$.

Figure 13:
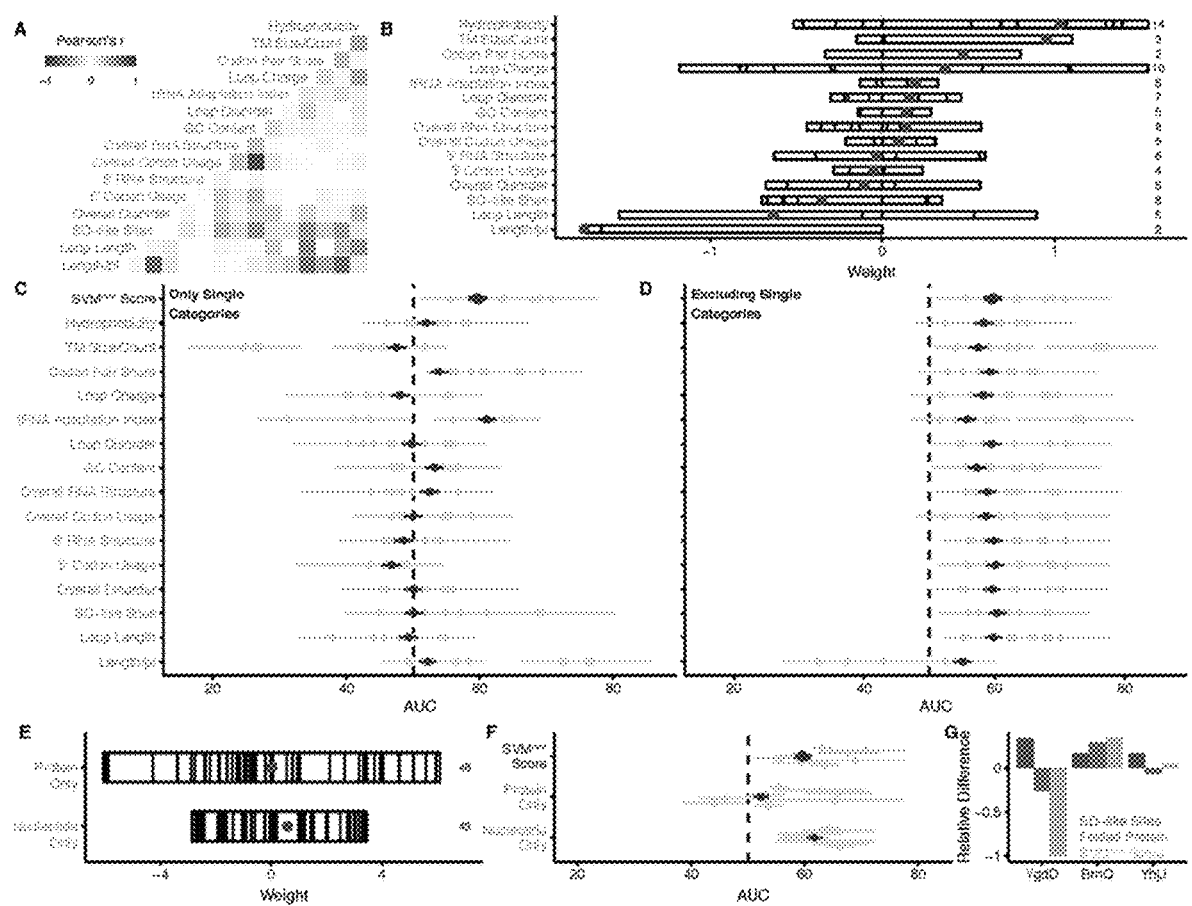

Shine-Dalgarno-Like Mutagenesis—Folded protein is quantified by densitometry measurement [100, 101] of the relevant band in FIG. 13 of Fluman, et al. Relative difference is calculated as is standard:

$$\frac{metric_{mutant} - metric_{wildtype}}{\frac{1}{2}|metric_{mutant} - metric_{wildtype}|}$$

Example 10: Forward Predictions on Genomes of Interest

To expand on the utility of this model, SVM$^{rank}$ scores were calculated for membrane proteins from a variety of metazoan and microbial genomes (panel A of FIG. 11 and panel A of FIG. 9). Many genomes have a significant proportion of proteins with high scores particularly evidenced by portions of the distributions ahead of the median in *E. coli* given by the vertical dashed line (panel A of FIG. 11). The likelihood for successful expression may be inferred by equating SVM$^{rank}$ score with the PPV from the most prevalent NYCOMPS expression condition which rises dramatically at scores above zero (panel B of FIG. 11). The range of scores spans those scores representative of high-expressing membrane proteins in both *E. coli* (panel C of FIG. 8) as well as in the NYCOMPS dataset (panel C of FIG. 9) and provides suggested targets for future biophysical studies.

The predictions present several surprises at the biological level. One is that the distribution of membrane proteins from representative thermophilic bacterial genomes has generally lower relative SVM$^{rank}$ scores than other genomes, which implies that these proteins, on average, are harder to express in *E. coli*. This contrasts the many empirical examples of proteins from thermophiles being used for biophysical characterization. In the case of the malarial parasite *P. falciparum*, the inverse trend is true with higher than expected relative SVM$^{rank}$ scores despite the expectation that these proteins would be hard to express in *E. coli*. A possible cause for the unexpected distribution of scores may lie in the differences in the parameters that define the proteins in these particular groups. As the training set consists only of native *E. coli* sequences, the range of values for each parameter in the training set may not represent the full range of possible values for the parameter. For the special cases highlighted, perhaps the underlying sequence parameters fall into a poorly characterized subset of sequence space bringing into question the applicability of the model for these cases.

To address the utility of the model relative to differences in the sampling of sequence parameters, the overlap of the distributions of sequence parameters for a given subset was measured (see Example 9) (panel B of FIG. 15). Simply put, if two subsets contain the same distribution of sequence parameters the expectation is that a given parameter should approach 100%. In the simplest case, comparing the distribution of sequences parameters in all *E. coli* membrane proteins against the subset used in the training set shows that the majority of parameters have overlap values over 75% (panel C of FIG. 11), which provides a lower threshold for similarity of sequence parameter range. For NYCOMPS sequences, most of the overlap values relative to the training set are above the threshold. As this set shows predictive performance, comparison to the training set provides a baseline to assess the reliability of predictions within other subsets (panels D-F of FIG. 11, x-axis). In the first case (panel D of FIG. 11), there is a strong correlation between all the forward predictions and NYCOMPS, i.e. values are near the diagonal (quantified by a Mean Absolute Deviation (MAD)=11.6), suggesting that differences in parameter space do not significantly affect the predictive power of the model. For the thermophiles subset (FIG. 4E), the values again are close to the diagonal (i.e. low MAD=10.6) implying that the predictions are credible. *P. falciparum* (panel F of FIG. 11), on the other hand, clearly shows stark differences as most parameters fall below the 75% cut-off (MAD=29.0) bringing into question the reliability of these predictions. A training set with broader coverage of the parameter space may generate a better predictor for all genomes.

Example 11: Performance of the Model Across Protein Families

Figure 12:
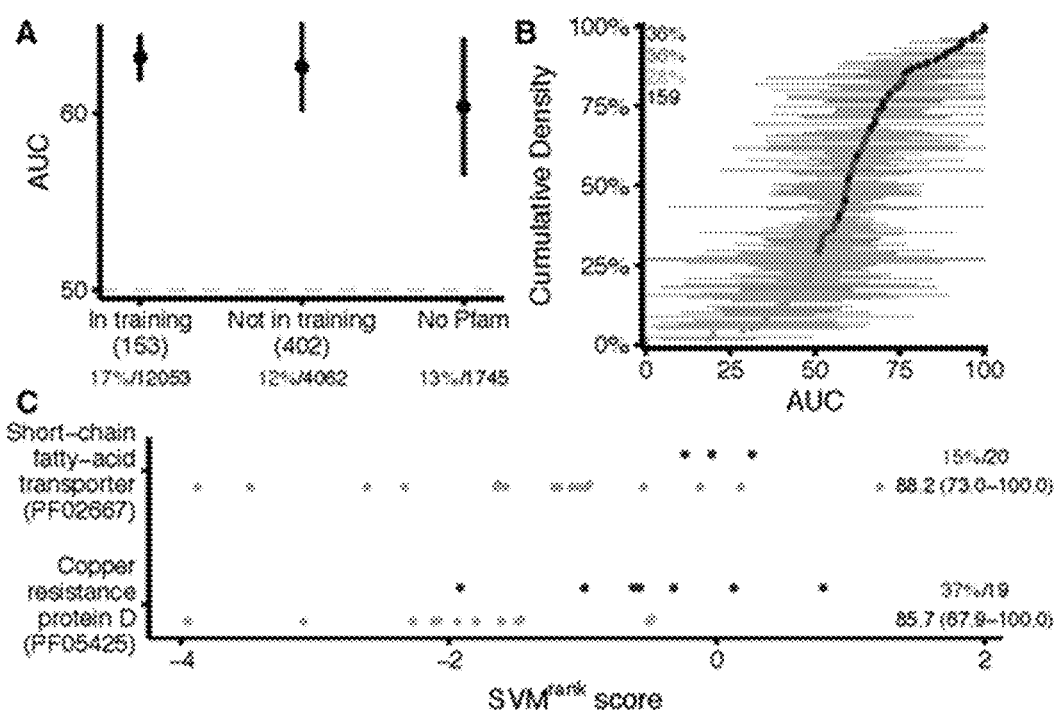

This example tests the performance of the model with regards to protein homology families where protein family definitions are based on Pfam classifications [36]. For outcomes from NYCOMPS (panel A of FIG. 12), there are no significant difference in the predictive performance of the model between groups of genes whether or not they are part of a protein family found in the training set.

The scale of NYCOMPS allows us to investigate whether there are protein families for which the model does better or worse than the aggregate. For this, an AUC is calculated for each protein family that has minimally five total outcomes (including at least one positive and one negative). FIG. 5B plots the AUC for each protein family in increasing order as a cumulative distribution function. The breadth of the AUC values highlights the variability in predictive power across families. Most families can be predicted by the model (115 of 159 have an AUC>0.5) though some not at 95% confidence (57 of 115), likely due to an insufficient number tested.

For the protein families that are well-predicted within the NYCOMPS set, the model gives accurate insight into the likelihood of expression of a given protein. We demonstrate the utility of this prediction by looking at protein families that have yet to be characterized structurally. While there are a number of choices, a first example is the protein family annotated as short-chain fatty-acid transporters (PF02667), characterized by AtoE in *E. coli*, which typically contains 10 transmembrane domains with an overall length of ~450 amino acids. A second example is the protein family annotated as copper resistance proteins (PF05425), characterized by CopD in *E. coli*, that typically contains eight transmembrane domains with an overall length of ~315 amino acids. In both cases, as indicated by the AUC values, the model provides a clear score cut-off for consideration for expression. For example, considering CopD homologs, one would expect that those with $SVM^{rank}$ scores above −1 will express.

Example 12: Biological Importance of Various Sequence Parameters

Using a simple proof-of-concept linear model allowed for a straightforward and robust predictor; however, intrinsically this complicates determination of biological underpinnings due to the unequal distribution of weight across correlating features. For example, the average $\Delta G_{insertion}$ of transmembrane segments has a positive weight whereas average hydrophobicity, a correlating parameter, has a negative weight. As many parameters, such as those related to hydrophobicity, are highly correlated; conclusive information cannot be obtained simply using weights of individual features to interpret the relative importance of their underlying biological phenomena. An alternative is to collapse related features into biologically meaningful categories reducing correlation (panel A of FIG. 13), thereby providing a mechanism to interpret information from the model. For example, the hydrophobicity group incorporates sequence features such as average hydrophobicity, maximum hydrophobicity, $\Delta G_{insertion}$, etc. The full list of groupings is provided in Table 1.

Analysis of categories suggests the phenomena that drive prediction. To visualize this, the collapsed weights are summarized in panel B of FIG. 13 where each bar contains individual feature weights within a category. Features with a negative weight are stacked to the left of zero and those with a positive weight are stacked to the right. A red dot represents the sum of all weights, and the length of the bar gives the total absolute value of the combined weights within a category. Ranking the categories based on the sum of their weight suggests that some of categories play a more prominent role than others. These include properties related to transmembrane segments (hydrophobicity and TM size/count), codon pair score, loop length, and overall length.

To explore the role of each category in prediction, the performance of the model was calculated by either only using weights from features within a single category or excluding weights from within a single category. The predictive performances were assessed by calculating ROC curves across genes and expression trials from NYCOMPS dataset for each case (panels C and D FIG. 13). Feature categories that are sufficient for prediction will have an AUC>0.5 when used alone (panel C of FIG. 13) and those necessary for the model will show an AUC<0.5 when excluded from prediction (panel D of FIG. 13). Notably, when only considering all genes independent of condition, most individual categories cannot predict expression (i.e. AUC with 95% CI straddling 0.5) (panel C of FIG. 13). A notable exception is tRNA Adaptation Index, where the per gene AUC is slightly higher than the performance of the model. However, since the model demonstrates predictive performance at 95% confidence across all experimental conditions (panel E of FIG. 9), feature categories that are sufficient for prediction must also perform across these conditions. In this case, tRNA Adaptation Index performs poorly against a number of the experimental subsets, so it is not sufficient for prediction. On the other hand, while Codon Pair Score alone shows predictive power across experimental conditions, when excluded from the model, the category alone cannot explain the model (only a single 95% confidence interval crossing AUC=50, panel D of FIG. 13).

No feature category independently drives the predictor as excluding each individually does not significantly affect the overall predictive performance, except for Length/pI (isoelectric point) (panel D of FIG. 13). Sequence length composes the majority of the weight within this category and is one of the highest weighted features in the model. This is consistent with the anecdotal observation that larger membrane proteins are typically harder to express. However, this parameter alone would not be useful for predicting within a smaller subset, like a single protein family, where there is little variance in length (e.g. FIGS. 10,11). One might develop a predictor that was better for a given protein family under certain conditions with a subset of the entire features considered here; yet this would require a priori knowledge of the system, i.e. which sequence features were truly most important, and would preclude broad generalizability as shown for the predictor presented here.

A coarser view of the weights is a comparison of the features derived from either protein or nucleotide sequence. The summed weight for protein features is around zero, whereas for nucleotide features the summed weight is slightly positive suggesting that in comparison these features may be more important to the predictive performance of the model (panel E of FIG. 13). Comparison of the predictive performance of the two subsets of weights shows that the nucleotide features alone can give similar performance to the full model (panel F of FIG. 13). It is important to note that this does not suggest that protein features are not important for membrane protein expression. Instead, within the context of the trained model, nucleotide features are critical for predictive performance for a large dataset such as NYCOMPS. This finding corroborates growing literature that the nucleotide sequence holds significant determinants of biological processes [14, 20, 37-39].

Example 13: Sequence Optimization for Expression

To test whether altering the number of Shine-Dalgarno (SD)-like sites in the coding sequence of a membrane protein would affect expression, silent mutations were engineered within the first 200 bases of three proteins (genes ygdD, brnQ, and ybjJ from *E. coli*) to increase the number of SD-like sites with the goal of improving expression. Expression trials demonstrated that only one of the proteins (BrnQ) had improved expression of folded protein (panel G of FIG. 13). However, the resulting changes in the SVM$^{rank}$ score correspond with the changes in measured expression as the model considers changes to other nucleotide features. Capture of the outcomes in this small test case by the model illustrates the utility of integrating the contribution of the numerous parameters involved in membrane protein biogenesis.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually. Further, the computer readable form of the sequence listing of the ASCII text file P2015-US-Seq-List-ST25 is incorporated herein by reference in its entirety.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

REFERENCES

1. S. H. White, Biophysical dissection of membrane proteins. *Nature.* 459, 344-346 (2009).
2. M. Punta et al., Structural genomics target selection for the New York consortium on membrane protein structure. *J. Struct. Funct. Genomics.* 10, 255-268 (2009).
3. J. Love et al., The New York Consortium on Membrane Protein Structure (NYCOMPS): a high-throughput platform for structural genomics of integral membrane proteins. *J. Struct. Funct. Genomics.* 11, 191-199 (2010).
4. H. M. Berman et al., The Protein Data Bank. *Nucleic Acids Res.* 28, 235-242 (2000).
5. R. M. Bill et al., Overcoming barriers to membrane protein structure determination. *Nat. Biotechnol.* 29, 335-340 (2011).
6. M. H. H. Nørholm et al., Manipulating the genetic code for membrane protein production: what have we learnt so far? *Biochim. Biophys. Acta.* 1818, 1091-1096 (2012).
7. S. Wagner et al., Tuning *Escherichia coli* for membrane protein overexpression. *Proc. Natl. Acad. Sci. U.S.A* 105, 14371-14376 (2008).
8. O. Lewinson, A. T. Lee, D. C. Rees, The funnel approach to the precrystallization production of membrane proteins. *J. Mol. Biol.* 377, 62-73 (2008).
9. S. S. Marshall et al., A Link between Integral Membrane Protein Expression and Simulated Integration Efficiency. *Cell Rep.* 16, 2169-2177 (2016).
10. C. A. Sarkar et al., Directed evolution of a G protein-coupled receptor for expression, stability, and binding selectivity. *Proc. Natl. Acad. Sci. U.S.A* 105, 14808-14813 (2008).
11. K. M. Schlinkmann et al., Critical features for biosynthesis, stability, and functionality of a G protein-coupled receptor uncovered by all-versus-all mutations. *Proc. Natl. Acad. Sci. U.S.A* 109, 9810-9815 (2012).
12. S. Seppala, J. S. Slusky, P. Lloris-Garcerá, M. Rapp, G. von Heijne, Control of membrane protein topology by a single C-terminal residue. *Science.* 328, 1698-1700 (2010).

13. R. C. Van Lehn, B. Zhang, T. F. Miller, Regulation of multispanning membrane protein topology via post-translational annealing. *eLife.* 4 (2015), doi:10.7554/eLife.08697.
14. D. B. Goodman, G. M. Church, S. Kosuri, Causes and effects of N-terminal codon bias in bacterial genes. *Science.* 342, 475-479 (2013).
15. K. Mirzadeh et al., Enhanced Protein Production in *Escherichia coli* by Optimization of Cloning Scars at the Vector-Coding Sequence Junction. *ACS Synth. Biol.* (2015), doi:10.1021/acssynbio.5b00033.
16. T. Hessa et al., Molecular code for transmembrane-helix recognition by the Sec61 translocon. *Nature.* 450, 1026-1030 (2007).
17. G. Heijne, The distribution of positively charged residues in bacterial inner membrane proteins correlates with the trans-membrane topology. *EMBO J.* 5, 3021-3027 (1986).
18. R. Linding et al., Protein disorder prediction: implications for structural proteomics. *Structure.* 11, 1453-1459 (2003).
19. D. O. Daley et al., Global topology analysis of the *Escherichia coli* inner membrane proteome. *Science.* 308, 1321-1323 (2005).
20. N. Fluman, S. Navon, E. Bibi, Y. Pilpel, mRNA-programmed translation pauses in the targeting of *E. coli* membrane proteins. *eLife.* 3 (2014), doi:10.7554/eLife.03440.
21. E. R. Geertsma, M. Groeneveld, D.-J. Slotboom, B. Poolman, Quality control of overexpressed membrane proteins. *Proc. Natl. Acad. Sci. U.S.A* 105, 5722-5727 (2008).
22. I. Tsochantaridis, T. Joachims, T. Hofmann, Y. Altun, Large Margin Methods for Structured and Interdependent Output Variables. *J. Mach. Learn. Res.* 6, 1453-1484 (2005).
23. J. A. Swets, R. M. Dawes, J. Monahan, Better decisions through science. *Sci. Am.* 283, 82-87 (2000).
24. L. Käll, A. Krogh, E. L. L. Sonnhammer, A combined transmembrane topology and signal peptide prediction method. *J. Mol. Biol.* 338, 1027-1036 (2004).
25. P. Ma et al., An efficient strategy for small-scale screening and production of archaeal membrane transport proteins in *Escherichia coli. PloS One.* 8, e76913 (2013).
26. A. Korepanova et al., Cloning and expression of multiple integral membrane proteins from *Mycobacterium tuberculosis* in *Escherichia coli. Protein Sci.* 14, 148-158 (2005).
27. K. Lundstrom et al., Structural genomics on membrane proteins: comparison of more than 100 GPCRs in 3 expression systems. *J. Struct. Funct. Genomics.* 7, 77-91 (2006).
28. G. Psakis et al., Expression screening of integral membrane proteins from *Helicobacter pylori* 26695. *Protein Sci.* 16, 2667-2676 (2007).
29. E. Dobrovetsky et al., High-throughput production of prokaryotic membrane proteins. *J. Struct. Funct. Genomics.* 6, 33-50 (2005).
30. S. Surade et al., Comparative analysis and "expression space" coverage of the production of prokaryotic membrane proteins for structural genomics. *Protein Sci.* 15, 2178-2189 (2006).
31. F. Bernaudat et al., Heterologous expression of membrane proteins: choosing the appropriate host. *PloS One.* 6, e29191 (2011).
32. S. Eshaghi et al., An efficient strategy for high-throughput expression screening of recombinant integral membrane proteins. *Protein Sci.* 14, 676-683 (2005).
33. E. Gordon et al., Effective high-throughput overproduction of membrane proteins in *Escherichia coli. Protein Expr. Purif.* 62, 1-8 (2008).
34. L. E. Petrovskaya et al., Expression of G-protein coupled receptors in *Escherichia coli* for structural studies. *Biochem. Mosc.* 75, 881-891 (2010).
35. G. Szakonyi et al., A genomic strategy for cloning, expressing and purifying efflux proteins of the major facilitator superfamily. *J. Antimicrob. Chemother.* 59, 1265-1270 (2007).
36. R. D. Finn et al., Pfam: the protein families database. *Nucleic Acids Res.* 42, D222-230 (2014).
37. G.-W. Li, E. Oh, J. S. Weissman, The anti-Shine-Dalgarno sequence drives translational pausing and codon choice in bacteria. *Nature.* 484, 538-541 (2012).
38. C. E. Gamble, C. E. Brule, K. M. Dean, S. Fields, E. J. Grayhack, Adjacent Codons Act in Concert to Modulate Translation Efficiency in Yeast. *Cell.* 166, 679-690 (2016).
39. J. W. Chartron, K. C. L. Hunt, J. Frydman, Cotranslational signal-independent SRP preloading during membrane targeting. *Nature.* 536, 224-228 (2016).
40. G. Van Rossum, F. L. Drake Jr, *Python reference manual* (Centrum voor Wiskunde en Informatica Amsterdam, 1995).
41. P. J. A. Cock et al., Biopython: freely available Python tools for computational molecular biology and bioinformatics. *Bioinformatics.* 25, 1422-1423 (2009).
42. S. van der Walt, S. C. Colbert, G. Varoquaux, The NumPy Array: A Structure for Efficient Numerical Computation. *Comput. Sci. Eng.* 13, 22-30 (2011).
43. O. Tange, GNU Parallel—The Command-Line Power Tool. *Login USENIX Mag.* 36, 42-47 (2011).
44. R Core Team, *R: A Language and Environment for Statistical Computing* (R Foundation for Statistical Computing, Vienna, Austria, 2015; https://www.R-project.org/).
45. RStudio Team, *RStudio: Integrated Development Environment for R* (RStudio, Inc., Boston, Mass., 2015).
46. S. M. Bache, H. Wickham, *magrittr: A Forward-Pipe Operator for R* (2014; https://CRAN.R-project.org/package=magrittr).
47. H. Wickham, The Split-Apply-Combine Strategy for Data Analysis. *J. Stat. Softw.* 40, 1-29 (2011).
48. H. Wickham, R. Francois, *dplyr: A Grammar of Data Manipulation* (2015; http://CRAN.R-project.org/package=dplyr).
49. K. Aho, *asbio: A Collection of Statistical Tools for Biologists* (2015; http://CRAN.R-project.org/package=asbio).
50. K. Weinert, *datamart: Unified access to your data sources* (2014; http://CRAN.R-project.org/package=datamart).
51. H. Wickham, *ggplot2: elegant graphics for data analysis* (Springer New York, 2009; http://had.co.nz/ggplot2/book).
52. E. Clarke, S. Sherrill-Mix, *ggbeeswarm: Categorical Scatter (Violin Point) Plots* (2015; https://github.com/eclarke/ggbeeswarm).
53. B. Schloerke et al., *GGally: Extension to "ggplot2"* (2016; https://CRAN.R-project.org/package=GGally).

54. B. Auguie, *gridExtra: Miscellaneous Functions for "Grid" Graphics* (2015; http://CRAN.R-project.org/package=gridExtra).
55. C. O. Wilke, *cowplot: Streamlined Plot Theme and Plot Annotations for "ggplot2"* (2015; http://CRAN.R-project.org/package=cowplot).
56. H. Wickham, *scales: Scale Functions for Visualization* (2015; http://CRAN.R-project.org/package=scales).
57. S. Garnier, *viridis: Default Color Maps from "matplotlib"* (2016; https://CRAN.R-project.org/package=viridis).
58. E. Neuwirth, *RColorBrewer: ColorBrewer Palettes* (2014; http://CRAN.R-project.org/package=RColorBrewer).
59. M. Harrower, C. A. Brewer, ColorBrewer.org: an online tool for selecting colour schemes for maps. *Cartogr. J.* 40, 27-37 (2003).
60. H. Wickham, *multidplyr: Partitioned data frames for "dplyr"* (https://github.com/hadley/multidplyr).
61. Revolution Analytics, S. Weston, *foreach: Provides Foreach Looping Construct for R* (2015; http://CRAN.R-project.org/package=foreach).
62. Revolution Analytics, S. Weston, *iterators: Provides Iterator Construct for R* (2015; https://CRAN.R-project.org/package=iterators).
63. Revolution Analytics, S. Weston, *doMC: Foreach Parallel Adaptor for "parallel"* (2015; http://CRAN.R-project.org/package=doMC).
64. Revolution Analytics, S. Weston, *doParallel: Foreach Parallel Adaptor for the "parallel" Package* (2015; https://CRAN.R-project.org/package=doParallel).
65. H. Wickham, P. Danenberg, M. Eugster, *roxygen2: In-Source Documentation for R* (2015; https://CRAN.R-project.org/package=roxygen2).
66. J. Zhou, K. E. Rudd, EcoGene 3.0. *Nucleic Acids Res.* 41, D613-624 (2013).
67. G. D. Schuler, J. A. Epstein, H. Ohkawa, J. A. Kans, Entrez: molecular biology database and retrieval system. *Methods Enzymol.* 266, 141-162 (1996).
68. UniProt Consortium, Reorganizing the protein space at the Universal Protein Resource (UniProt). *Nucleic Acids Res.* 40, D71-75 (2012).
69. P. Cock, [BioPython] Downloading CDS sequences (2009), (available at http://biopython.org/pipermail/biopython/2009-January/004886.html).
70. L. Chen, R. Oughtred, H. M. Berman, J. Westbrook, TargetDB: a target registration database for structural genomics projects. *Bioinformatics.* 20, 2860-2862 (2004).
71. J. F. Tomb et al., The complete genome sequence of the gastric pathogen *Helicobacter pylori*. *Nature.* 388, 539-547 (1997).
72. P. Lechat, L. Hummel, S. Rousseau, I. Moszer, GenoList: an integrated environment for comparative analysis of microbial genomes. *Nucleic Acids Res.* 36, D469-474 (2008).
73. S. T. Cole et al., Deciphering the biology of *Mycobacterium tuberculosis* from the complete genome sequence. *Nature.* 393, 537-544 (1998).
74. E. Dobrovetsky et al., High-throughput production of prokaryotic membrane proteins. *J. Struct. Funct. Genomics.* 6, 33-50 (2005).
75. K. E. Nelson et al., Evidence for lateral gene transfer between Archaea and bacteria from genome sequence of *Thermotoga maritima*. *Nature.* 399, 323-329 (1999).
76. J. F. Peden, thesis, University of Nottingham (2000).
77. M. dos Reis, L. Wernisch, R. Savva, Unexpected correlations between gene expression and codon usage bias from microarray data for the whole *Escherichia coli* K-12 genome. *Nucleic Acids Res.* 31, 6976-6985 (2003).
78. J. N. Zadeh et al., NUPACK: Analysis and design of nucleic acid systems. *J. Comput. Chem.* 32, 170-173 (2011).
79. R. Lorenz et al., ViennaRNA Package 2.0. *Algorithms Mol. Biol. AMB.* 6, 26 (2011).
80. J. R. Coleman et al., Virus attenuation by genome-scale changes in codon pair bias. *Science.* 320, 1784-1787 (2008).
81. Z. R. Yang, R. Thomson, P. McNeil, R. M. Esnouf, RONN: the bio-basis function neural network technique applied to the detection of natively disordered regions in proteins. *Bioinformatics.* 21, 3369-3376 (2005).
82. W. C. Wimley, T. P. Creamer, S. H. White, Solvation energies of amino acid side chains and backbone in a family of host-guest pentapeptides. *Biochemistry (Most.).* 35, 5109-5124 (1996).
83. D. M. Engelman, T. A. Steitz, A. Goldman, Identifying nonpolar transbilayer helices in amino acid sequences of membrane proteins. *Annu. Rev. Biophys. Biophys. Chem.* 15, 321-353 (1986).
84. M. Kuhn, Building predictive models in R using the caret package. *J Stat Soft* (2008).
85. C. Weihs, U. Ligges, K. Luebke, N. Raabe, in *Data Analysis and Decision Support*, D. Baier, R. Decker, L. Schmidt-Thieme, Eds. (Springer-Verlag, Berlin/Heidelberg, 2005; http://link.springer.com/10.1007/3-540-28397-8_36), pp. 335-343.
86. M. G. Kendall, A New Measure of Rank Correlation. *Biometrika.* 30, 81 (1938).
87. T. Joachims, (ACM Press, 2002; http://portal.acm.org/citation.cfm?doid=775047.775067), p. 133.
88. X. Robin et al., pROC: an open-source package for R and S+ to analyze and compare ROC curves. *BMC Bioinformatics.* 12, 77 (2011).
89. E. R. DeLong, D. M. DeLong, D. L. Clarke-Pearson, Comparing the areas under two or more correlated receiver operating characteristic curves: a nonparametric approach. *Biometrics.* 44, 837-845 (1988).
90. A. Canty, B. D. Ripley, *boot: Bootstrap R (S-Plus) Functions* (2015).
91. F. Cunningham et al., Ensembl 2015. *Nucleic Acids Res.* 43, D662-669 (2015).
92. D. Smedley et al., The BioMart community portal: an innovative alternative to large, centralized data repositories. *Nucleic Acids Res.* 43, W589-598 (2015).
93. T. W. Harris et al., Worm Base 2014: new views of curated biology. *Nucleic Acids Res.* 42, D789-793 (2014).
94. S. R. Engel et al., The reference genome sequence of *Saccharomyces cerevisiae*: then and now. *G3 Bethesda Md.* 4, 389-398 (2014).
95. K. De Schutter et al., Genome sequence of the recombinant protein production host *Pichia pastoris*. *Nat. Biotechnol.* 27, 561-566 (2009).
96. H. Nordberg et al., The genome portal of the Department of Energy Joint Genome Institute: 2014 updates. *Nucleic Acids Res.* 42, D26-31 (2014).
97. V. M. Markowitz et al., IMG 4 version of the integrated microbial genomes comparative analysis system. *Nucleic Acids Res.* 42, D560-567 (2014).
98. I. Uchiyama, M. Mihara, H. Nishide, H. Chiba, MBGD update 2015: microbial genome database for flexible ortholog analysis utilizing a diverse set of genomic data. *Nucleic Acids Res.* 43, D270-276 (2015).

99. C. Loader, *locfit: Local Regression, Likelihood and Density Estimation*. (2013; https://CRAN.R-project.org/package=locfit).
100. J. Schindelin et al., Fiji: an open-source platform for biological-image analysis. *Nat. Methods*. 9, 676-682 (2012).
101. C. A. Schneider, W. S. Rasband, K. W. Eliceiri, NIH Image to ImageJ: 25 years of image analysis. *Nat. Methods*. 9, 671-675 (2012).
102. J. Towns et al., XSEDE: Accelerating Scientific Discovery. *Comput. Sci. Eng.* 16, 62-74 (2014).
103. Y. Xie, in *Implementing Reproducible Computational Research*, V. Stodden, F. Leisch, R. D. Peng, Eds. (Chapman and Hall/CRC, 2014; http://www.crcpress.com/product/isbn/9781466561595).
104. J. W. Tukey, Exploratory data analysis (Addison-Wesley Pub. Co, Reading, Mass, 1977), *Addison-Wesley series in behavioral science*.
105. E. R. Tufte, *The visual display of quantitative information* (Graphics Press, Cheshire, Conn., 2nd ed., 2001).

What is claimed is:

1. A method for membrane protein expression, comprising:
   selecting an initial set of sequences with known protein expression level for a membrane protein;
   transforming the initial set of sequences to sequence features including nucleotide features, protein features, or both;
   dividing the initial set of sequences into a training set of the sequence features and a test set of the sequence features;
   creating a supervised machine learning model based on the training set of the sequence features and related expression levels, the model providing statistical analysis of the sequence features of the training set in relation to the related expression levels;
   validating the supervised machine learning model by confirming relation between the sequence features of the test set and the related expression levels;
   providing a distinct set of membrane protein sequences, each membrane protein sequence of the distinct set having an untested or unknown protein expression level;
   performing a statistical modeling on each membrane protein sequence of the distinct set with the supervised machine learning model to provide an expression level prediction for each membrane protein sequence of the distinct set;
   ranking membrane protein sequences of the distinct set having different expression levels, wherein the ranking is based on the expression level predictions, the ranking identifying candidate membrane protein sequences above a $50^{th}$ percentile of an entirety of the distinct set of membrane protein sequences,
   selecting an experimentation subset having membrane protein sequences selected from the candidate membrane protein sequences having positive expression and identified to be above the $50^{th}$ percentile;
   performing experimental testing on the experimentation subset such that expression levels are determined for each member of the subset, creating a positive result set of sequences that have positive expression of the membrane protein as determined by the experimental testing; and
   expressing into a host membrane other proteins having the membrane protein sequences of the positive result set of sequences.

2. The method of claim 1, wherein the initial set of sequences are alpha-helical membrane proteins.

3. The method of claim 2, wherein the alpha-helical membrane proteins have a single transmembrane domain.

4. The method of claim 2, wherein the alpha-helical membrane proteins have multiple transmembrane domains.

5. The method of claim 1, wherein the features are transformed using one or more of the following methods: scaling, centering, PCA, autoencoding, and discretization.

6. The method of claim 1, wherein at least one feature is described by one or more of the following categories: overall codon usage, codon pair score, tRNA adaptation index, 5' codon usage, GC content, 5' RNA Structure, overall RNA structure, Shine-Dalgarno-like sites, overall disorder, loop disorder, TM size/count, hydrophobicity, loop charge, loop length, and length/pI.

7. The method of claim 1, wherein the supervised machine learning model uses a supervised-learning statistical framework.

8. The method of claim 6, wherein the statistical framework is a support vector machine.

9. The method of claim 6, wherein the statistical framework is a neural network.

10. The method of claim 6, wherein the statistical framework is a decision tree.

11. The method of claim 1, wherein the distinct set of membrane protein sequences are alpha-helical membrane protein sequences.

12. The method of claim 11, wherein the alpha-helical membrane proteins have a single transmembrane domain.

13. The method of claim 11, wherein the alpha-helical membrane proteins have multiple transmembrane domains.

14. A non-transient computer readable media comprising instructions to carry out the method of claim 1.

15. The method of claim 1, wherein at least one sequence feature of the sequence features is described by one or more of the following categories: overall codon usage and codon pair score.

16. A computer-implemented method for membrane protein expression, comprising:
   collecting an initial set of sequences with known protein expression level for a membrane protein;
   applying a transformation on the initial set of sequences to provide sequence features including nucleotide features, protein features, or both, the initial set of sequences including a training set of the sequence features and a test set of the sequence features;
   running a supervised machine learning model trained on the training set of the sequence features and their known expression levels on the test set of sequence features, the model providing statistical analysis of the sequence features of the training set in relation to the related expression levels;
   providing a distinct set of membrane protein sequences, each membrane protein sequence of the distinct set having an untested or unknown protein expression level;
   running the supervised machine learning model to create a statistical modeling on each membrane protein sequence of the distinct set, providing an expression level prediction for each membrane protein sequence of the distinct set in a ranking by expression level predictions;
   creating a set of candidate membrane protein sequences above a $50^{th}$ percentile in the ranking, the set of candidate membrane protein sequences containing an experimentation subset;
   performing experimental testing on the experimentation subset such that expression levels are measured for each member of the subset, creating a positive result set of sequences that have positive expression of the membrane protein as determined by the experimental testing; and
   expressing into a host membrane other proteins having the membrane protein sequences matching the positive result set of sequences.

* * * * *

SEQUENCE LISTING

```
<160> NUMBER OF SEQ ID NOS: 2

<210> SEQ ID NO 1
<211> LENGTH: 140
<212> TYPE: DNA
<213> ORGANISM: Unknown
<220> FEATURE:
<223> OTHER INFORMATION: nucleotides 1-140 of a membrane protein coding
      sequence

<400> SEQUENCE: 1
atggctaaac aaccgggatt agattttcaa agtgccaaag gtggcttagg cgagctgaaa      60
cgcagactgc tgtttgttat cggtgcgctg attgtgttcc gtattggctc ttttattccg     120
atccctggta ttgatgccgc                                                  140

<210> SEQ ID NO 2
<211> LENGTH: 140
<212> TYPE: PRT
<213> ORGANISM: Unknown
<220> FEATURE:
<223> OTHER INFORMATION: amino acids 1-140 of a membrane protein amino
      acid sequence

<400> SEQUENCE: 2

Met Ala Lys Gln Pro Gly Leu Asp Phe Gln Ser Ala Lys Gly Gly Leu
1               5                   10                  15

Gly Glu Leu Lys Arg Arg Leu Leu Phe Val Ile Gly Ala Leu Ile Val
            20                  25                  30

Phe Arg Ile Gly Ser Phe Ile Pro Ile Pro Gly Ile Asp Ala Ala Val
        35                  40                  45

Leu Ala Lys Leu Leu Glu Gln Gln Arg Gly Thr Ile Ile Glu Met Phe
    50                  55                  60

Asn Met Phe Ser Gly Gly Ala Leu Ser Arg Ala Ser Ile Phe Ala Leu
65                  70                  75                  80

Gly Ile Met Pro Tyr Ile Ser Ala Ser Ile Ile Ile Gln Leu Leu Thr
                85                  90                  95

Val Val His Pro Thr Leu Ala Glu Ile Lys Lys Glu Gly Glu Ser Gly
            100                 105                 110

Arg Arg Lys Ile Ser Gln Tyr Thr Arg Tyr Gly Thr Leu Val Leu Ala
        115                 120                 125

Ile Phe Gln Ser Ile Gly Ile Ala Thr Gly Leu Pro
    130                 135                 140
```